(12) United States Patent
Stenger et al.

(10) Patent No.: US 8,032,310 B2
(45) Date of Patent: Oct. 4, 2011

(54) COMPUTER-IMPLEMENTED METHOD, COMPUTER READABLE STORAGE MEDIUM, AND APPARATUS FOR IDENTIFICATION OF A BIOLOGICAL SEQUENCE

(75) Inventors: David A Stenger, Herndon, VA (US); Jennifer Thornton, Alexandria, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 687 days.

(21) Appl. No.: 11/177,647

(22) Filed: Jul. 2, 2005

(65) Prior Publication Data

US 2007/0065832 A1    Mar. 22, 2007

Related U.S. Application Data

(60) Provisional application No. 60/590,931, filed on Jul. 2, 2004, provisional application No. 60/609,918, filed on Sep. 15, 2004, provisional application No. 60/631,437, filed on Nov. 29, 2004, provisional application No. 60/631,460, filed on Nov. 29, 2004, provisional application No. 60/691,768, filed on Jun. 16, 2005.

(51) Int. Cl.
*G01N 33/48* (2006.01)
(52) U.S. Cl. ............. 702/20; 703/2; 703/11; 211/41.12
(58) Field of Classification Search .................. None
See application file for complete search history.

(56) References Cited

U.S. PATENT DOCUMENTS 6,519,583 B1* 2/2003 Koleszar et al. ................ 707/1
7,024,312 B1* 4/2006 Selifonov et al. ............. 702/19

OTHER PUBLICATIONS

Examination report in application NZ579206.
Examination report in NZ579206 (Nov. 29, 2010).
Chou et al., "DNA sequence quality trimming and vector removal" Bioinformatics, 17, 1093-1104 (2001).

* cited by examiner

*Primary Examiner* — Carolyn L. Smith
(74) *Attorney, Agent, or Firm* — Amy L. Ressing; Joseph T. Grunkemeyer

(57) ABSTRACT

A computer-implemented biological sequence identifier (CIBSI) system and method for selecting a subsequence from biological sequence data according to at least one selection parameter. The at least one selection parameter corresponds to a likelihood of returning a meaningful result from a similarity search.

14 Claims, 31 Drawing Sheets

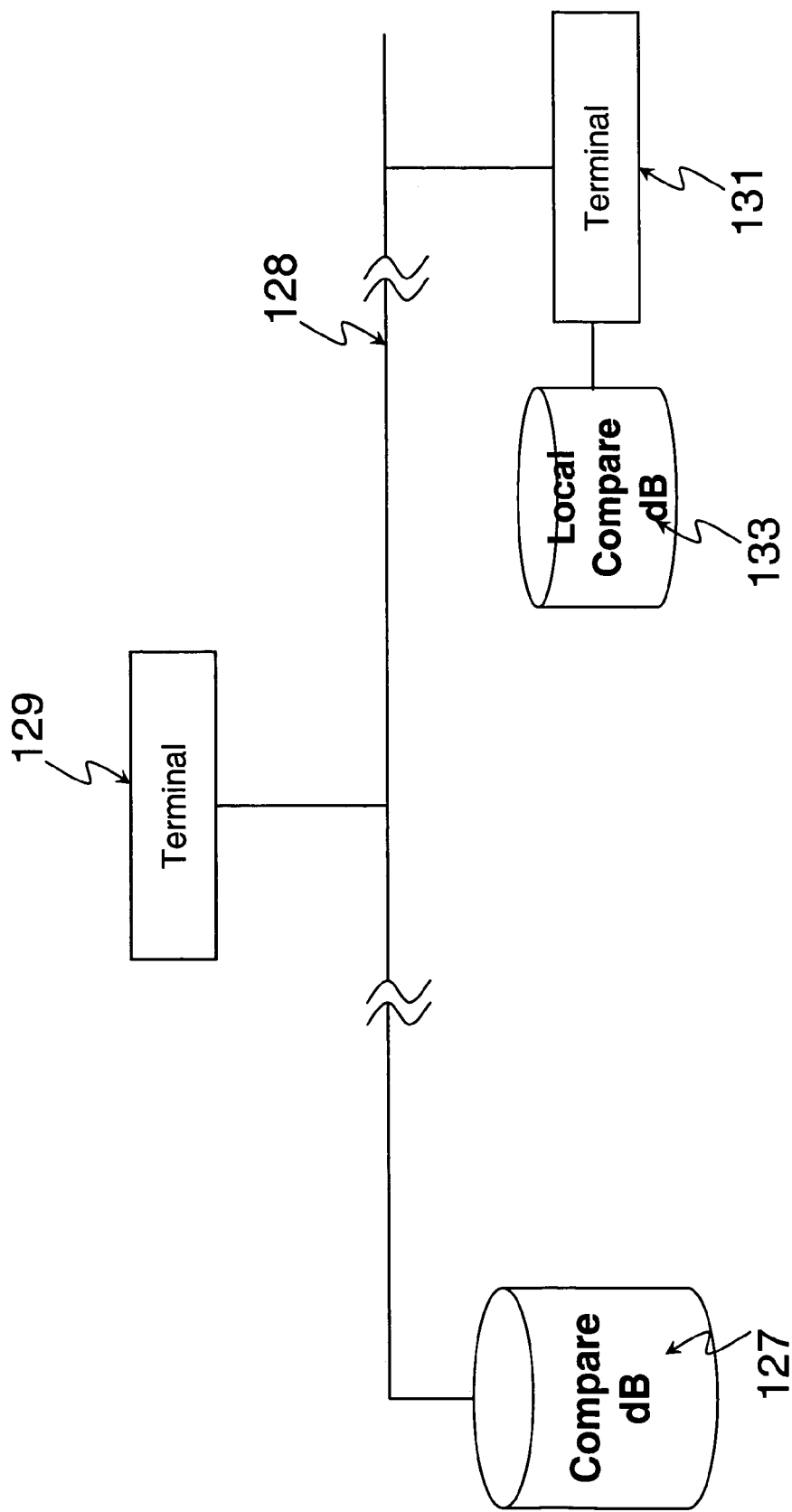

Fig. 1(d)
Background Art

>Ad4E1A:Ad4_Prototype-serial_dilution1    Start=12;End=1313
Subsequence:
cacctncgctgcncgancngtatgatctggngtggatgtgnccgagagcgacncaagagaaggcgtaatgattatttagcgatgccg
cgctgctagctgncgagngctgcagnectgcagacagagactcttcactgcatacccctgncacgncagaggtgagaagagatcc
ccggagcttaaatggdaaagntagcactgcgttgctgctgaggaaatgnctgnnncaagcagatgatgaggacgagnggcgntcagancgcg
cgagccatgngtgcagccgtcagcgagagcttgcactggaacgngccgccttgcncgacacgctgtagctttgtgatttcatcgca
ncaatactgggagatcaagctgtgtatgtgcctttgctatatgagagcgnacaaccattgtgttncagtaaagtgtgattaagtgaactttn
aangagcaaangtaghgtgactnngtgatgactnnttnttttnttnnttntnthtntttwthnhnkthynnttytmnhnnnnnknt
Subsequence Length: 556
Number of Subsequence Base Calls: 493
Percentage of Subsequence Base Calls: 89%
Percentage of Target: 43% lcl|ad4 No definition line found; Length = 35990
    evalue: 0.0 for Ad4E1A
gi|209874|gb|M14918.1|ADRDE1AA Adenovirus type 4 E1A region; Length = 2042
    evalue: 0.0 for Ad4E1A
gi|171105037|gb|AF394196.1|AF394196 Simian adenovirus 25, complete genome; Length = 36521
    evalue: 2.63705E-155 for Ad4E1A
gi|33694802|tpg|BK000413.1| TPA: Simian adenovirus 25, complete genome; Length = 36519
    evalue: 2.63705E-155 for Ad4E1A
lcl|ad4_vaccine No definition line found; Length = 35119
    evalue: 1.11896E-123 for Ad4E1A
lcl|ad4_Navy_Fieldstrain No definition line found; Length = 35090
    evalue: 1.03083E-43 for Ad4E1A
lcl|ad4_AirForce_Fieldstrain No definition line found; Length = 35089
    evalue: 1.60947E-42 for Ad4E1A >Ad4FIBER:Ad4_Prototype-serial_dilution1    Start=12;End=1245
Subsequence:
annanmtnnncncncaccgancgtncttcatcaacnctccctcnnnnnnttcagntggattccaagaaaagccctggngtgtgtccn
nnggnntgnncgacnctgtcnchccaagaatggggaaattaccctcaagntnnnannnnnnnganctgncgnctcgggnaanctcatcg
caaacncagnaaacaaggccattgnnnnntccagtttttyccaaacaacacatttnnnnnttaacatggntacccttatncaccaagtgg
caaatcancctttaccagttctccaacantagnaannnccaacatttgaatncaanannmnnnnnctttgctaaacaggnngttgatg
tcagtgcagccgnctgncagtagcttccaccttncattgntgataaaggggatataaagattaccctaaacaggngttgatg
ttncancaggagntgcaattgaaagcaacatcagttgggctaaaagtgtaaaatttgaaagntggtgccatagcctaaacaacatggtaagnnsn
nnngnktnggaaccgnagtncagaaaacaggagtcaatgaattaacttttgtgacaacgcctgcctcagtgcaaatactngcagaaaatg
ggcatatgtgctgcaatagagntctgaataagnctgatgatnatgccaagcccatgccactgtakchgnttggntgttgaagtggaaacttaaaccaa
ntgcaaactancactttgcnnaannanannngcagncaaatnctgccactttgatgcaaatggtgttcttttaacagaacacttnanncnnaaaaaatctgg
gctacaagcacagtaagcagtgctcaagttttctcacgtttgatgcaaaatggtgttcttttgcaaattcaacgcttatccaacggacccaaaggtt
ctactnntaaatataatagtggtcaagtacacgantgggngntgttcaaacccctgtcttcttactacttcttaactcttaatgtagtactgatg

```
>EMBOSS_001
ATGGGCACCCCATCGATGATGGGCCAgTGGGCATACATGCACATCGCCGGACAGGATGCT
TCGAGTACCTGAGTCCGGGTCTGGTGCAGTTCGGCCCGCGCCACAGACACCTACTTCAGT
CTGGGGAACAAGTTTAGAAACCCCACGTGGCGCCCACCACGATGTGACCACCGACCGt
AGCCAGCCGgCTCATGCTCGCGCTTCGTGCCCGTTGACCGGGAGGACAATACCTACTCtTAC
AAAGTGCGcTACACCGCTGGCCtGTGGGCACAACAGAGTGCTGGACATGGCCAGCACaTTC
TTTGACATTCGGgGcGTGCTGGATAGeGGcGCGCCCCAATAcTeTCAGTGGATgGATaCaGannnt
TACAACTcaCTGGCCTCCtAAGGGCCGGCCCCAATAcAtCcAGTGGATgGATaCaGannnt
actcAggAAatgnnnnanaactnGAcAATGCngnaaactgncaccacggaagangnanan
nangnnnnnnnnnnacatAcACcTaTTGCcAtnnAnaaatgCTgCCATGaaAaGgtGAg
ACnccttnnncTGggaAAAtAcALAAGAtgaaGgtcTGCcAATTGGaAtAGAtatTAct
nCtactgaaGgAgangACAAaCCaATTTATgCtcgATAAAACtTAtCaaCCAGAACCTCAA
GTTGGAcGAGgAAaacCTGGAcTGAcACtGATGGAACAAAtGAAAAAAtaTGGAAGGGcAGAGC
TCTaAAAccagcTACtAAAATGAAACCTGCTACCGGtTCTCTTTGCAAACCTACaAACAt
AAAAGGgGGtcAgGCTaAAAtaaAAgnAatcAaaaACAacaaccgaaGaGccatngAtc
CTgAgtATccGATAtTgATaTGnGeaTTtTTGACGGtAaAaatAcTGtTGnagcTgac
TTGGACCCGAAATTGTaaTGTACACaAAAATGTCaATTGGAAACTCCAGAcACTCAT
gTTGTATACAAACCtGGAACtcGGAtcgcnAgCTCTcArGcArGCAAATTTGGGTCAACAAGCC
ATGCCTAAAACAGAACCCAacTACATTGGcTTCAGgGACAACTTTATcGGgCTcATGTACTAC
AACAGCTCTGGCAATATGGGaGTTCTGCCcGGcGGCCAAGcaTCcCAGCTGAATGCAGTGGTT
GACTTGCAgGACAGAAACACTCGAACTGTCATATCAGCTCTTGCTTGCtGATCTCTGGtGAC
AGAACCAGATACTTCAgATGTGGAATCAGGCCTGTGGACAGCTATGATCCtGATGTgCCg
ATTATTGAAAATCATGGtGTGAGGATGAACTGCCAAACTACTGCTTTCCgtTGGATGGT
GTaGGcnAccaacAGACACTTACCAAGGcATTAAAgcTAAAAacaGAtCGaanTnCTGaA
tnnnnnnnnnnnngGGGACAAAGATGnTAacgcAgtTAgaactgCTAATGAAATAagct
gTAGGcAATCCCtTTTGCCATGGAACCTCTGTATCTGCCAGATaatTACAAATACCgCCAgCCAACATCACT
CTGCCcaTcAACACCAACCTACgAGTACATGGAACGTCTCGGACCCATGAATGGACAATGTcAAT
GTGGATCCCTACATCAATCAACATTGGGCGCCAGTGTGTCTCTGGACCCCATGGACAATGGTCAAT
CCATTCAACCACCACCGCAATGCTGCCTGCCTGCAGTCCCATGCTTCTGGGCAATGGt
CGTTAtGTGCCTTTCCAATACCTACACCTACGAGTGGACtACTTCAGaAAGGATGTAACATGGTCCTG
CAGAGTTCCCTTGGAAATGACCTccgAcAGAAGTGGCGCCAACTACCCCCATTCACCACCATC
AACCTCTATGCCACCTTCTTCCCCATGGCCTCACACACCGcCTCCAcCcTTGAAGCCATG
CTGCGCAACGACACGACCACCCATTGATCAGTCATTCACGACTACCTCTGCAGCCAACATGCTc
TACCCCATCCCGCCAAtGCAACCAACAACTTCACcAGaCTCAAAACCAAGGAGACTCCCTCTCTGGGaTCa
GCCTTCGACGCTGGTTCCTTCAcCAGACTCAAAACCAAGGAGACTCCCTCTCTGGaTCa
GGGTTCGAcCCCTACTTCGtTacTCTGGcTCTATcCCCTACCTAACTGGCACCTTtTAC
CTCAACACACACTTCAAGAAGGTCTCCATCATGTTTGACTCTTCAGTCAGCTGGCCTGGC
AATGACAGGCTGCTCGACCCGAAACGAGTTTGAAATCAAGCCACtCGTGACGGGGAAGGa
TACAACGGTGGCCCAATGCAACATGACCAAAGACTGTTCCTGTCCAGATGCTtGCCAAC
TACAACATTGGCTACCAGGGCTTcTACATCcCGcAGGGaTACAAGGATCCGATCTACTCC
TTcTTCAGAAACTTCCAGCCCACTGAGCCAGGTGGTTGATGAGGTTAAtTACAAgGAC
TACAAAGCCGTCACCTACCcTACCAACACAACACTCTGGCTTTGtAGGtTACCTtcCg
CCtACcATGCGaCAAGGgCAAcCCtAccCTACCAAGGCCACCCGCTCATCGGACAC
ACTGCCGTTAACAGTGTCACCCAGAAAAAGTTCCTGCGCCAGGACCATGTGGGGcATt
CCcTTCTCCAGCAACTTCATGTCCATGGGcGCCCTTTACCGACCTGGACAGAGAACaTGTCTC
TATGCCAACTCcGCCCATGCCGTGACATGTCTTCGACGTGGTCAGAGTGCACCAGCCACCGC
ACCCTCTTATCTTCTTCCGAAGTCTTCGACAGCCTGGACCTCTCGGGCCGCAACCACCgC
GGGCTCATCGAGGGGCGTCTACCTGCGCACCGTTCTCGGGCCGCAACCGCCACCACTAA
```

```
                   401                                                       450
Ad4FS_AF_hexon     AGTGG............................................... AAGGAT
Ad4FS_army_hexon   AGTGG............................................... AAGGAT
Ad4vaccine_hexon   AGTGG............................................... AAGGAT
Ad4_hexon          AGTGG............................................... AAGGAT
Ad16_hexon         AGTGG............................................... AAGGAT
Ad3FS_navy_hexon   AGTGGAT.........AGTTAC............................... AACGAAT
Ad3_hexon          AGTGGAT.........AGTTAC............................... AACAAAT
Ad7_hexon          AGTGGAT.........AGTTAC............................... AGCAGGA
Ad7FS_navy_hexon   AGTGGAT.........AGTTAC............................... AACGGGA
Ad7vaccine_hexon   AGTGGAT.........AGTTAC............................... AACGGGA
EMBOSS_001         AGTGGATGGATACAGANNNTACTCAGGA.......................... AATGGNN
Ad21_hexon         AGTGGATTGCTGAAGGCGT.AAAAAAA........................... GAAGAT
Ad50_hexon         AGTGGCTTAATAAGGG....AGATGAA........................... GAGGAT
Ad34_hexon         AGTGGTTGGATAAGGGAGTTACAAGCACTGG.......CCTAGTGGACGAC
Ad1_hexon          AGTGGGAACAAGAAGAACCAACTCAGGAAATGGCTGAAGAACTTGAAGAT
Ad5FS_hexon        AATGGATGAAGCTGCTACTGCTCTTGAAAT.......AAACCTAGAAGAA 451                                                      500
Ad4FS_AF_hexon     GC..........TAACAGCAAA.............................AT....GCATACC
Ad4FS_army_hexon   GC..........TAACAGCAAA.............................AT....GCATACC
Ad4vaccine_hexon   TC..........TGACAGCAAA.............................AT....GCATACC
Ad4_hexon          TC..........TGACAGCAAA.............................AT....GCATACC
Ad16_hexon         TC..........TGACAGCAAA.............................AT....GCATACC
Ad3FS_navy_hexon   CG..........AGACAATGCAGTAACTACCA....................CCAC..AAACACA
Ad3_hexon          GG..........GGACAATGCAGTAACTACCA....................CCAC..AAACACA
Ad7_hexon          GA..........AGAAAGAGCAGTAACTACCA....................CCAC..AAACACA
Ad7FS_navy_hexon   GA..........AGACAATGC......CA.......................CCAC..ATACACA
Ad7vaccine_hexon   GA..........AGACAATGC......CA.......................CCAC..ATACACA
EMBOSS_001         NNANAACTNGACAATGCNGNAACTGNCA........................CCACGGAAGANGNANA
Ad21_hexon         GGGGGATCTGAGAAGAGGAAGAGAAAAATCTCACCAC...............TTACACT
Ad50_hexon         GGGGAA..GACGACCAACAAG...............................CTAC...ATACACT
Ad34_hexon         GGCAATACTGATGATGGGGAAGAGGCAGAGGAGGCCAAAAAGCAAC.......ATACACT
Ad1_hexon          GAGGAGGAGGAGCAACAACGAAGACGAAGTAGACGAG
Ad5FS_hexon        GAGGACGATGACAACGAAGACGAAGTAGACGAG
```

```
>Manually modified cons to include missing Ad5/1
AACAGGATGCTTCGGAGTACCTGAGTCCGGGTCTGGTGCAGTTCGCCCGCG
TGGCCACCCCATCGATGATGCCCCAGTGGGCATACATGCACATCGCCGG
CCACAGACACCTACTTCAGTCTGGGGAACAAGTTTAGAAACCCCACGGTG
GCGCCCACCCACGATGTGACCACCGACCGTAGCCAGCGGCTGATGCTGCG
CTTCGTGCCCGTTGACCGGGAGGACAATACCTACTCTTACAAAGTGCGCT
ACACGCTGGCTGTGGGCGACAACAGAGTGCTGGACATGGCCAGCACATTC
TTTGACATTCGGGGCGTGCTGGATAGAGGCCCTAGCTTCAAGCCCTACTC
CGGCACTGCTTACAACTCACTGGCTCCTAAGGGCGCGCCCAATACATCTC
AGTGGATGGATACAGANNNTACTCAGGAAATGGCTGAAGAACTAATGGNN
NNANAACTNGACAATGCNGNAACTGNCAAGGAGG CCACGGAAGANGNANA
NNANGNNNNNNNNNCNACATACACCTATTGGCATNNNNNNAATGCTGCCA
TG CCAATTGGAATAGATATTACTNCTACTGAAGGAGANGACAAACCAATTTA
AAAGGTGAGACNCCTTNNNCTGGGAAAATTACTAAAGATGAAGGTCTG
CCAATTGGAATAGATATTACTNCTACTGAAGGAGANGACAAACCAATTTA
TGCTGATAAAACTTATCAACCAGAACCTCAAGTTGGAGAAGAAACTTGGA
CTGACACTGATGGAACAAATGAAAAATATGGANGGCAGAGCTCTAAAACC
AGCTACTAAAATGAAACCCTGCTACGGGTCTTTTGCCAAACCTACAAACA
TAAAAGGGGGTCAGGCTAAAATAAAAGNAATCAAAAACAACAACCGAAGG
AGCCATNGATCCTGAGTATCCAGATATTGATATGNGAATTTTTTGACGGT
AAAAATACTGTTGNAGCTGACTTCGATCCTGAAATTGTAATGTACACAGA
AAATGTTGATTTGGAAACTCCAGACACTCATGTTGTATACAAACCTGGAA
CTTCGGATGCNAGCTCTCATGCAAATTTGGGTCAACAAGCCATGCCTAAC
AGACCCAACTACATTGGCTTCAGGGACAACTTTATCGGGCTCATGTACTA
CAACAGTACTGGCAATATGGGAGTTCTGGCCGGCCAAGCATCTCAGCTGA
ATGCAGTGGTTGACTTGCAGGACAGAAACACTGAACTGTCATATCAGCTC
TTGCTTGATTCTCTGGGTGACAGAACCAGATACTTCAGTATGTGGAATCA
GGCTGTGGACAGCTATGATCCTGATGTGCGCATTATTGAAAATCATGGTG
TGGAGGATGAACTGCCAAACTACTGCTTTCCGTTGGATGGTGTAGGTCNA
CCAACAGACACTTACCAAGGTATTAAAGTTAAAACAGATGAAANTNCTGA
ATNNNNNNNNNNNNAGTGGGACAAAGATGNTAACGCAGT
TAGAACTGCTAATGAAATAGCTGTAGGCAATCCTTTTGCCATGGAAATTA
ACATCCAAGCCAACCTGTGGAGAAGTTTCCTGTATTCCAATGTGGCTCTG
TATCTGCCAGATAATTACAAATACACGCCAGCCAACATCACTCTGCCCAC
TAACACCAACACCTACGAGTACATGAACGGGCGGGTGGTGGCCCCATCGC
TGGTGGATTCCTACATTAACATTGGCGCCAGGTGGTCTCTGGACCCCATG
GACAATGTCAATCCATTCAACCACCACCGCAATGCTGGCCTGCGCTACCG
GTCCATGCTTCTGGGCAATGGTCGTTATGTGCCTTTCCACATACAAGTGC
CTCAGAAATTCTTTGCTGTCAAGAACCTACTGCTTCTACCCGGCTCCTAC
ACCTACGAGTGGAACTTCAGAAAGGATGTGAACATGGTCCTGCAGAGTTC
CCTTGGAAATGACCTCCGAACAGATGGTGCCACCATAAGTTTCACCAGCA
TCAACCTCTATGCCACCTTCTTCCCCCATGGCTCACAACACCGCCTCCACC
CTTGAAGCCATGCTGCGCAACGACACCAATGATCAGTCATTCAACGACTA
CCTCTCTGCAGCCAACATGCTCTACCCCATCCCTGCCAATGCAACCAACG
TTCCCATCTCGATCCCCTCTCGCAACTGGCCGCCTTCAGCGGCTGGTCC
TTCACCAGACTCAAAACCAAGGAGACTCCCTCTCTGGGATCAGGGTTCGA
CCCCTACTTCGTCTACTCTGGCTCTATTCCCTACCTGGATGGCACCTTTT
ACCTTAACCACACTTTCAAGAAGGTCTCCATCATGTTTGACTCTTCAGTC
AGCTGGCCTGGCAATGACAGGCTGCTGACTCCAAACGAGTTTGAAATCAA
GCGCACTGTGGACGGGGAAGGATACAACGTGGCCCAATGCAACATGACCA
AAGACTGGTTCCTGGTCCAGATGCTTGCCAACTACAACATTGGCTACCAG
GGCTTCTACATCCCTGAGGGATACAAGGATCGCATGTACTCCTTCTTCAG
AAACTTCCAGCCCATGAGCAGGCAGGTGGTTGATGAGGTTAATTACAAGG
ACTACAAAGCCGTCACCTTACCCTACCAACACAAACAACTCTGGCTTTGTA
GGTTACCTTGCGCCTACTATGCGACAAGGGCAACCCTACCCCGCCAACTA
CCCATACCCGCTCATCGGAACTACTGCCGTTAACAGTGTCACCCAGAAAA
AGTCCTGTGCGACAGGACCATGTGGCGCATTCCCTTCTCCAGCAACTTC
ATGTCCATGGGCGCCCTTACCGACCTGGGACAGAACATGCTCTATGCCAA
CTCCGCCCATGCGCTGGACATGACTTTTGAGGTGGATCCCATGGATGAGC
CCACCCTGCTTTATCTTCTTTTCGAAGTCTTCGACGTGGTCAGAGTGCAC
CAGCCACACCGCGGCGTCATCGAGGCCGTCTACCTGCGCACACCGTTCTC
GGCCGGCAACGCCACCACATAA
```

Fig. 20

>EMBOSS_001_modified_hexon_cons
Subsequence:
ATGGCCACCCCATCGATGaTGCCCCAgTGGGCATACATGCACCTGAGTCCTCGGAGTACCTGAGTTCGCCCGCGCCACAGACACCTACTTCAGTCTGGGAACAAG
TTTAGAAACCCCACggTGGCGCCcACCCACGATGTGACCACCGAgCCAGCCgCTGATGCTGCGCTTCGTGCCCGGAGGAGACAATACCTACTCTACAAAGTGCgCTACAcgCTGGCGTGGGC
GACAACAGAGTGCTGGACATGGCCAGCACATTCGgGGCGTGCTGGATAGAGaGGcCCTAGCTTCAAGCGCTaCTCCGGCACtgCTCACAACtCaCTGGCTCCAAGGGGCGCGCCCAATACTctCAGTG
GAtgGATaCaGammntactcAggAAATGGCTGAAGAACTAatgcnnnanaactnGAcAATGCngnaactgncaAGGAGGccacggaagangnanannangnnnnnnnnncacalAcACcTaTTGGcAtnnnnnaatGCTgCCATGaAaGgtGAgA
CnccttnncTGggaAAAtActAAAAGAtgaaGGtcTGCcAATTgGaAnGAtatTACtnCTactgaaGGAganGACAaaCCAATTTATGCtGATAAAACTATCAaCCAGaACCTCAAGTTGGAGAaGAaactTGGAcTGAcACTGATGG
AACAAATGAAAAATaTGGAnGGAcGAGCTCTaAAAcagcTACTAAAAATGAAACCcTGCTACgGgTCTTTTGCcAAACCTGaAAATTGTaACCAgAAAATGTGAtTTGCAAAACTCAAataAAgnAatcAaaAaCAacaacgaaGGGaGccatngAtc
CTgAgtATcaGATATtGATaTGnGaaTTTTTGacGGtAaAaatAcTGtTGnagctgacTTcgatCCtGaAATTGTaaTGTACACAgAAAATTGTGAtTTGnagctgacTTgatCCtGaAATTGTaACACAgAAAATGTGAtTTACACAAAACCtGGAACtttCgGAtgcnAg
CTCtcAtGcAaATTTGGGTCAACAAGCCATGCCTAACAGACCCAACTACATTGGCTTCAgGGACAcATTGGCTTCAgGGACAcTCATGtTGnagctgacTTgatCCtCAgGGACAcATTGGCCTCAgGGACAcCTGGaGTTCTGGCcGGcCAAGCaTCtCAGCTGAATG
CagTGGTTGACTTGCGAGGAGATGAACTGCCaaAcTAcTGcTTTCCgtTGGATGGATCTGTaGGtcnAccaAcAGAACACTTACCAAGGtATTAAAAcaGAtGaaanTnCTGaAtnnnnnnnnagtGGGAcAAAGATGntAacgcAgtTAg
aactgCTAATGAAATagctgTAGGCAATcctTTTGCCATGAAATTAACATCCAAGCcAACCTgTGGAGAAGTTTcCTgTAtTCCAATGTGGCTCTGTATCTgCCAGATAatTACAAATACACgCCagCCAACATcACTCTGCC
CaCTAACACCAACACCTAcGAGTACATGAACGGCGAgTGGTGTTAGGcGCCAGgTGGTCTTcAAGAACCTaCTgCTTTCGCTGTCTgCAGAACCTAATAaCATTGGcGCCAGgTGGTCTTcAAGAACCTaCTgCTTTCcACCGAGGCCATGGGCCGCCCTACACCTACGAGTTGGAACTTCAGaAA
TGGCCTGCGCTACCGTCCATGCTTCTGGGCAATGGGCGGGTGGTTATGTGGCCAATGGGCAATGGGCGGGTATGTGGCGGTATGGGCAATGGGCGGTATGTGGCcCATGCTTCTGGGCAATGGGCGGGTATGTGGCGGTATGGGCAATGGGCGGTATGTGGcGGaAntGACCTccGaAcAGATGGtGCcAcCATaAGTTTCACCAGCATCCAACAGCATCCAACAGTTTCACCAGCATGGCtCACAACACCGCcTTCCACcCTTGAAGCCAT
GCTGGGCAACGACACCAATGATCAGTCATTCGAAGCTATCAGTCATTCGCcGAGCAACATGCTCTCTGCcGAGCAACATGCTCTCCCCATCCCGGCAACCAAcgTTCCCATcTcTCCATCCCcTCTGGACCTTCGCCATCTCCATCTCGGGACCTCCCTTCAGcGGCTGGT
CCTTCACcAGaCTCAAAACCAGgAGACTCCcTCTCTCTGGaTCaGGGTTCGAcCCCCTTACTCGTcTCTATTTACCTTAACCAACATGGACACCAACATGGATCACCCATCTGAACATCATGTGATCCCATCATCCATCACCACTTTCAAGAAGTCTCCATCATGTT
TGACTCTTCAGTCACTACAACATTGGCTACCAGGGCTTCTACATCCtgAGGGATACAAGGATGCCATGCGaCAAGgCCAACtACtTGCGaCAAGgCCAACtACtGCCCAATCTGGAACCCATCCCAATCTGGAACACTGTCCAGCCATGCCATACCCGCTCATGGAACtACTGCCGTTAAcAGTGTCACCCAGAAAA
AGTTCCTGTGCCAGGAGCATGTGGCAGGGCCATCCCCTTTCCAGCAACTTCATGtCTCATGGAGACAGAACAtCTCTATGCCCATGCCATGCCCATGCCATGCCCATGCCATGCCCATGCCCATGCCCATGCCCATGCCATGCCGACATGACTTTTGAGGTGG
ATCCCATGGATGAGCCCACCACCGTCCTGCTTTATCTCTTTCGAAGTCTTCGACGTGGTCAGAGTGCACACCGGCACACCGGCACCGTTCTCGGCCGGCAACCGCCAC
ATAA
Subsequence Percentage of Target: 100%
Subsequence Length: 2961
Number of Subsequence Base Calls: 2899
Percentage of Subsequence Base Calls: 98%
lcl|AY599834 | Human Adenovirus Serotype 3 | 35,345bp; Length = 35345
 evalue: 0.0, score: 2296.06 for null
lcl|AY594255 | Human Adenovirus Serotype 7 | 35,305bp; Length = 35306
 evalue: 0.0, score: 2272.27 for null
gi|86019|emb|Z48571.1|MAVH7HEXN Mastadenovirus h7 hexon gene; Length = 2918
 evalue: 0.0, score: 2272.27 for null
gi|11968173|gb|AF065065.3|AF065065 Human adenovirus type 7 pVI core protein (pVI) gene, partial cds; hexon protein (hexon) gene, complete cds; and p23 protease gene, partial cds; Length = 3237
 evalue: 0.0, score: 2272.27 for null
gi|3641840|emb|X76549.1|AV3HEXO3 Adenovirus type 3 hexon gene; Length = 2835
 evalue: 0.0, score: 2264.34 for null
lcl|AY601634 | Human Adenovirus Serotype 7, US Navy Field Strain | 35,198bp; Length = 35198
 evalue: 0.0, score: 2258.4 for null

Fig. 21

```
>ad4_bl2seq.out
nnnnnnnnnnnnnnnnnnnnnnnnnnnnnnnnnnnntgtaggcaatcctttgccatgaaatnaacatccaagccaac
ctgtggagnannnnnnnnnnnnnnnnnnnnnnnnnnnnnnnnnnnnnnnnnnnnnnnnnnnnnnnnnnnntgcccacn
aacaccacacctacgagtacatgaacggncgggtggtggcnnnnnnnnnnnnnnnnnnnnnnnnnnnnnnnnnnnnn
nnnnnnnnnnnnnnnnnnnnnnnnnnnnnatcnttcaaccaccaccgcaatgcnnnnnnnnnnnnnnnnnnnnnnnn
nnnnnnnnnnnnnnnnnnnnnnnnnnnnnnnnnnnnnnnnnnnnnnnnnnnnnnnccggntcctacacctacgagtg
gaacttcngnnnnnnnnnnacatgntcctgcagagttccctggnnnnnnnnnnnnnnnnnnnnnnnnnnnnnnnnnn
nnnacctctangccaccttctcccatgccncacaacaccgcctccacnttgangccatgctgccaacgacaccaatgancanmm
nnnnnnnnnnnnnnnnnnnnnnnnnnnnnnnnnnnnnnnnnncaacgtnccatccctcncgcaact
gggccgcgcttnnnnnnnnnnnnnnnnnnnnnnnnnnnnnnnnnncnggttgaccctacttcgtcact
cnggctcnnnnnnnnnnnnnnnnnnnnnnnnnnnnnnnnnnnnaccacacnttcaagaaggtctccatcannnnnnnnnnnnnnnn
nnnnnnnnnnnnnnnnnnnnnnnnnnnnnnnnnnnnnnnnnnnnnnnngatacaacgtggcccantgcaa
catgaccaangactggttcctggtccagatgtngccnnctacaacatnggctaccagggcttctacnnnnnnnnncaaagganc
gcatgtactccttcnnnnnnnnnnnnnnnnnnnnnnnnnnnnnnnnnnnnnnnnnncctacccgcaactacccntaccc
nctaccaacaacaactcngggcttnnnnnnnnnnnnnnnnnnnnnnnnnnnnnnnnnnnnnnnnnnatgtgggcgcatnccctctccagcaactt
gctcatcggnnnnnnnnnnnnnnnnnnnnnnnnnnnnnnnnnnnnnnnnnnnnnnnnnnnnnnngcgccannnnnnnnnnnnnnnnnnm
catgtccatgggcgcnctnnnnnnnnnnnagaacatgctctatgcnaactcgcccannnnnnnnnnnnnnnnnnnnnn
nnnnnnnnnnnnnnnnnnnnnnnnnnnnnnnnnnnnnnnnnagtgcaccagccncaccgcggcgtcatngag
gccgtctacctgcgcacnnnnnnnnnnnnnnnnnnn
```

```
>EMBOSS_001
ATGCCACCCCATCGATGaTGCCCaGtGGGcCATaCATGCACATCGCCGaCACGGAtGCT
TCGGAGTACCTGAGTCCGGGTCTGGTCCAGTTCGCCCGcCACCCaGACACCTACTTCAGT
cTGGGAACAAGTTTAGAAACCCAGGTGGCCGCcACCCACGATGTGACCACCGACCGc
AGCCAGCGGcTGAtGCTGCCGCTTcGTCCCCGTGACCGGAGGACAAtACCTACTCGTAC
AAAGTGCGcTACACGCTTGGCGTGGGCGACAACAGAGTGCTGACATGGCCAGcACCTcC
TTTGACATcCGcGGcGGCTGCTGDAtaGgGGAGCCGCCAACACCTgcCAGTGGAanngGaTgCtgnn
TACAAcAccCTGGCTCCCAAGGGaGCGCCAACACCTgcCAGTGGAanngGaTgCtgnn
nnnnnnnnnACnnAGcAgAnnnnnnnnagenaaannnnnsnnntnccaccAcgcAcA
CcTTTGGgataGCTGCCATGacgGGtGctactgGglaaaAtgatgaAGCtgAaGGgGcTgc
ceaATTgcAtAcnnAataACTgCtgeActgeaCaaccaaATTTATGCtGATAaaACaTt
cCAACCAGAACCCAAGTTGGAaAtgAaaacTTGGgtTGAcAccaATGGtaCAaAtGAAAA
ATaTGGaAGAGCTCTaAaggaceCTAcAaAAATGAAACccTGCTatGGtTCtTtG
CCAAaCCTACcAACaAaaAAGGcGGcCAgGCTaAAcctAaAaAtTaAgaAccgCCGgc
gaACcAgTcgaggCTgactAgcCTGATATtGATcTGGAtTcTtTTGAcgGAgnAgatAt
TGcTGactAACTtcgaTCcaaAaTTGTaaTGTACACaGAAAATGTGACTTGgAaACTC
CAGACTCATaTcGTATACAAaCCCGAACtgagGAcgcCAgCTcTcAagcCAATTTGG
GTCAaCAagCCATGCCTACACAGACCCAACTACATTGGCTTCAGaCacAaTTTATtGGgC
TcATGTACTACAACACaCTGCAaATATGGGgTcTCGGCCGTcAAgCATCtCagCTGA
ATGCtGTCGTTGACTTGCAaGACAGAAACTGTCAACTGTCaTaCaCAGCTcTTgCTTGACT
CTCTGGGcGACAGAACCaGgTACTTCAGTATGTGGAATCAGGCGGTGGACAGCTATGATC
CtGATGTGcCATATTGAAAAtCATGGtGTGAGGAGTGAACTGCCaAacTACTGCTTTC
CgTGATGGtGTGGGnnnAtCaacAgAcACTTACCAagGCGtaTTAaagcTAaaACAAtg
CaGgttctgaannnnnnnnnagTGGGaCAAagAtGacAACCaaaGTTagTactGCTA
ATGAAATccatgTAGGCAATCCTTTTGCCATGGAAATCAAcAATCCAAGCCAacCTGTGGA
GaAgtTTcCTgTATtCCATGTGCCtTgTATcTGcCaGATaaaTACAAaTACACaCGg
CCAACATCACTCCTGCCcAACACCAACACCAGTGACGAGTACATGAACGGCGGTGGTgg
CgCCATGCTGGTgGACTcCTACATCAAACATTGGgCcaGcTGGTcTCTGACCCATGG
ACAAtGTaAATCcATTcAACCACCACCGCCAAGCtcGGCcTGCCCAAGCCaACCTGTGGA
TGGGCACAATcGGgCGGTCTATGTGGCCCTTTCCACAaTcCAagTGCCCAGAAATTCTTTGCtgTcA
AGAACCTaCTgCTtCTgCcgGgCTCCTACACCTACGAGTGGAACTTcAgAaAGCAtcTGA
ACATGgtCCTGCAGAGTTCCCTTGGAaAtgACCTccCaCAGAGAGTGGCCaCCATcAgtT
TCACCAGCATCAACCTCTaAtGCCACCTTCTTCCCcATGGCCCACACCGCtTCCACGC
TTGAagGCCATGCTGCCAACGACACCAaTGACCAGTCaTTCAACGACTACCTCTcGCAG
CCAACATCCTcTACCCCATCCCGGCCACGAACAACGTTCCCATtCTCCATCCccTCcC
GCAACTGGGcGCcCTTCaGcGGCTGGTCCTTCACgaGaCTCAaaaCCAaGGAGACCCCT
CcCTGGGcTCaGGGTTCGACCACCACCTTCAAGAaGGTCTCCATCaCGtTTGACTCTTCaGTCA
GCTGGCCCGGCAaTGACGGGCTGCTGACTCCCAACGAGTTTGAAATCAAGGCACCGTGG
AcGGgGaAGGaTACAACGTGGCCCAaTGCACATGGCCTTcTACATcCTGAGGGCTACAAGGATC
TGCTtGCCaACTaCACATTGCTACCAGGCCTTcTACATcCTGAGGGCTACAAGGATC
GCATGTACTCCTTcTTCaGaAACTTCCAGaATGCAGgCAGCCAGGCTGGTtGAtGAGGTTA
AcTACAagGaCTACaAagCCGTCACCtTacCaTATcAACAACAACTCtGGCTTTGTaG
GaTACCTTGCGCCtACtATGCcCaCGGcCAacCCTACCaGCCAAcTACCCaTACCCGC
TCATcGGaActactGCCGGTTAacAGcGTcACCCAGAAAAGTTCcTgTGCCAGGacCA
TGTGGGCGCATcCcCTTcCaGCAACTTCATGTcCATGGGCGCCTtACcGACCTGGaC
AGAACaTGCTCTATGCcAACTCCAACAAGAATGTCTGGCATCATGACTTTGAgGTgACCCA
TGGATGAGcCcACCCTTgCTtTATcTTcTTTGAAGTCTTCACGTTGCAGTGCACC
AGCcaCACCGCGGGCCATCGAGGCCGTcTACCTGCCACACCTGGTTCTCGCCGGcAACG
CCACCACATAA
```

COMPUTER-IMPLEMENTED METHOD, COMPUTER READABLE STORAGE MEDIUM, AND APPARATUS FOR IDENTIFICATION OF A BIOLOGICAL SEQUENCE

CROSS REFERENCE TO RELATED PATENT APPLICATION

The present application claims priority to U.S. provisional Application Ser. No. 60/590,931, filed on Jul. 2, 2004, U.S. provisional Application Ser. No. 60/609,918 filed on Sep. 15, 2004, U.S. provisional Application Ser. No. 60/631,437 filed on Nov. 29, 2004, U.S. provisional Application Ser. No. 60/631,460 filed on Nov. 29, 2004 and U.S. provisional Application Ser. No. 60/691,768 filed on Jun. 16, 2005. This application is also related to U.S. application Ser. No. 11/177,646. The entire contents of these applications are incorporated herein by reference.

The Sequence Listing submitted on compact disc (2 copies) as part of the second preliminary amendment to the application is incorporated herein by reference. The file name is "11177647 Seqence Listing.ST25". The CD was created on Jul. 27, 2006 and the file contains 44,716 bytes.

COPYRIGHT NOTICE

A portion of the disclosure of the patent document contains material which is subject to copyright protection. The copyright owner has no objection to the facsimile reproduction by anyone of the patent document or patent disclosure as it appears in the U.S. patent and Trademark Office patent file or records, but otherwise reserves all copyright rights whatsoever.

BACKGROUND OF THE INVENTION

1. Field of the Invention

The present invention is relevant to a variety of automated selection systems including automated sub-sequence selection systems for usage with any method group of nucleic acid or protein sequences generated by alternative methods. The system is configured to automatically select sets of sub-sequences from incomplete nucleotide sequence data obtained from resequencing DNA microarrays, according to parameters predetermined by the system or determined by a user, for selecting sequence subsets that are optimally suitable for comparison against a collection of predetermined database sequences using one or more similarity search algorithm(s). Embodiments of the invention also enable the further analysis and presentation of relevant results returned by a similarity search resulting from submission of one or more subsequences. Aspects of the invention described herein distinguish between combinations of sequence signatures that arise from a mixture of multiple sequence targets (e.g. microbial organisms) or from a rearrangement of sequences within a single target. Embodiments of the method are also capable of assigning relative abundances of mixed target sequences based on relative signal intensity values from the DNA microarray itself. Moreover, an aspect of the invention is an integral component of an iterative process for designing resequencing DNA microarrays using "prototype" sequence tiles to represent a range of related target sequences (e.g. pathogens).

2. Description of the Related Art

The convergence of biology with engineering and computer science has led to the emergence of biotechnology and bioinformatics which, among many other goals, aim to rapidly obtain and analyze genomic and proteomic sequence information for diagnosis of disease. The experimental viability and widespread availability of such methodologies are due in no small part to the emergence of DNA microarrays (Stenger et al., 2002).

Generally, microarray fabrication applies methods of microprocessor manufacturing to create "gene chips" capable of rapidly and reliably identifying sequences of DNA or proteins that are present in a biological sample. Here, the term "microarray" refers to any type of planar substrate or alternative matrix presenting a high multiplicity ($10^2$ to $10^6$) of individual sites, each presenting probes (immobilized nucleic acids or antibodies) designed to selectively capture complementary strands of a target (i.e. gene or gene transcript) analytes in solution. By design, DNA microarrays enable the simultaneous interrogation of thousands of gene or gene transcript elements.

In using a resequencing DNA microarray for genetic analysis, a solution containing amplified and fluorescently-tagged genetic targets are passed across the microarray comprised of a plurality of oligonucleotide probes in a "tiled" format (Kozal et al., 1996). Complementary sequences in the sample bind to the corresponding probes contained on the microarray. The microarray is then analyzed using, for example, a laser scanner that records the intensity of light emission from the microarray's probes. The recorded intensities are then analyzed by array-specific software used to make "base calls," which is a term describing an algorithmic method of identifying to a certain degree of probabilistic certainty the sequence of nucleic acids (adenine; A, thymine; T, cytosine; C, or guanine; G) contained in the biological sample of interest. A broader IUPAC definition code is also used to describe less precise base calls (see U.S. Provisional Application Ser. No. 60/590,931 filed on July 2, 2004 entitled "Resequencing Pathogen Microarray", supplemental data, Appendix J "gdas_manual pdf" page 255). If the target sequence is sufficiently homologous to the appropriate tile region of the resequencing microarray (fewer than 1-2 base substitutions per 25 bases) then a complete resequencing of the target is possible. However, the hybridization to the tile region is interrupted when the target sequence contains insertions, deletions, or base substitutions at frequencies of greater than 2 substitutions per 25 bases of target sequence. This results in the "no [base] call" (N) being made from the corresponding sequences on the microarray tile region. N calls also result when the concentration of the target nucleic acid in solution is low or when there are interfering level of competing background nucleic acids in the hybridization solution. Incomplete biological sequence information can also be generated by a number of other nucleic acid and protein sequencing technologies.

The primary intended application of resequencing microarrays is to detect low probability single nucleotide polymorphisms (SNPs) or mutations within a limited range of target sequences. However, although not conventionally performed currently in industry, sequence output of the microarray can also be compared against sequence databases to allow identification of target sequences. The most prevalent comparison method, or similarity search algorithm, for sequence data currently in use is Basic Local Alignment Search Tool, commonly known as and referred to herein as "BLAST." Numerous variants exist, including Washington University BLAST (WU-BLAST), NCBI-BLAST, FASTA, MPsrch, Scanps, and BestFit (Korf, Yandell & Bedell, 2003). Such comparisons generally yield a number of possible matches in terms of certainty (measured probabilistically) that the tested sample includes the matched biological subject for which a sequence is known. The sequence output by the intensity analysis of the microarray is then often compared to a database that includes known sequences of biological subjects which could include pathogenic microbes. However, one normally skilled in the art of molecular biology would not be capable of visually determining the best sequence sections from a tiled region containing A, C, T and G base calls punctuated and in some cases dominated by varying numbers of no-calls (N).

The use of microarrays for the purposes of genetic sequencing and identification has drastically increased the capability of even a single researcher to extract a large amount of sequence data from a biological sample for comparison against an even larger number of previously sequenced organisms and biological substances. However, the researcher is unable to utilize the information in a time-effective manner. Ambiguous results are also problematic for a researcher submitting sample sequences for comparison due to excessive wait times and poor (inconclusive or conflicting) results associated with attempts to match ambiguous subsequences. Accordingly, a widely-practiced method of obtaining more relevant results from sequence comparison is for a researcher to review sequence output searching for subsequences that appear to have a higher probability of returning a relevant result. In particular, many researchers often find themselves manually and subjectively selecting, or visually parsing, certain subsequences for comparison against those in the sequence database. As a result, a researcher expends time and resources for relatively slowly and subjectively optimizing the sequence data for submission to the similarity search. Thus, the current solution for the above-noted resource utilization problem leads to additional time and resource requirements demanded of the researcher. Moreover, as the current solution is subjective as well as time-intensive, the net gain with respect to facilitating the advancement (and acceleration) of genomic research is ambiguous at best.

However, as noted above the vast repositories of known biological sequences are often contained in shared computing resources. These shared computing resources require vast amounts of data storage capacity, as well as robust and powerful tools with which to compare a submitted sequence to those contained within the database. As the amount of sequence data produced (and submitted) by researchers increases with the improvement and increasing availability of microarrays for general research use, the burden placed on shared databases (and associated systems) in terms of bandwidth and processing requirements increase dramatically. In other words, the increase in data made possible by widespread use of microarrays often leads to less efficient utilization of shared bioinformatics computing resources.

For example, if sequences containing a large percentage of ambiguous sequence data (Ns) are submitted, the sequence database's computing resources will be spent trying to find matches for inherently ambiguous sequences, resulting in all possible similarity search results with low certainty values. FIG. 1(a) is an exemplary flowchart illustrating a process that might currently be performed with methods available to the industry. In this example, nucleotide or amino acid sequence data 103 corresponding to a sequence of interest is submitted for comparison against a known sequence database using a similarity search 109.

The submitted sequence(s) 103 when compared to database records, 109 might or might not return statistically significant or meaningful results. Here, by definition, to "compare" means to perform a similarity search of a query sequence against a database of sequence records using any one of a large number of algorithms for determining similarity (e.g. BLAST). Sequendes that are said to be "comparable" have a sufficient degree of similarity to at least one sequence in a database to result in the return of at least one statistically significant (user defined) result. It is straightforward for an end user to visually identify and select contiguous stretches of nucleotide base calls (comprised of only A, T, C, or G residues) or amino acids that might be comparable. However, as the number or percentage of "Ns" contained within target sequences increases, it becomes exponentially more difficult for the end user to visually determine the comparability of either the entire sequence or subsequences within it.

The results 111 include high probability matches 111a, lower probability matches 111b, and a significant number of statistically insignificant results 111c that can be attributed to a chance match with the database. Ns are treated as "aNy" (wild card) characters by similarity search algorithms meaning the N could be any of the four base residues or gap when the default parameters are used. In the case of a resequencing DNA output, an N indicates the resequencing algorithm could not resolve the call and can correspond to any of the four base residues (A, T, C or G) or to empty space (Korf et al., 2003). In the case that too many non-calls (Ns) are included in the submitted sequence, then the similarity search (e.g. BLAST) will calculate E (expect) values higher than the acceptable E (expect) value (e.g. 1.0e−9) indicating the chances are greater that the returned sequence is not unique. Similarly, shorter sequences may have higher E values indicating their lack of use to the end user in determining the presence of unique DNA material. The results 111, including the numerous ambiguous results 111c, are then left to be analyzed 113 by the researcher.

In the case of FIG. 1(a), other users are shown submitting their sequences of base calls to the shared sequence database 109, which handles these additional requests for local alignment searches. As described above, the submission of ambiguous sequences by multiple users to a shared sequence alignment resource often results in available computing resources being spent to serve only a small number of sequence submissions.

Figure 1D:
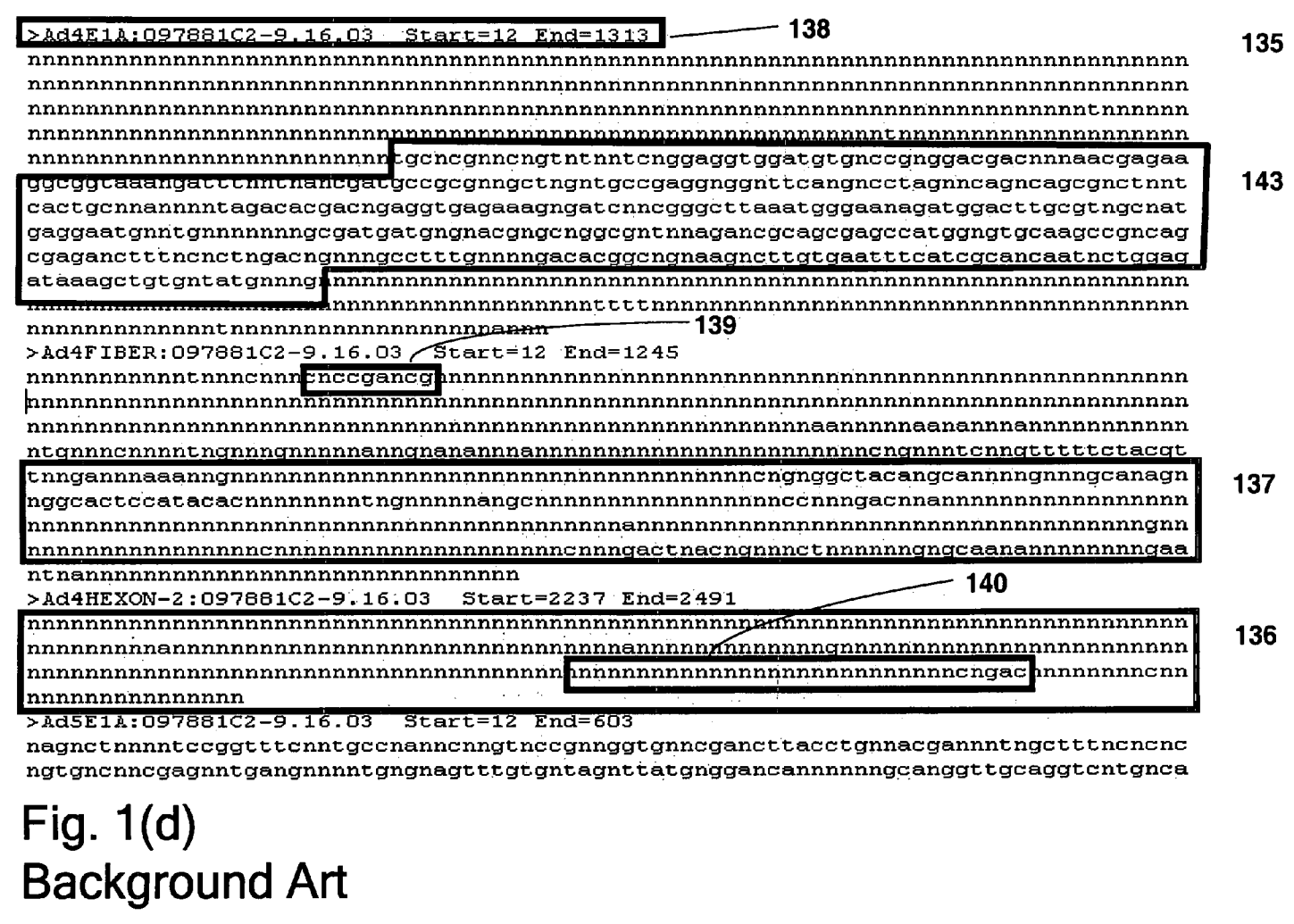

FIG. 1(b) illustrates this alternative case often found in practice in the industry that is problematic with regard to researcher time consumption. In contrast to the previously illustrated case, the sequence data 103 is altered in a cut and paste operation 119 performed manually by a human researcher. More specifically, the human researcher often visually scans the raw data output and subjectively copies and pastes subsets of the raw data output 119 that appear to contain fewer "Ns" and submits these subjective selections 121 for comparison 109. However, as the selection of subsets is performed subjectively and repetitively for a large amount of raw data, the human-selected submissions 121 often include comparable 121a and non-comparable 121b data. Consequently, the results from the BLAST comparison 123 still include a wide array of possible matches, ranging from high probability matches 123a, to low probability matches 123b which are often caused by selections in which there are to many non-calls 123c as opposed to the anticipated result of a low probability match caused by a less similar sequence match.

As discussed above, FIG. 1(c) is a schematic drawing of a general system layout for interaction with sequence database servers through computer terminals over a wired or wireless network 128. In some case, sequence database (and associated server) 127 is located remotely from a researcher's terminal 129. Alternatively, some facilities have built custom sequence databases 133 which are accessible through a local terminal 131. However, the above-noted problems with time and shared resource consumption are significant in either configuration with a higher increase in time consumption at a public database level.

A variety of different factors can contribute to the inability of a resequencing DNA microarray to make non-ambiguous base calls. In pure target samples, the hybridization patterns necessary for base calling (Cutler et al., 2001; Kozal et al., 1996) are interrupted whenever a stretch of target sequence is sufficiently dissimilar from the probe sequences that are tiled on the microarray surface. This results in the introduction of N calls into the interrupted positions of the resequencing microarray output file. The same effect occurs when the target molecules are present in low concentration and/or when the target sample is not pure but contains varying amounts of other nucleic acid molecules that can bind non-specifically to the tiled probes with low affinity, resulting in a lowered signal-to-noise ratio of hybridization (fluorescence) signals across the probe sets. To illustrate how these factors can determine whether sequences are comparable or non-comparable data, FIG. 1(d) shows an example of a resequencing DNA microarray output file that results when incomplete hybridization occurs. In the illustrated case, the sequences 135 are in FASTA format, however alternative sequence data formats are equally suitable, including, but not limited to plain, EMBL, GCG, GenBank, and IG. Within the example sequence 136 are sequence subsets 140 (subsequences). Example subsequences 140 include a subsequence with an excessive number of non-calls (Ns) 137, a subsequence that is too short to return meaningful results from a similarity search such as BLAST 139, and a subsequence that is likely to produce a meaningful result 143. Additionally, multiple sequences are set off by aliases, located in the sequence header 138, referencing the probe tile set that is physically present on the microarray surface.

Overall, the above-noted problems with the current state of industry practice are fundamentally related to researcher time consumption and shared resource allocation. More specifically, the increased amount of subsequence data obtained from samples results in rapid increases in the utilization of shared resources such as sequence comparison databases. Such rapid increases necessitate efficient use for supporting a growing community (in terms of researchers and data). With the aim of using shared resources more effectively, researchers are now often faced with the need to devote time and resources to subjectively and manually selecting sequence subsets for comparison.

As stated above, there is a critical need for advanced diagnostic systems that can rapidly detect both known and unanticipated sequences. More particularly, there remains a critical demand for DNA microarray techniques that reduce the need for human work input and increase the efficiency of shared resource utilization, especially in the case of shared similarity search databases and systems.

In addition to the above-described problems in the industry regarding more effective use of researcher and shared computing resources, the evolution of world events and the emergence of infectious disease and bioterrorism in mainstream society have led to a growing sentiment amongst the scientific community and lay people alike that new, rapid, and accurate techniques for threat identification and eradication must be developed. The concept of broad-spectrum pathogen identification has considerable and obvious appeal to both medical practice and national defense. It is within this framework that the present inventors have endeavored. Furthermore, there remains a need for more ready and robust determination of mixtures and recombinants in biological samples from biological sequence data, regardless of the source of the sequence data.

SUMMARY OF THE INVENTION

A first aspect of the present invention provides a computer-implemented biological sequence identifier (CIBSI) system and method for selecting a subsequence from biological sequence data according to at least one selection parameter. The at least one selection parameter corresponds to a likelihood of returning a meaningful result from a similarity search.

One embodiment of the present invention provides a system for automatic selection of optimal sequences or subsequences for comparison against a predetermined set of known sequences. Optionally, the system automatically takes a highly fragmented sequence interspersed with Ns, and selects comparable subsequences that are likely to return a "meaningful" result from a similarity search.

Optionally, the system utilizes a sliding window-type algorithm for selecting subsequences. Subsequently, the system automatically returns outputs from a similarity search to the end user that allow probabilistic assignments of the likelihood that a given set of base calls correspond to a particular predetermined sequence.

In an additional embodiment of the present invention, sequence information derived from a base-calling algorithm, as applied to a microarray hybridization pattern, is used to identify individual biological entities present in a test sample. Optionally, the sequence of target sequences determined by resequencing probes of the microarray is used to query a database using a similarity search algorithm. Similarity search algorithms include, but are not limited to, commonly used local alignment (e.g. Smith-Waterman, BLASTN) sequence alignment algorithms to statistically determine the probability that a given target sequence corresponds to a specific sequence in a database record (Korf et al., 2003).

Further, an additional embodiment of the present invention presents results of the similarity search to a user regarding whether at least one target sequence is present in the sample.

In another embodiment of the present invention, signal intensity data (for example, obtained from a microarray) is handled by the system and associated with the sequence data. The output of a similarity search is assembled or distilled for presentation to a user to communicate whether a biological entity (including, but not limited to, a pathogen) is present or not. Further, intensity data is correlated with the above output to ascribe relative abundances of a present biological entity (including, but not limited to, a pathogen). Optionally, the system provides an end user with an estimate (quantization) of the relative amount of pathogen that was detected in a resequencing microarray assay.

A second aspect of the present invention identifies mixtures of sequences and sequences indicating a recombination event. In one embodiment, the system automatically detects overlapping or homologous sequence fragments on different tiled regions of a microarray, allowing inference of a mixture of sequences. In an additional embodiment, the system determines that the sequence outputs from different tiled regions are not overlapping but correspond to a contiguous sequence that may be used to infer a genetic recombination event. Optionally, the system discriminates between mixtures of different and genetic recombination between different sequences.

A third aspect of the present invention provides a method of designing "prototype" regions (see U.S. Provisional Application Ser. No. 60/590,931) of resequencing DNA microarrays. In this case, a set of related target sequences are compared using a multiple sequence alignment algorithm such as ClustalW or Clustal_X (Thompson et al., 1997; Thompson, Higgins & Gibson, 1994) or another method of searching for sequence databases for partially conserved regions such as HMMer (Eddy, 1998) the outputs of which are used to create a consensus sequence comprised of the most frequent nucleotides at a given residue position in an alignment column. The consensus sequence consists of a mixture of consensus base calls and no-calls (Ns) where no consensus can be achieved for each of the residue positions in the alignment columns.

Optionally, an embodiment of the present invention searches for candidate regions to tile onto a resequencing DNA microarray by determining those regions having the acceptable balance of conserved and variable nucleotides to allow hybridization of target to the resequencing microarray tile region but still allow for enough sequence variability. This will allow sequence similarity search-based identification of the target sequences comprising the alignment used to generate the consensus.

In alternative embodiments, nucleotide or amino acid sequences come from an alternate form of sequence generator, including those described in (Shendure et al., 2004) and partial amino acid sequences that may be assembled to form a protein sequence. Selected embodiments of the system handle amino acid or protein sequence data in which relative position is conserved.

In other selected embodiments, the nucleotide sequences include a ribonucleic acid (RNA) transcript that codes for protein synthesis. In a manner similar to that described for determining mixtures versus recombination events in target nucleic acids, a mixture of RNA transcripts can be hybridized and thus resequenced on a tiled microarray to produce raw data that can be analyzed using the present invention to determine relative quantities of different RNA transcripts as compared to recombination through transcript editing and alternative splicing (Leipzig, Pevzner & Heber, 2004).

Additional embodiments of the present invention are applicable to nucleotides, transcriptional products, amino acids, or any mixture thereof. Further, the present invention is also applicable to various types of sequence databases and similarity search algorithms to the extent that is well known in the art. Moreover, embodiments of the present invention are suited or adaptable for a wide range of methods and/or devices that generate a sequence data, including, but not limited to, manual or automated Sanger sequencing, shotgun sequencing, conventional microarrays, resequencing microarrays, microelectrophoretic sequencing, sequencing by hybridization (SBH), Edman degradation and variants thereof, Cyclic-array sequencing on amplified molecules, Cyclic-array sequencing on single molecules, and non-cyclical, single-molecule, real-time methods such as nanopore sequencing (Shendure et al., 2004).

The above objects highlight certain aspects of the invention. Additional objects, aspects and embodiments of the invention are found in the following detailed description of the invention. Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1(c) is a schematic drawing of a general system layout for interaction with a comparison database and server;

FIG. 1(d) shows an example of a sequence output from analyzing a microarray demonstrating poor hybridization (the four sequences are, in order, SEQ ID NO.4, SEQ ID NO.5, SEQ ID NO.6, and SEQ ID NO.7);

FIG. 9(b) illustrates an exemplary output of an embodiment of the invention (the four sequences are, in order, SEQ ID NO.9 and SEQ ID NO.10);

FIG. 17 is an exemplary graphical representation of a multiple alignment (the fifteen sequences are, in order, SEQ ID NO.11, SEQ ID NO.12, SEQ ID NO.13, SEQ ID NO.14, SEQ ID NO.15, SEQ ID NO.16, SEQ ID NO.17, SEQ ID NO.18, SEQ ID NO.19, SEQ ID NO.20, SEQ ID NO.21, SEQ ID NO.22, SEQ ID NO.23, SEQ ID NO.24, and SEQ ID NO.25);

FIG. 18 is an example of a consensus sequence generated by a multiple alignment (SEQ ID NO.26);

FIG. 19 is another exemplary graphical representation of a multiple alignment including a consensus sequence (the sixteen sequences are, in order, SEQ ID NO.27, SEQ ID NO.28, SEQ ID NO.29, SEQ ID NO.30, SEQ ID NO.31, SEQ ID NO.32, SEQ ID NO.33, SEQ ID NO.34, SEQ ID NO.35, SEQ ID NO.36, SEQ ID NO.37, SEQ ID NO.38, SEQ ID NO.39, SEQ ID NO.40, SEQ ID NO.41, and SEQ ID NO.42);

FIG. 20 illustrates an example of a modified consensus sequence (SEQ ID NO.43);

FIG. 21 is an exemplary output of an embodiment of the present invention (SEQ ID NO.44);

FIG. 22 is an example of simulated hybridization output according to an embodiment of the present invention (SEQ ID NO.45);

FIG. 23 illustrates another example of a consensus sequence (SEQ ID NO.46); and

The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 1A:
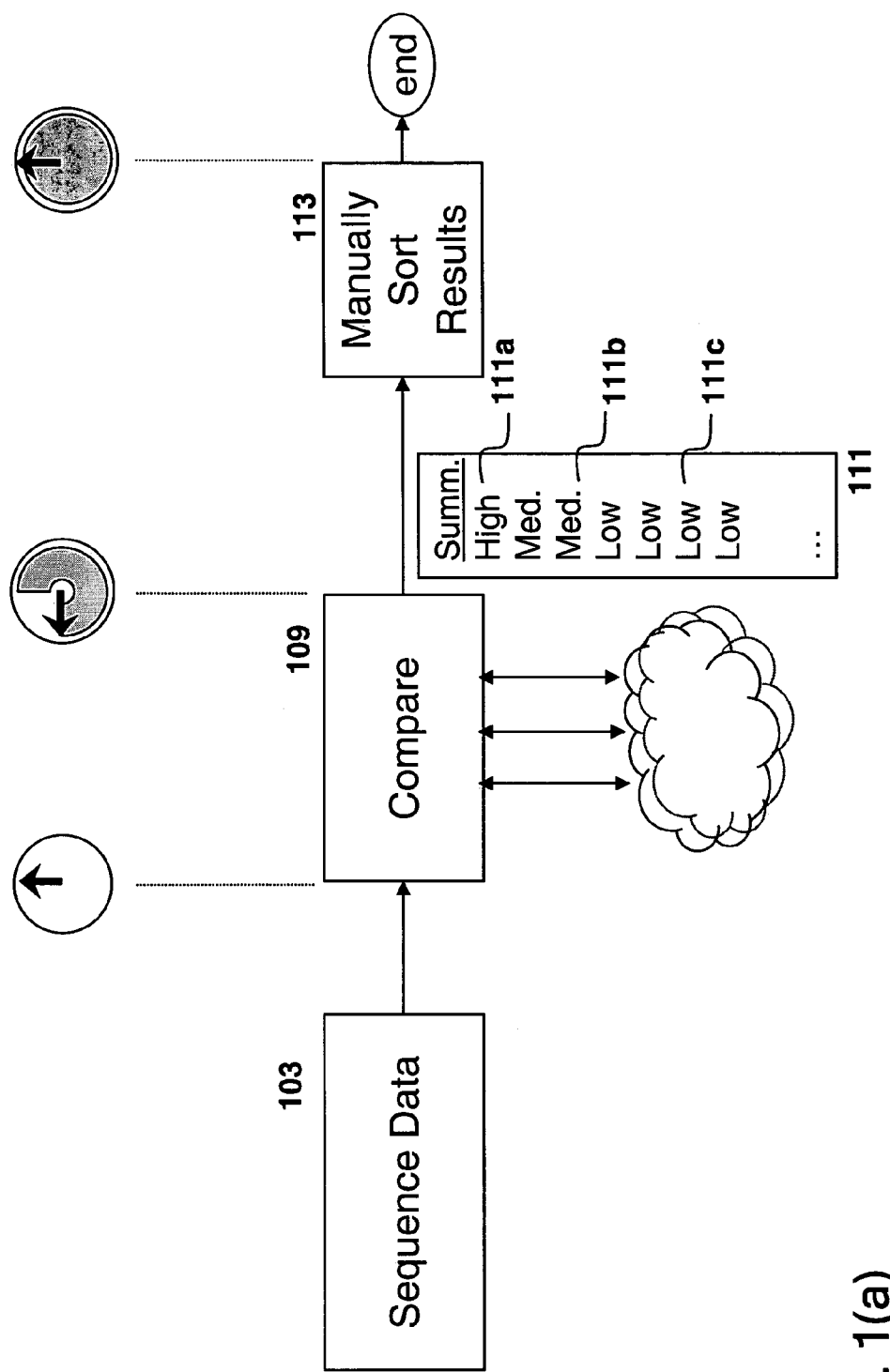
FIG. 1(a) is an exemplary flowchart illustrating the process currently in use by the industry.
Figure 1B:
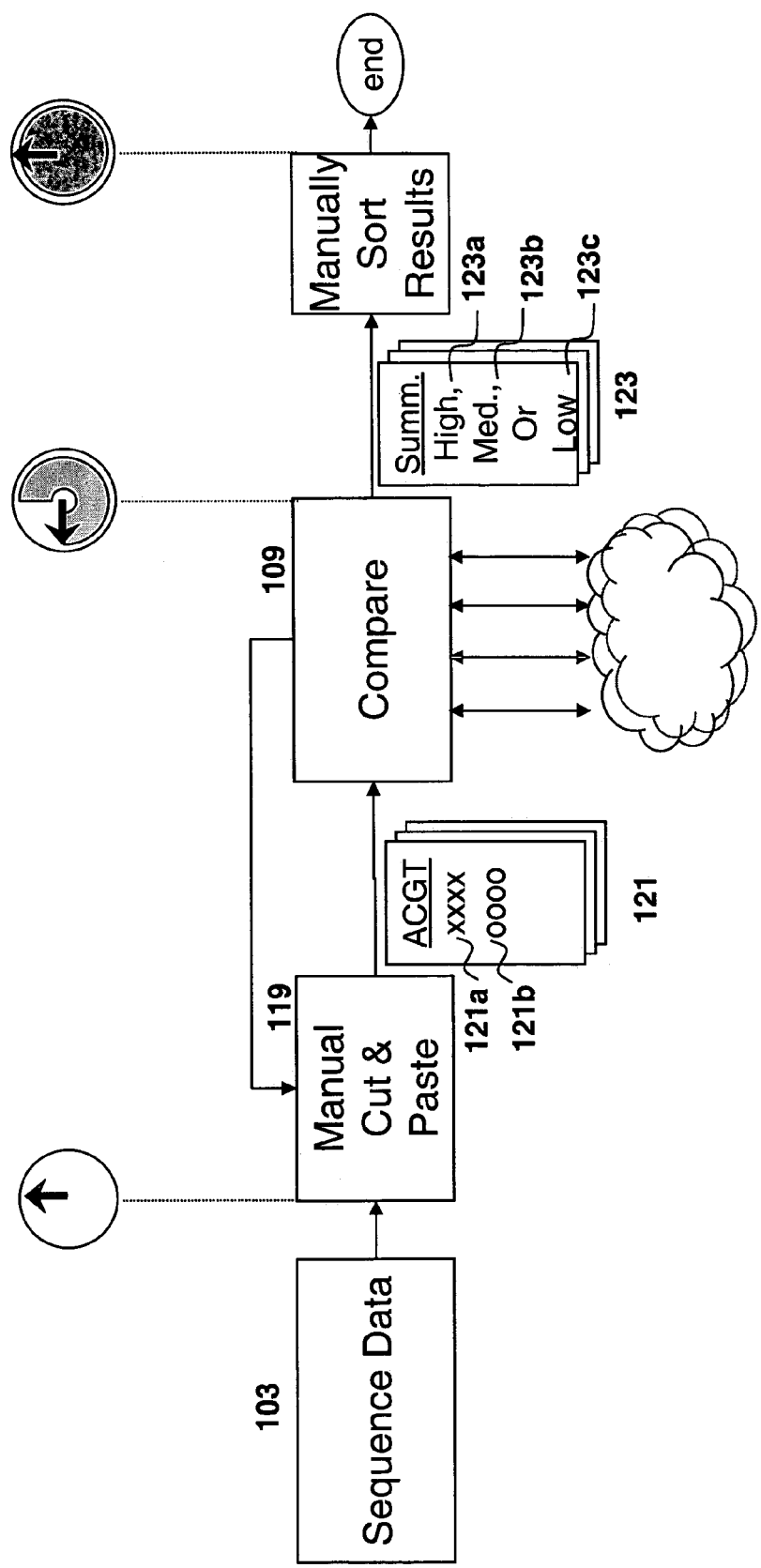
FIG. 1(b) illustrates an alternative case often found in practice in the industry.

Referring now to the drawings, wherein like reference numerals designate identical or corresponding parts throughout the several views. Herein, "meaningful" relates generally to a predetermined level of statistical significance or certainty of a result. Alternatively, meaningful indicates a predetermined level of usefulness to a user for drawing a conclusion regarding the presence of a specific biological entity or group of entities. For example, BLAST returns an E-value (corresponding to a probability), where the product of the E-value with the number of known sequences (probability times opportunities) within the database corresponds to the total number of sequence database records that could return the same similarity value (bit score) for the queried subsequence. If a reshuffling of the submitted test sequence returns the same E-value, the original result was not meaningful. Further, the term "Comparable" used herein refers generally to data that includes a sufficient amount (for example, a system or user-defined threshold number or percentage) of actual base calls (non-Ns) to return meaningful results from a similarity search. Additionally, the term "Comparable" can be used interchangeably with respect to the usefulness of results returned to a user from a similarity search using the data. Conversely, the term "non-Comparable" refers generally to data that includes a sufficient amount (in number or percentage) of non-base calls (Ns) to cause less meaningful or ambiguous results from a similarity search.

The system, including the REPI (Resequencing Pathogen Identifier), is designed to automatically and algorithmically parse an output of a incomplete nucleotide or polypeptide sequences by selecting and editing sequence data into subsequences more suitable for sequence similarity searches. To accomplish this objective, the system includes several functional steps, or filters, to modify the data as little as possible while extracting Comparable data from the sequence data. As described above, due to the nature of the resequencing microarray, the sequences often contain large amounts of non-base calls (Ns). Similarity searches such as BLAST typically return ambiguous results for sequences with a large amount of non-base calls. Examples of ambiguous results include, but are not limited to low bit scores and expect (E) values that do not predict a unique similarity match. Therefore an embodiment of the present system extracts those portions, or subsequences, of original sequences that are most likely to return meaningful results from a similarity search.

Figure 2A:
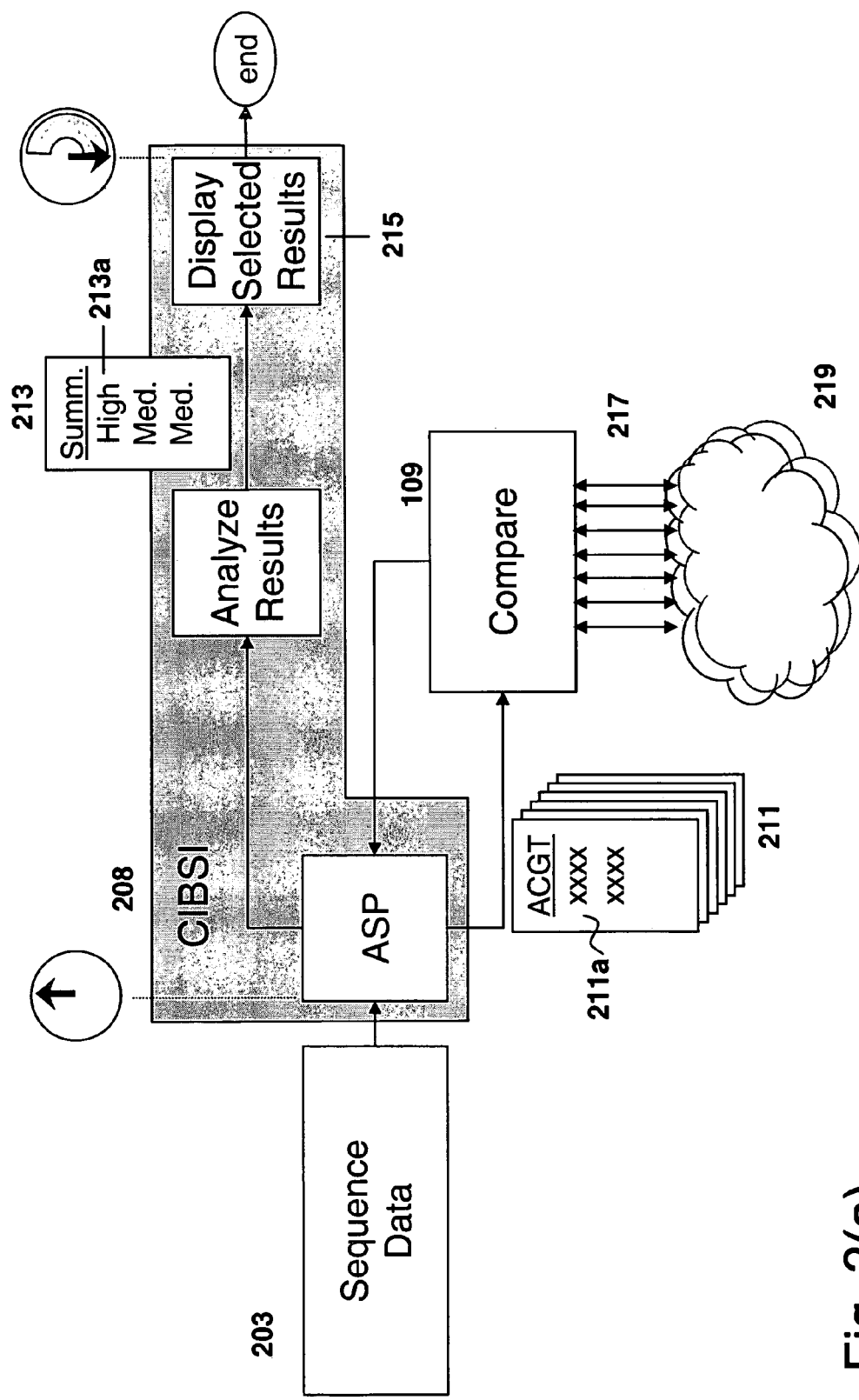
FIG. 2(a) is an exemplary schematic drawing of an embodiment of the system.

FIG. 2(a) is an exemplary schematic drawing of an embodiment of the present invention. Sequence data 203 are first processed by an Automated Subsequence Parsing module (ASP) 209 of the system 208. The ASP 209 filters the sequence data 203 and selects only those subsets which are likely to result in predetermined probability (e.g. a BLAST expect value of <1.0E−9) matches 211a. These subsets are then compared to a sequence database 109 using, for example, a similarity search algorithm, and the results are returned to the system for further analysis and summarization 214. The resulting search summary 213 is then presented to a user for more in depth analysis 215. Because sequence subsets inherently unlikely to return statistically relevant (e.g. a BLAST expect value of $<1.0e^{-9}$) search results are removed by the ASP, the results 213 returned to the user generally include a higher proportion of significant (e.g. a BLAST expect value of $<1.0e^{-9}$) matches 213a than the conventional method of submitting an unparsed sequence. In particular embodiments using a BLAST or BLAST-like similarity search algorithm, expect values between $1.0e^{-150}$ to 2 are preferable. More preferably, expect values are between $1.0e^{-5}$ and 0.5. Even more preferably, embodiments involving BLAST include a bit score and expect value that allows the unique identification of a single pathogen database record. Optionally, the system 208: further filters results in the summary to display only those subsequence matches meeting criteria set by a user or predetermined by the system. These criteria can include but are not limited to: bit score, expect value (chance that another sequence could result in an identical score), or another score derived from the relative positions of subsequences or the microarray signal intensities of regions used to make base calls. Also illustrated in FIG. 2(a) is the enhanced ability of the shared sequence database and comparison resource 109 to provide results to additional users 219 over a network connection 217.

Figure 2B:
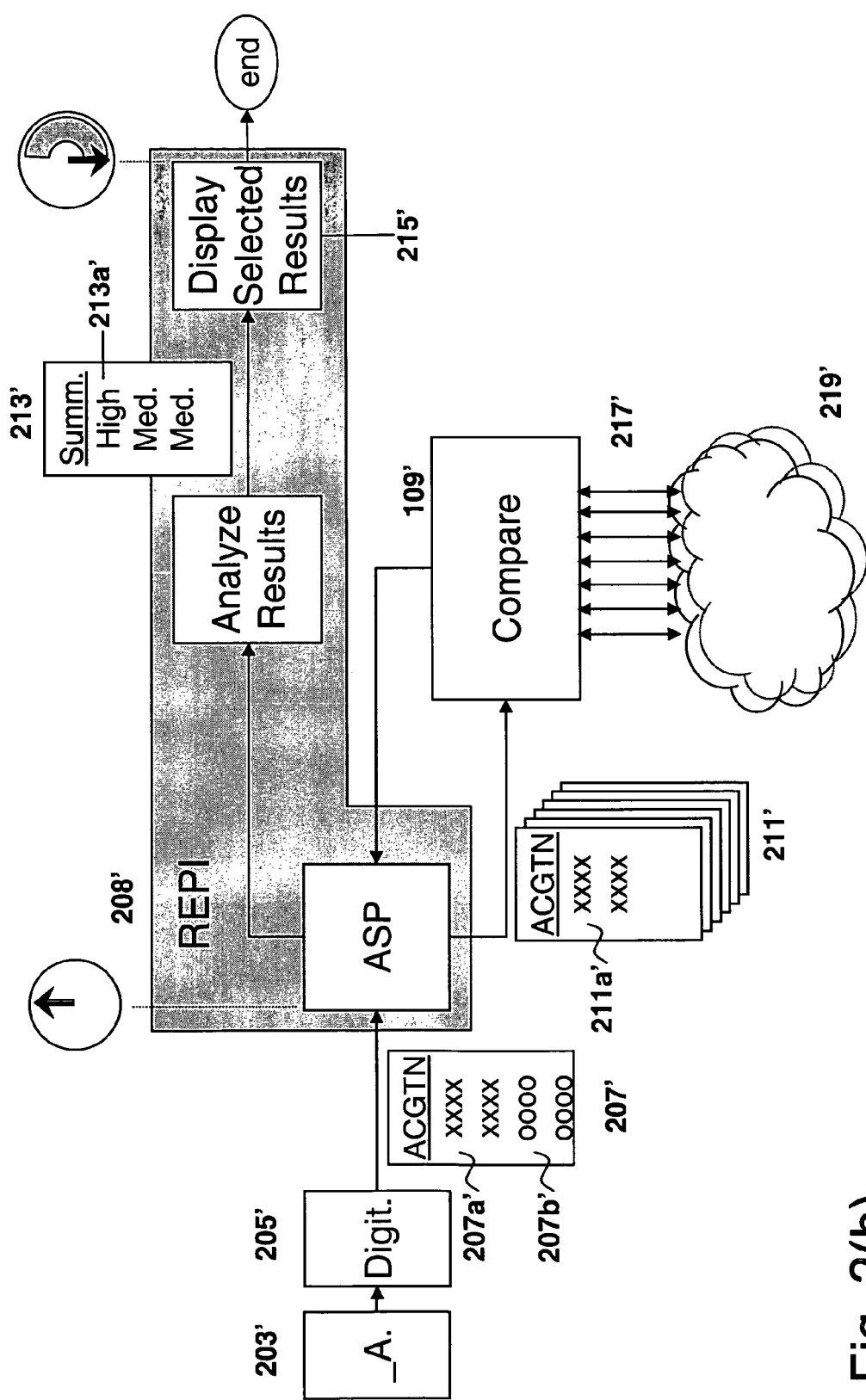
FIG. 2(b) is an exemplary schematic drawing of an embodiment of the Resequencing Pathogen Identifier (REPI)

FIG. 2(b) is an exemplary embodiment of REPI, itself an embodiment of the system. Sequence data 203' are first processed by an Automated Subsequence Parsing module (ASP) 209' of the REPI 208'. The ASP 209' filters the sequence data 203' and selects only those subsets which are likely to result in high probability matches 211a'. These subsets are then compared to a sequence database 109' using a similarity search algorithm, and the results are returned to the REPI for further analysis and summarization 214'. The resulting search summary 213' is then presented to a user for more in depth analysis 215'. As sequence subsets inherently unlikely to return statistically relevant search results are removed by the ASP, the results 213' returned to the user generally include a higher proportion of significant matches 213a' than the conventional method of submitting an unparsed sequence. Optionally, the REPI 208' further filters results in the summary to display only those subsequence matches meeting criteria set by a user or predetermined by the system. Also illustrated in FIG. 2(b) is the enhanced ability of the shared sequence database and comparison resource 109' to provide results to additional users 219' over a network connection 217'.

Figure 2C:
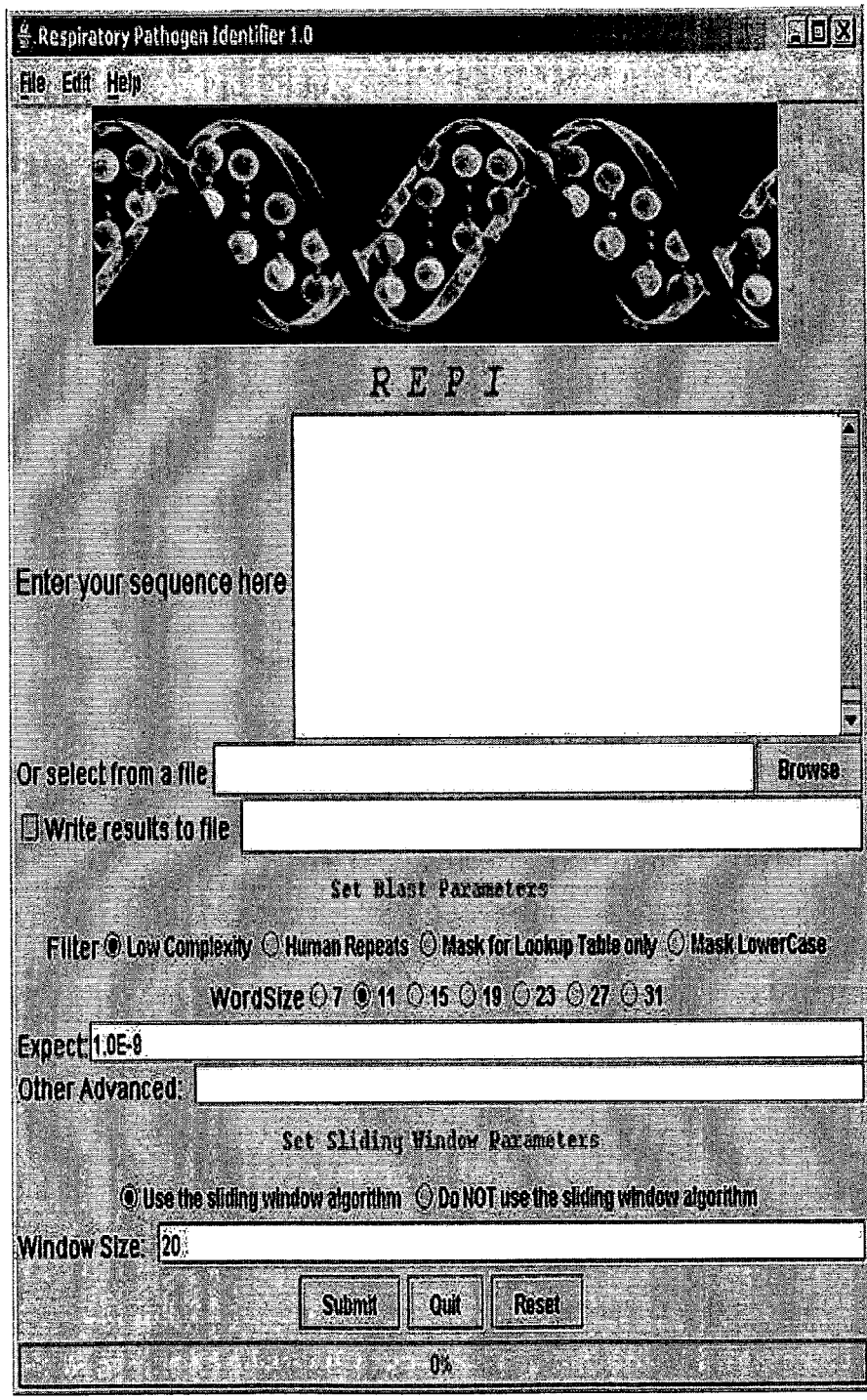
FIG. 2(c) is an exemplary screen shot of an interface for an ASP.

FIG. 2(c) is an exemplary screen shot of an interface (a graphical user interface in this case) for an embodiment of the system in software form. This particular embodiment can interface with network and local BLAST servers (either or both), and enables the modification of several common BLAST parameters 251. Additionally, as described in more detail below, parameters specific to the parsing algorithm 253, such as the window size, are optionally made available to a user.

Figure 3:
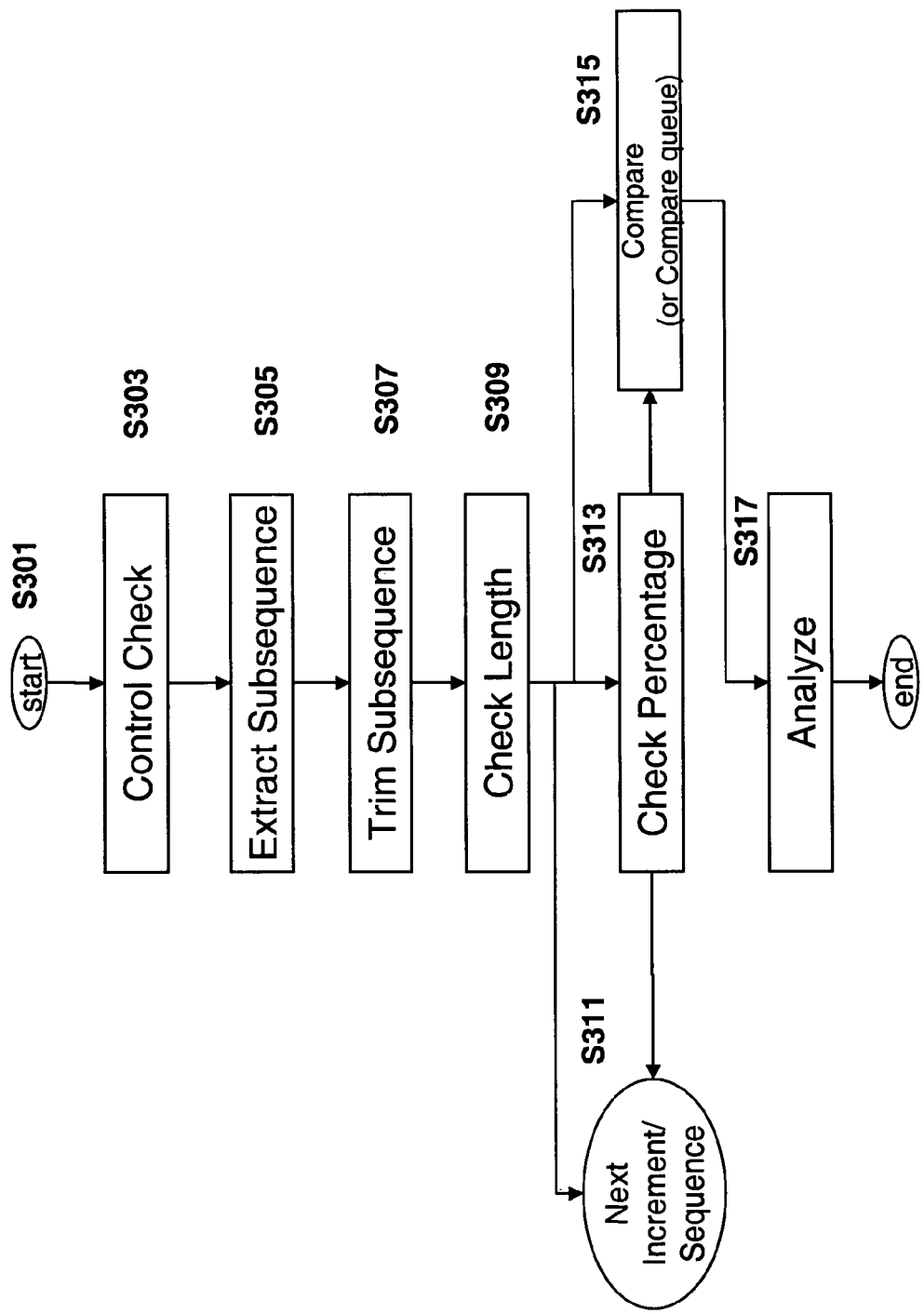
FIG. 3 is a flowchart describing the general functionality of the ASP.

FIG. 3 is a flowchart describing the general functionality of the CIBSI, including the ASP. The CIBSI receives "raw" sequence data at the start of the operation S301. REPI may receive sequence data in a variety of formats, including but not limited to FASTA, MSF, GCG, Clustal, BLC, PIR, MSP, PFAM, POSTAL, and JNET. In the case of conventional and resequencing microarrays, the sequence data typically takes the form of multiple sequences of base calls corresponding to multiple tiled regions of the microarray in FASTA format.

In addition to its flexibility with respect to sequence data formats, the system accepts sequence data from a variety of different source types. As described above, these types include, but are not limited to, manual or automated Sanger sequencing, shotgun sequencing, conventional microarrays, resequencing microarrays, microelectrophoretic sequencing, sequencing by hybridization (SBH), Edman degradation and variants thereof, Cyclic-array sequencing on amplified molecules, Cyclic-array sequencing on single molecules, and non-cyclical, single-molecule, real-time methods such as nanopore sequencing. Alternatively, the raw sequence S301 can be comprised of transcript nucleic acids (messenger ribonucleic acid (mRNA) or intermediate phase sequences used for viral transcription and translation. For example, in an embodiment of the invention directed towards RNA transcripts, RNA can either be hybridized directly to an array after it is fragmented (as done with Affymetrix gene expression arrays) or converted to DNA using reverse transcriptase. Tile regions are constructed from exon (protein coding sequences) regions of the genome and a resequencing array is used to analyze which of the sequences made it into transcripts. In alternative embodiments, the process described in FIG. 3 corresponds to amino acid sequences, where the set of raw sequence(s) S301 may represent direct reads of amino acids or sequences inferred from amino acid compositions as measured by high-resolution mass spectrometry. Optionally, raw amino acid or protein data in which relative position is not conserved is analyzed to include relative position data.

Figure 24:
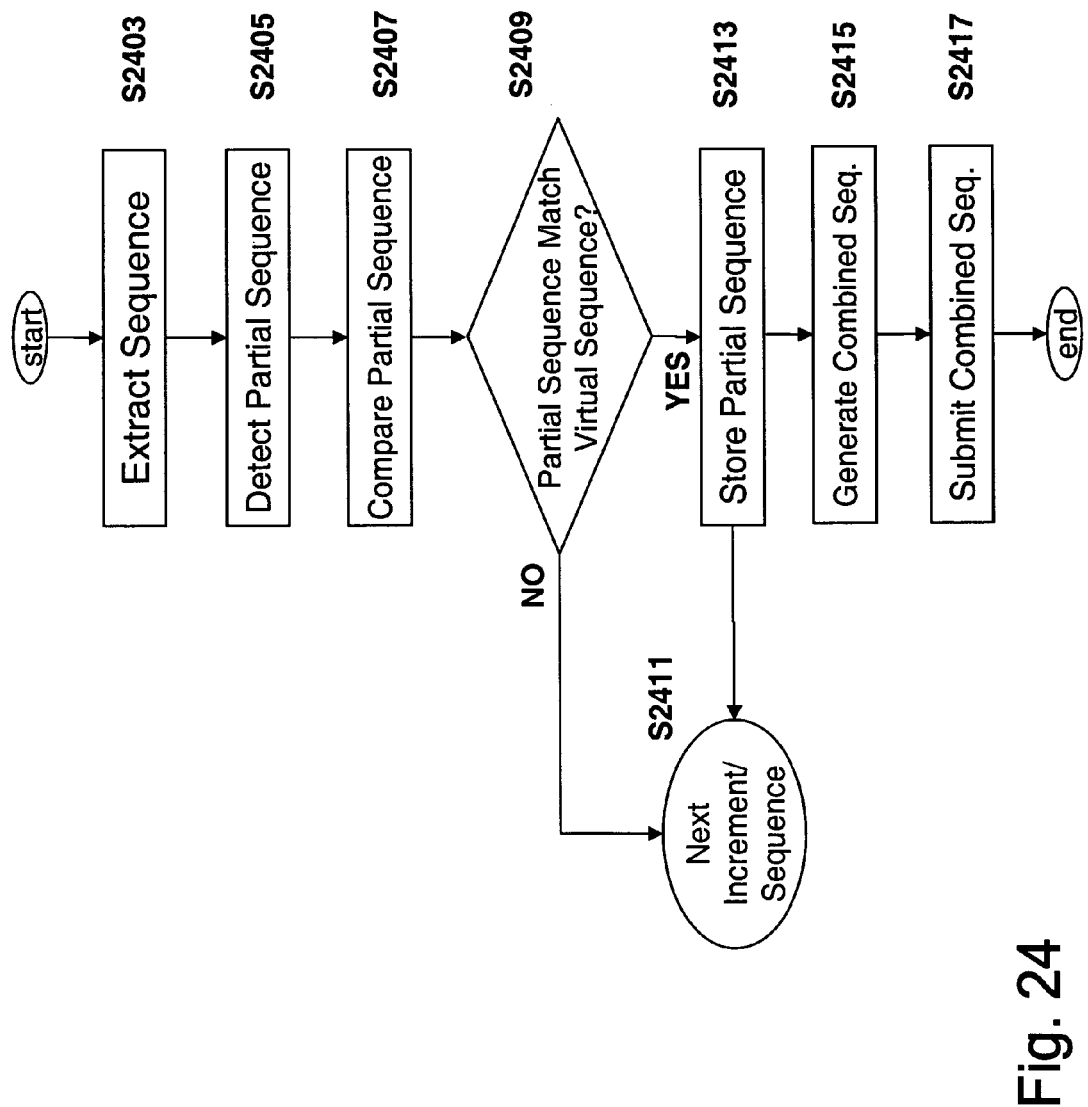
FIG. 24 is an exemplary flowchart for formatting resequencing array data according to an embodiment of the present invention.

In a resequencing microarray, the structure of the overall gene sequence is suggested by the position of the partial sequences within the overall structure of the resequencing tile. For example, the resequencing array may only give reads of 5-10 consecutive base calls at a time, each of which are separated by a consecutive series of Ns. FIG. 24 depicts a more general description of this concept that is applicable to any collection of partial sequence reads. Thus, any collection of nucleotide base calls or amino acid sequences which have no apparent relationship to one another can first be compared to a "Virtual Sequence" against which the shorter detected sequences are compared. The consecutive base calls, or partial sequences, are then related as individual portions of a collective sequence. Thus, in order for the partial sequence data from the microarray or any other sequence generation platform to be more effectively and efficiently processed by the CIBSI, the partial sequences are first assembled into a collective arrangement, or composite sequence. To determine which partial sequences should be combined and submitted, each detected subsequence is compared using a similarity search with a group of reference sequences stored in memory. The partial sequences that result satisfactory matches when compared against one of the reference sequences are then stored as part of a composite sequence to be submitted the CIBSI for analysis.

The process for formatting the sequence data extracted from a resequencing microarray is depicted in the flowchart shown in FIG. 24. The sequence information is extracted from the resequencing microarray or any other nucleotide or polypeptide sequencing platform S2403, and processed to detect partial sequences separated by a consecutive series of Ns S2405. The step of detecting the partial sequences may be carried out by a windowing function which initiates a viewing window upon the detection of a base call and ends the viewing window when another series of Ns are detected. Thus a window is created around the partial sequence data, and the Ns separating the partial sequence reads are trimmed away. A scanning operation may also be performed on the sequence data that identifies each consecutive series of Ns, thereby indicating the groups of base-calls corresponding to the partial sequences.

Each identified partial sequence is then compared against a stored reference sequence S2409 to determine whether the partial sequence corresponds to one of the stored reference sequences. This comparison will yield a statistical value indicating the similarity between the stored reference sequence and the partial sequence. Then, if the statistical value is beyond a predetermined threshold, the partial sequence is stored S2413 to be combined with other partial sequences SS2415. Alternatively, if the statistical value is below a predetermined threshold, the partial sequence is discarded. This process continues until all the partial sequences are compared, thus generating a composite set of data to be submitted to the CIBSI, as discussed below.

The system then performs a Control Check S303 before extracting a candidate subsequence S305. After extraction of a candidate subsequence, the system then trims the non-calls (Ns) from the beginning and end of the candidate subsequence S307. Then the system checks the length of the trimmed candidate subsequence S309 to determine whether an alternative sequence or subsequence should be selected S311, the candidate subsequence is ready to go to a similarity search server or be added to a similarity search queue S315, or whether an additional check of the percentage or proper base calls in the subsequence meets an acceptable threshold for sending it to be compared (using a similarity search). The selection of an alternative sequence or subsequence S311 is accomplished in one embodiment through the use of a sliding window algorithm. For those sequences that are sent to be compared S315, the system gathers the results returned from the similarity search server, performs statistical analysis on these results and filters them for the user according to user preferences S317. Optionally, the system can simply return similarity search results for the submitted subsequences. Also, as will be made more evident given the exemplary embodiments described below, the steps of the algorithm can be rearranged or modified in alternative embodiments. Further, as also described in more detail below, the behavior of the system is predetermined by the system or optionally defined by the user.

The following paragraphs describe each of the main functional steps shown in FIG. 3 in more detail.

Figure 4:
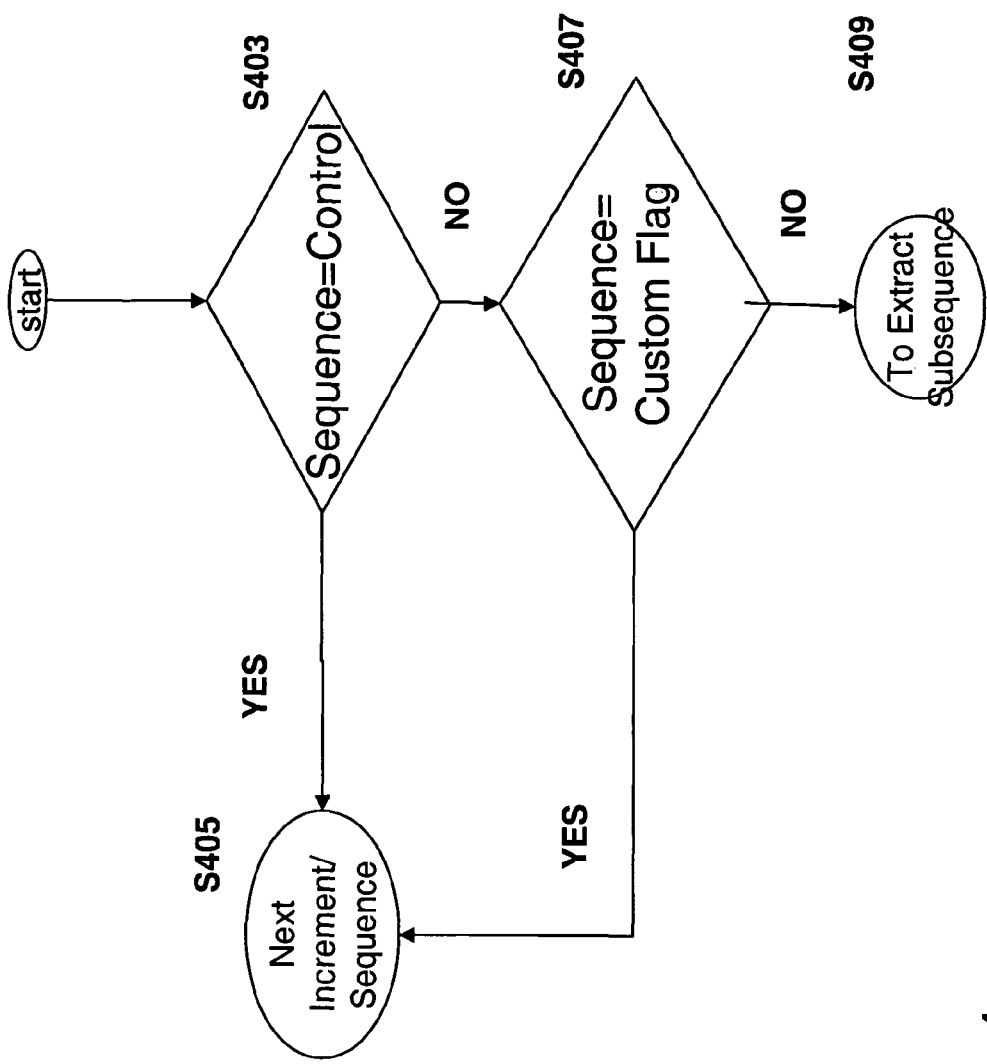
FIG. 4 is an exemplary flowchart of a control check step.

FIG. 4 is an exemplary flowchart of a control check module for performing the Control Check step S303. Here, a sequence is first checked to see if it is a control sequence often outputted by microarrays S403 that do not correspond to a biological sample, but instead confirm that the microarray is functioning properly. The control sequence incorporated into the microarray is specifically designed to be a nonsense, uniquely identifiable, or non-naturally occurring sequence; therefore, by default, a control sequence will not return a significant similarity. If a sequence is not a control, the system may optionally check if the sequence matches an alternative custom parameter flag S407 before continuing on to the next step S409. In the case that the sequence is recognized as either a control or matching a custom parameter, the system optionally performs a supplementary function corresponding to the custom parameter or moves onto the next sequence S405.

Figure 5:
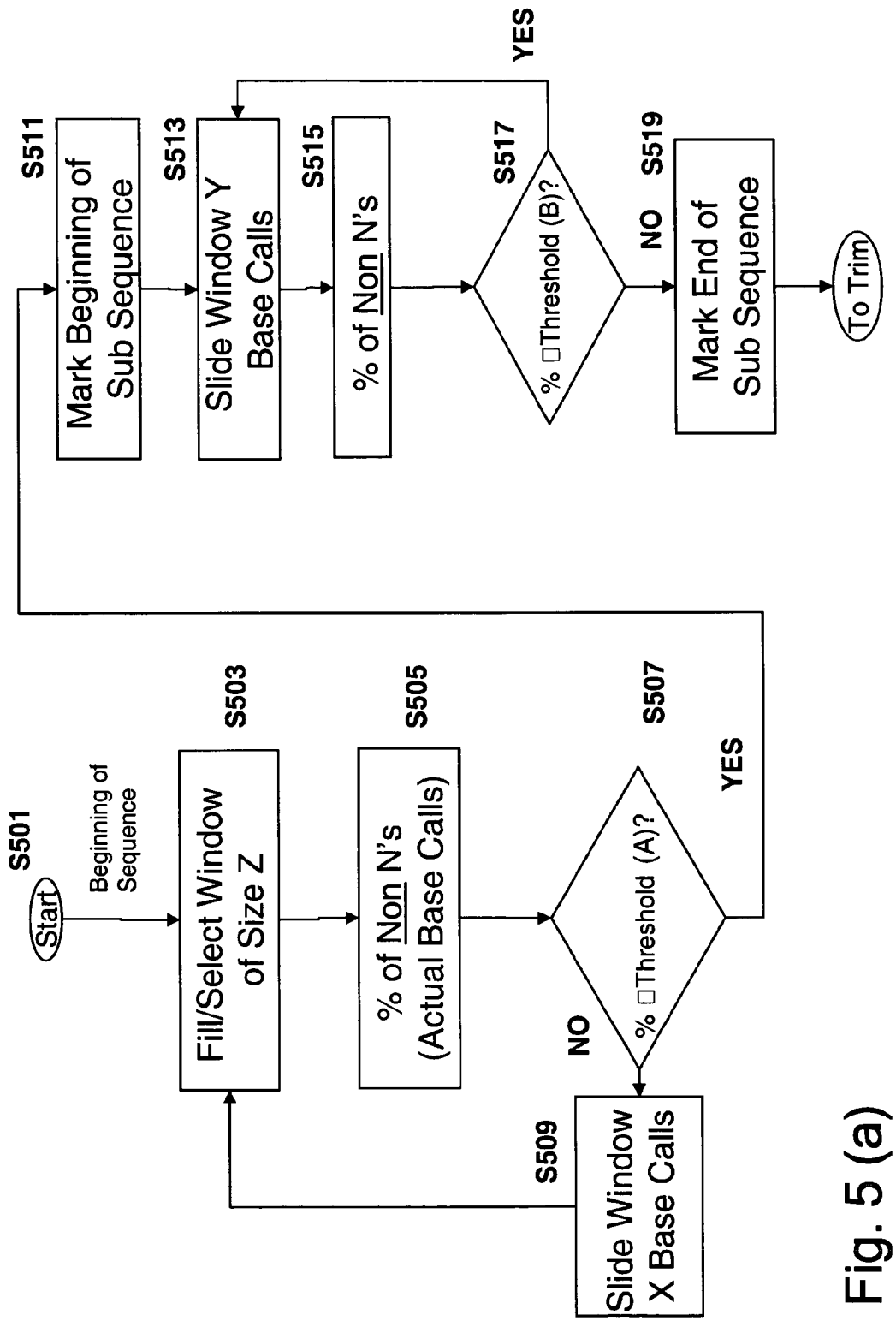
FIG. 5(a) is an exemplary flowchart of the extract subsequence step.
FIG. 5(b) is an example of a sliding window according to one embodiment of the system (SEQ ID NO.8)
Figure 5:
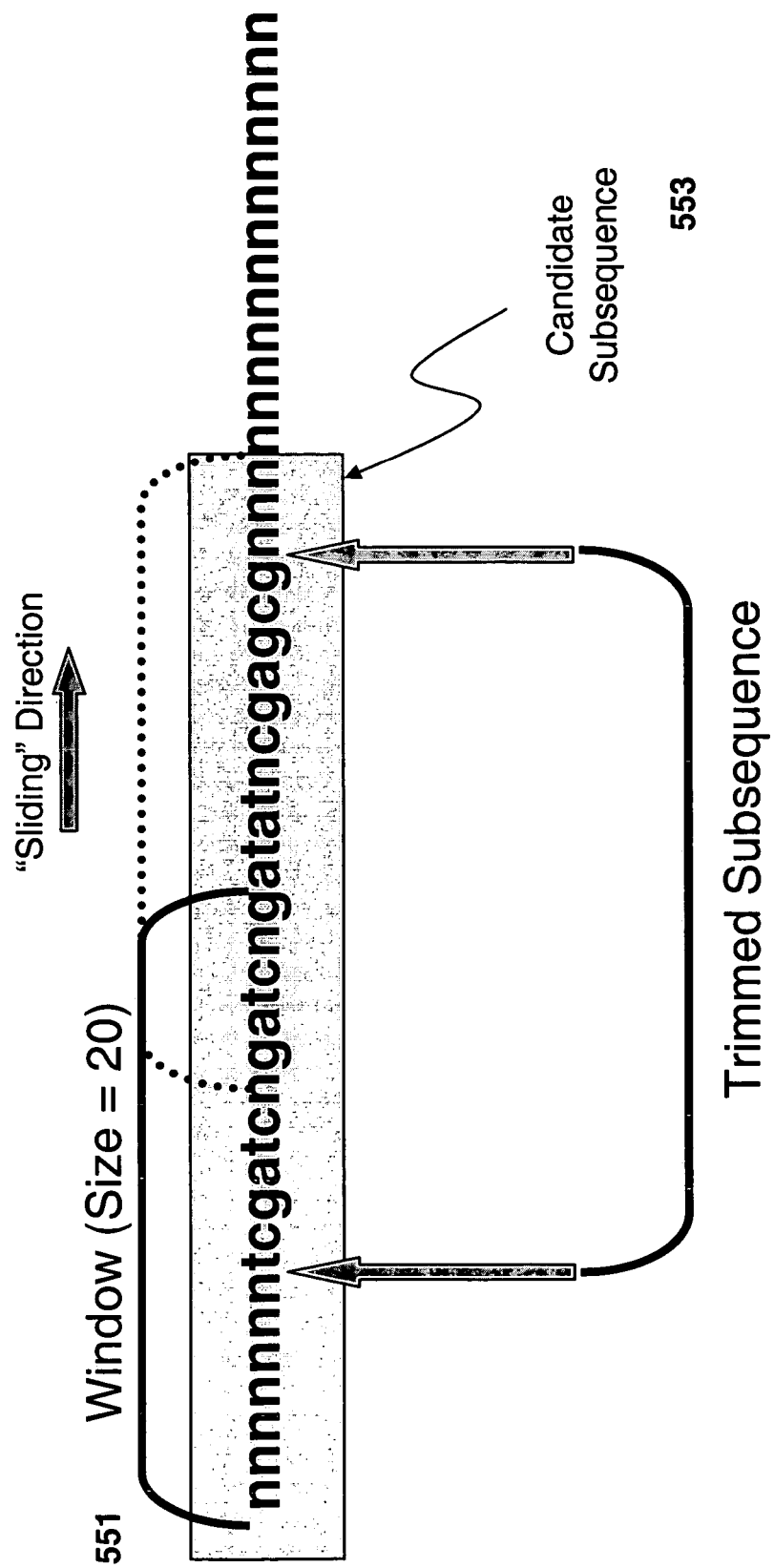

FIG. 5 is an exemplary flowchart of the extract subsequence step S305. Having preliminary selected a sequence S501, the system views the sequence within the context of a window of size Z S503, where Z is a Window Size parameter corresponding to a number of returned base calls. This "viewing window" is typically smaller in length than the size of a typical sequence and can begin at any point in the sequence. Then the system calculates a percentage of actual base calls (non-Ns) contained within the window S505. In the illustrated example, the calculation is performed by associating a "1" with valid bases and a "0" with all Ns. In one embodiment, the window size Z can be selected from a range preferably between two base calls and half the length of the smallest target or input sequence. As the window size Z increases, the module becomes more permissive with respect to selecting candidate subsequences including more non-base calls.

The calculated percentage is then compared to a First Jump Threshold parameter, A (for example, 25%), which can either be predetermined by the system or selected by a user S507. If the calculated percentage of actual base calls within the window does not satisfy the criteria defined by the First Jump Threshold, A, the system advances the window a number of base calls S509 according to a First Window Jump parameter, X, that may also be predetermined by the system or selected by the user, but is preferably between one and Z, the Window Size parameter. Advancement of the window at this or any other point can occur in any direction (for example, towards the end of the sequence). In the case of the calculated percentage of actual base calls within the window satisfies the criteria defined by the First Jump Threshold A, the system marks the beginning of a candidate subsequence S511 at the beginning of the sliding window. The window is then moved incrementally a number of base calls S513 according to a Second Window Jump parameter, Y, and at each slide increment, the percentage of actual base calls within the window is calculated S515. If the calculated percentage of actual base calls within the candidate subsequence fails to meet the criteria set by a Second Jump Threshold B, the system marks the end of the candidate subsequence at the base call of the sequence corresponding to the base call at the end of the window S519. For each sequence, the system searches for the largest continuous string(s) of usable data. As the Window Jump parameters X and Y increase, the module becomes more permissive with respect to selecting candidate subsequences with a greater number of non-base calls. As the Jump Thresholds A and B increase ceteris paribus, the module becomes less permissive.

FIG. 5(b) is an example of a sliding window algorithm according to an embodiment of the present invention. The beginning and end positions of the sliding window 551 determine the length and contents of the candidate subsequence 553. This subsequence is then trimmed in a Trim function described below.

Figure 6:
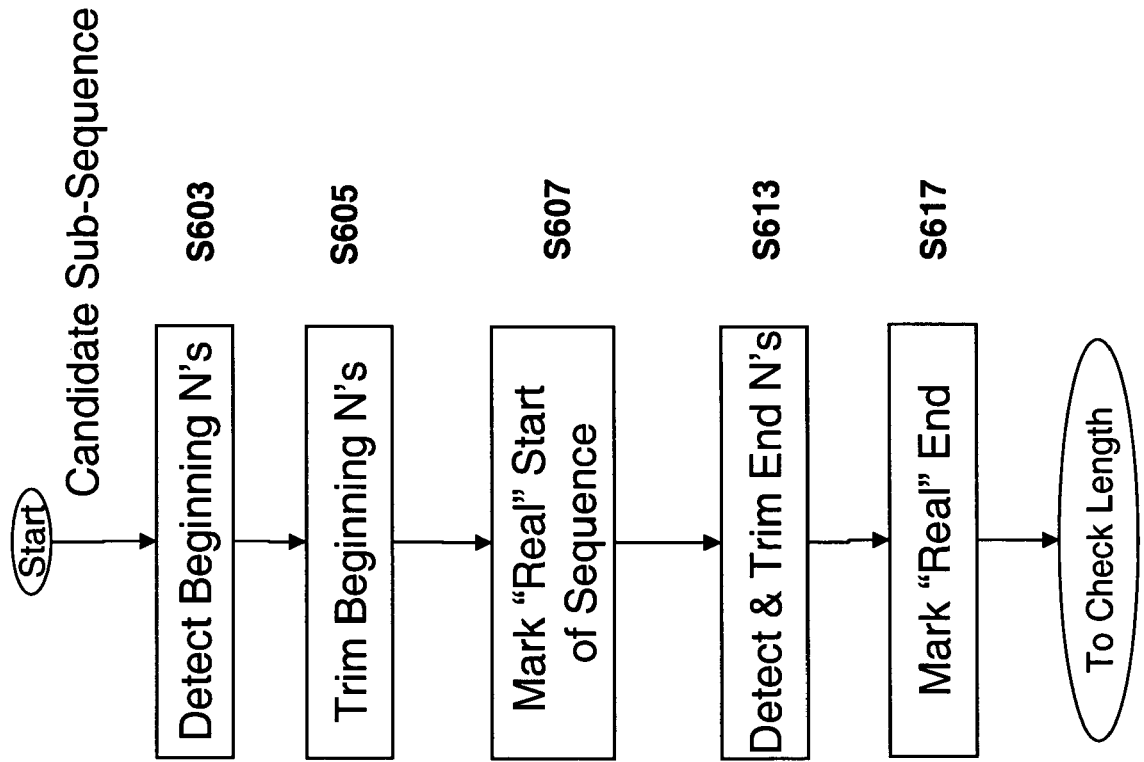
FIG. 6 is an exemplary flowchart describing in more detail a trim function performed by the system.

FIG. 6 is an exemplary flowchart describing in more detail the Trim function S307 performed by the system. In this particular functional module, the system detects the beginning Ns of a candidate subsequence S603 and subsequently trims the beginning Ns from the candidate subsequence S605. The system then recognizes that the actual start of the candidate subsequence has changed S607 and adjusts the location and contents of the candidate subsequence accordingly. A similar set of actions is performed to remove the Ns at the end of the candidate subsequence S613, S617. Trimming increases optimality of the algorithm since the sliding window method described herein allows for sequences to begin and end with Ns. Alternatively, the sliding window function can be adapted or replaced to detect and avoid Ns and the beginning and/or end of a candidate subsequence, thus obviating the need for this step.

Figure 7:
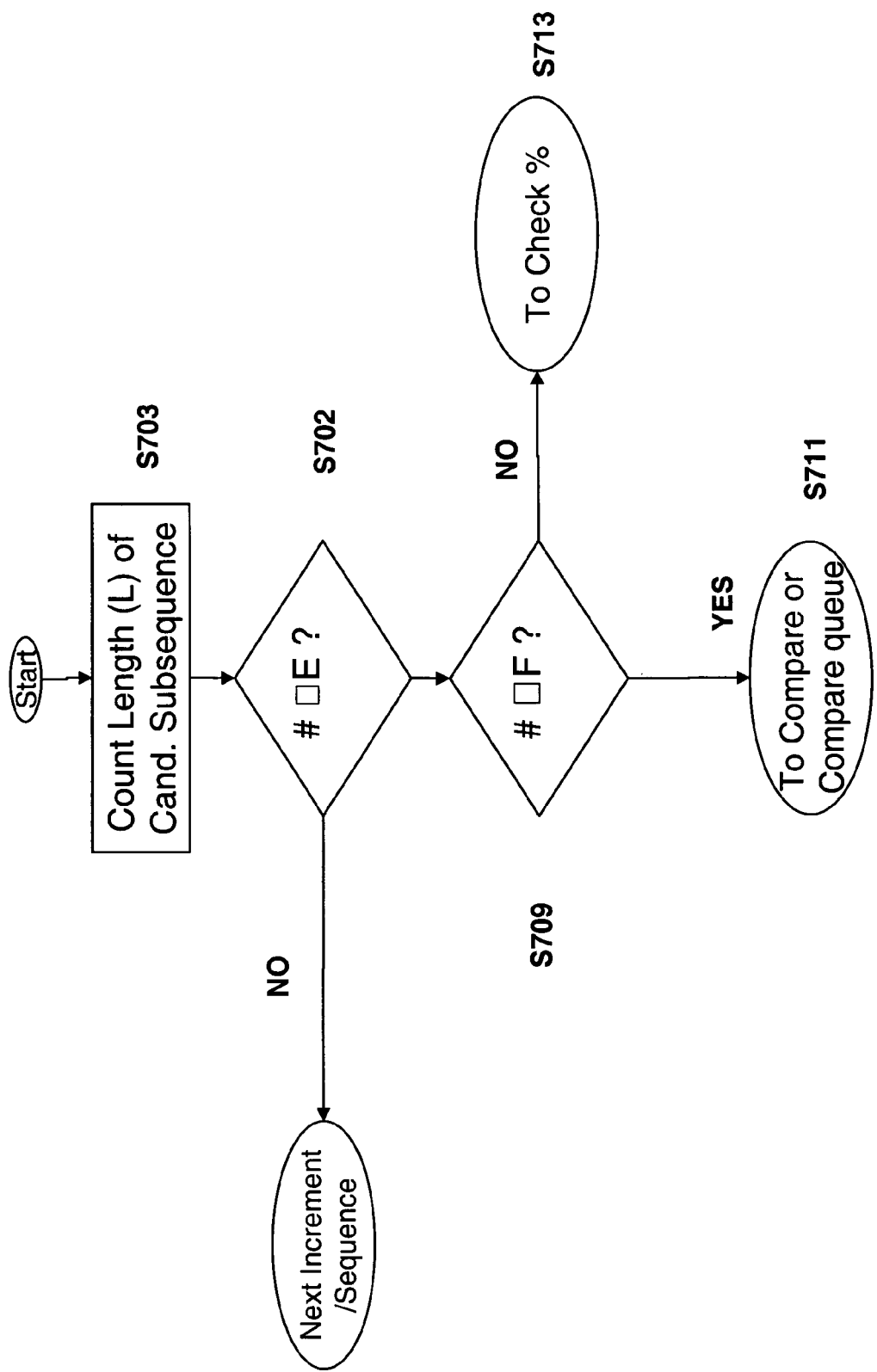
FIG. 7 shows an exemplary flowchart detailing actions in the Check Length step.

The next function of the system is a length evaluation S309. FIG. 7 shows an exemplary flowchart detailing a method for performing the Check Length step S309. The length of the candidate subsequence is calculated S703 and compared against a First Length Threshold parameter, E S705. If the length of the candidate subsequence is not greater than E (for example, 20 nucleotides), the system returns to the extract subsequence step S305. If the First Length Threshold parameter E is met, the length of the candidate subsequence is compared against a Second Length Threshold parameter, F (for example, 50 nucleotides) S709. If the length of the candidate subsequence exceeds F, the candidate subsequence is sent to the similarity search (comparison) server or added to a queue S711 for batch processing of selected subsequences by the server. In the case that the candidate subsequence exceeds E but does not exceed F, the system moves on to the step of checking the percentage of actual base calls within this intermediate-length (for example, a subsequence with a length between 20 and 50 nucleotides) candidate subsequence S713. The First and Second Length Threshold parameters E and F can vary over a range as wide as the greatest searchable subsequence. Further, the module becomes more permissive as E and F decrease.

Figure 8:
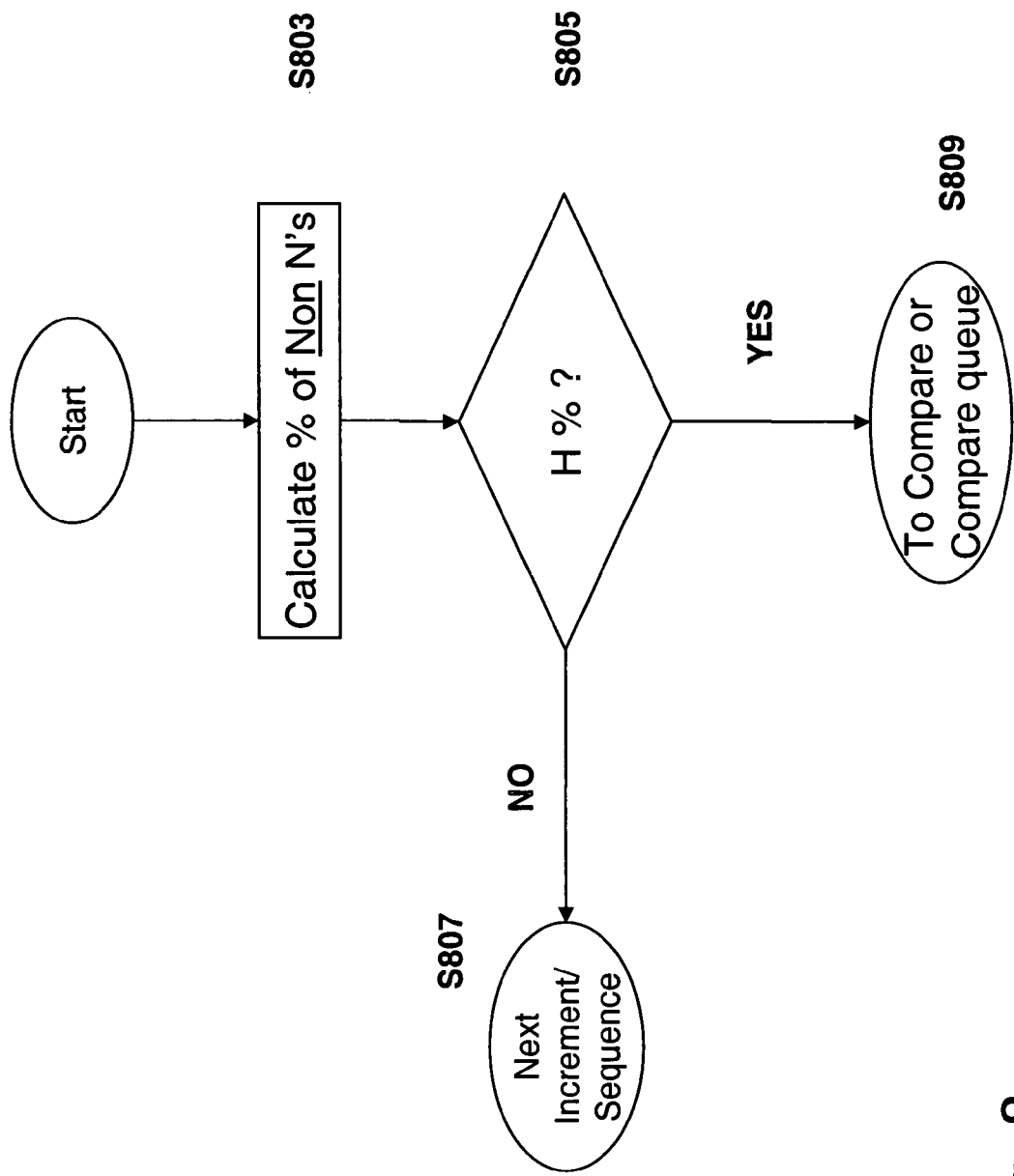
FIG. 8 shows an exemplary flowchart of the Calculate Percentage step.

FIG. 8 shows an exemplary flowchart of the Calculate Percentage function S313. Within this function, a percentage of actual base calls is calculated for an intermediate-length candidate subsequence S803. This calculated percentage is compared S805 against an Intermediate Percentage Threshold, H, which is selected by the user or predetermined by the system. If the calculated percentage of actual base calls is less than the Intermediate Percentage Threshold parameter, H (for example, 60%), the system returns S807 to the Extract Subsequence step to search for an alternative candidate subsequence. If the calculated percentage exceeds H, the intermediate-length candidate subsequence is sent to either the queue for batch processing of subsequences or sent to the similarity search server immediately S809. As the Intermediate Percentage Score Threshold parameter increases, the module becomes less permissive of subsequences with larger amounts of non-base calls.

Figure 9A:
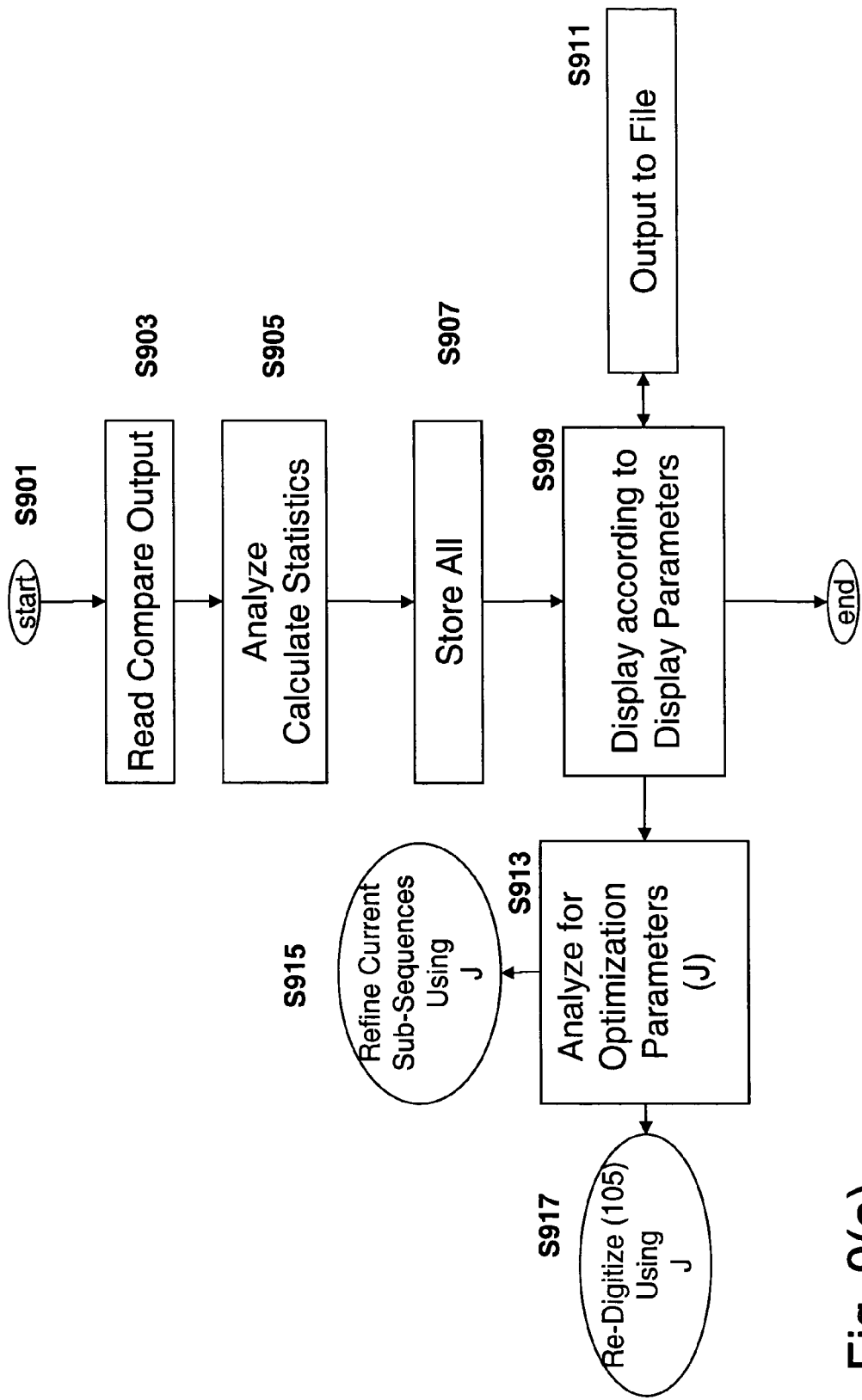
FIG. 9(a) is an exemplary flowchart describing in more detail the actions of the system within the Analyze Step.

In addition to receiving results from the similarity search regarding submitted subsequences, the system optionally provides further analysis of the submitted subsequences. FIG. 9(a) is an exemplary flowchart describing in more detail the actions of the system within module S317 of FIG. 3. This module begins after a subsequence or group of subsequences has been compared S901. At this point, the system reads the similarity search output S903 and analyzes the output, and calculates additional descriptive statistics regarding submitted subsequences that are selected by the user or predetermined by the system S905.

The analysis performed and statistics calculated by the system include, but are not limited to, the selected subsequence length as a percentage of the sequence and the subsequence length in base calls, which together can be used to indicate what portion of the target biological entity gene was identified. The subsequence length and percentage of subsequence base calls allow a researcher to monitor the system's algorithms and functional steps. Further, in the case of resequencing microarrays, threshold parameters for base calling algorithms including, but not limited to, GDAS, can be monitored. In an alternative embodiment, the system accepts and also formats statistical results returned from the similarity search, allowing the user to manipulate and organize results using a provided graphical user interface. FIG. 9(b) is an example of output results data according to an embodiment of the present invention.

Optionally, the system can store all of the outputs returned by a similarity search and analysis described above S907, including, for example, BLAST results. The system also optionally displays S909 all of the results or a subset of the results returned by a similarity search and/or calculated by this system to the user. Certain embodiments of the present invention then allow these results to be sent and saved for archiving or transfer S911.

The following table illustrates exemplary ranges and preferable subranges for several exemplary parameters and thresholds described above.

Preferred subranges:

TABLE 1

| Parameter/Threshold | | Start Value | Subrange 1 | Subrange 2 |
| --- | --- | --- | --- | --- |
| Expect Value Threshold | | 1.0E−9 | 1.0E−8-1.0E−10 | 1.0E−7-1.0E−11 |
| Window Size | Z | 20 | 10-30 | 1-* |
| First Jump Threshold | A | 25% | 15%-35% | 1%-99% |
| First Window Jump | X | 1 | 1-5 | 1-* |
| Second Window Jump | Y | 1 | 1-5 | 1-* |
| Second Jump Threshold | B | 25% | 15%-35% | 1%-99% |
| First Length Threshold | E | 20 | 10-30 | 1-* |
| Second Length Threshold | F | 50 | 40-60 | 1-* |
| Interm. Percentage Threshold | H | 60% | 50%-70% | 1%-99% |

*constrained by system parameters such as random access memory (RAM), processor speed, etc.

In yet another embodiment of the system, the search (comparison) output can be analyzed for Optimization Parameters, J, S913. As described above, Parameters and Thresholds of the system, including but not limited to A, B, X, Y, E, F, and H, are set by the user or predetermined by the system. Alternatively, an embodiment of the system enables the optimization of one or several of these variables by the system itself or through the use of a complementary functional module. For example, optimization of a Parameter or Threshold could be performed in accordance with well-known optimization (for example, SIMPLEX linear programming) or Artificial Intelligence (including state space search methods such as uniform or heuristic search) techniques by analyzing system performance recorded over the course of multiple uses or "passes" of system operation. Corresponding Optimization parameters, J, can be used, for example, to automatically alter the various parameters and thresholds used in the previous steps and run the process again using these new optimized parameters S917. Alternatively, instead of starting again from the raw data file, the Optimization Parameter J can be used to refine output of selected subsequences S915 by using the Optimization Parameters J to alter parameters related to, for example, the behavior or function of a similarity search algorithm used in conjunction with the system. The Optimization Parameters can be adjusted by a user or the system itself to enhance system performance with respect to, for example, speed or relevant/meaningful similarity search results.

Figure 10:
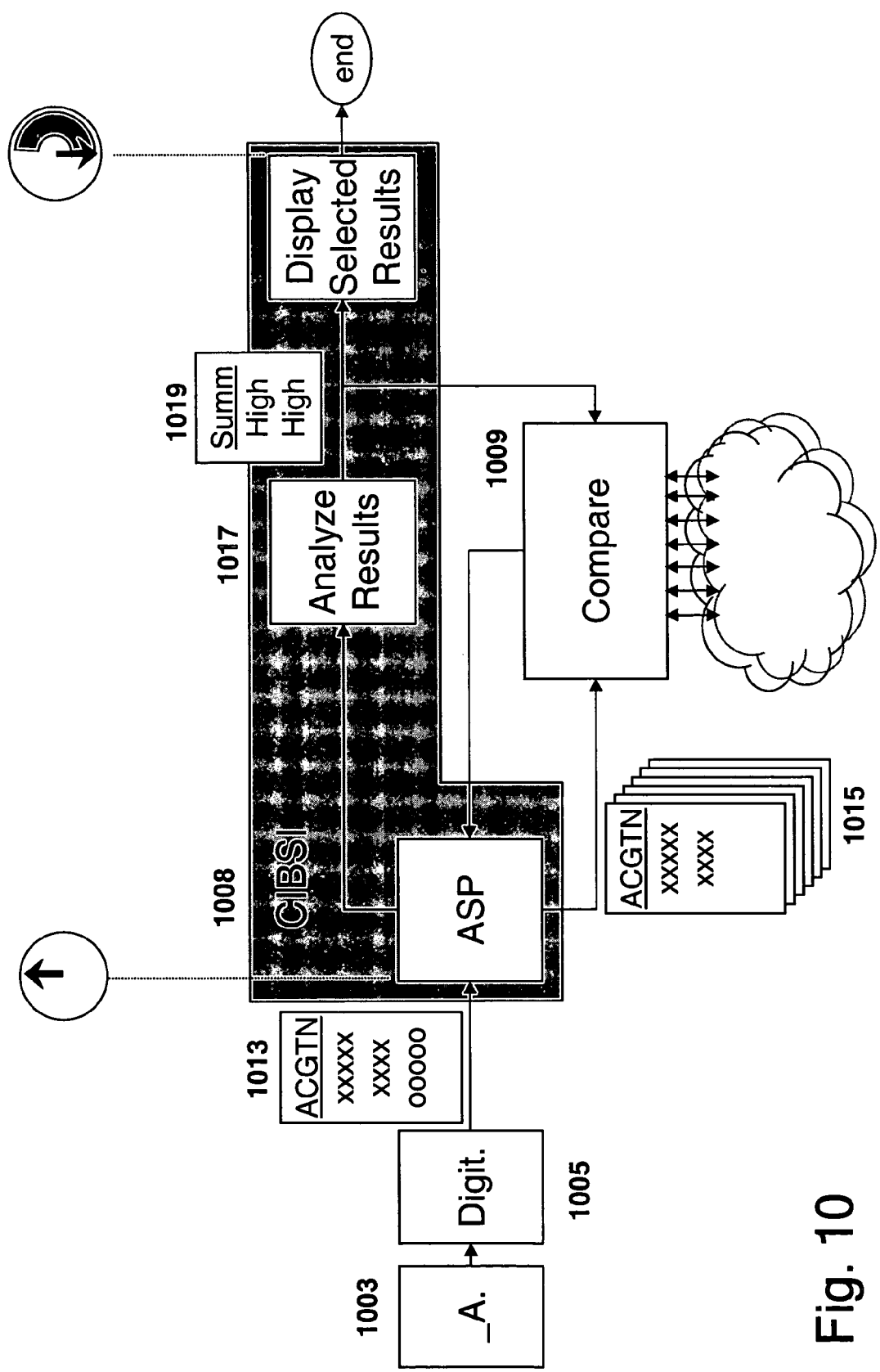
FIG. 10 is an exemplary flowchart describing an additional embodiment of the system.
Figure 11:
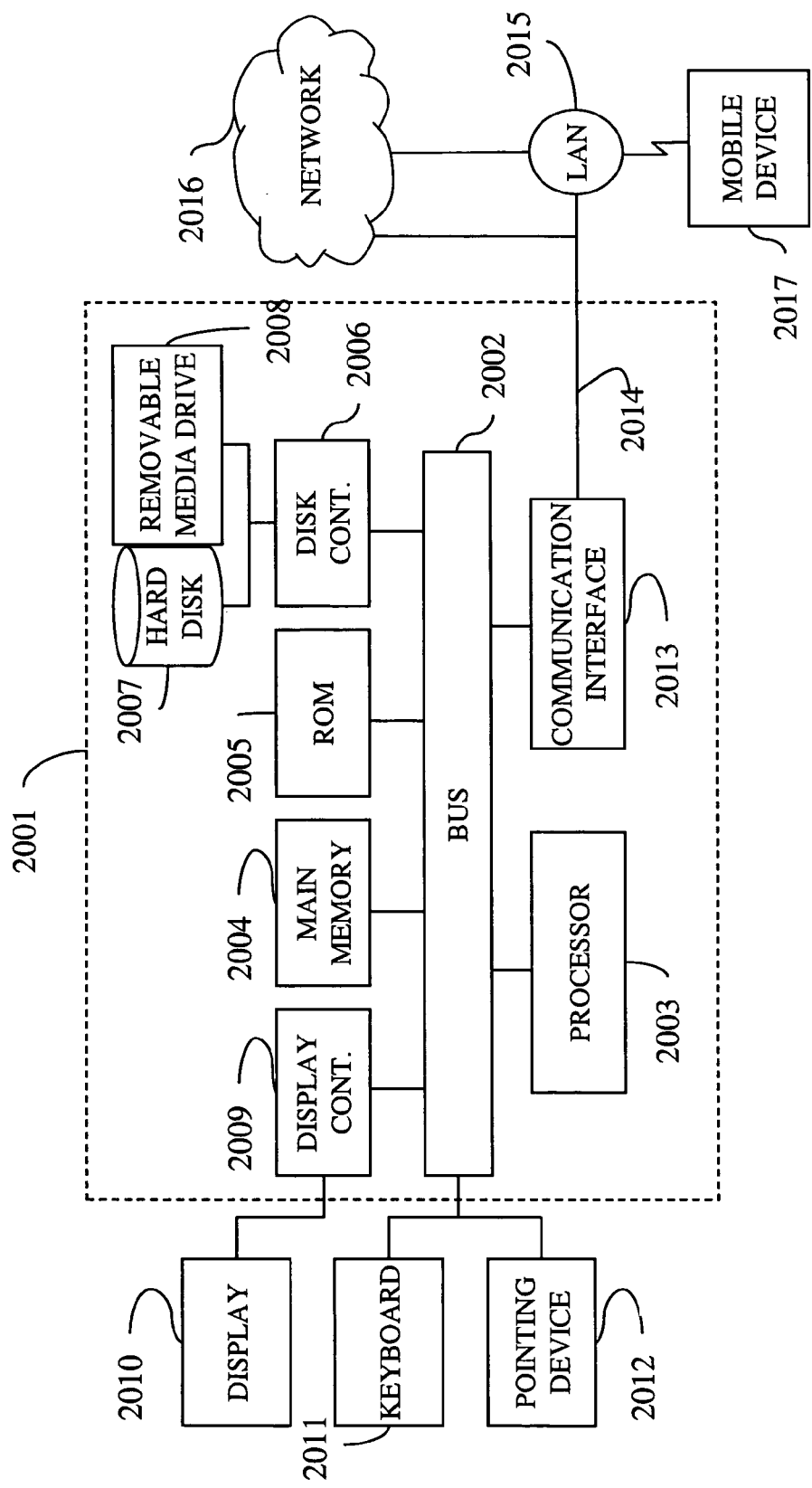
FIG. 11 is a block diagram of a computer system (or server) upon which an embodiment of the present invention may be implemented.

FIG. 10 is an exemplary flowchart describing yet another embodiment of the present invention that utilizes its extensible, kernel-like nature. In particular, the system analysis 1017 is used to optimize or otherwise alter parameters corresponding to the operation or behavior of the similarity search algorithm 1009. For instance, this alteration may be related to optimization parameters J described above calculated or interpolated from the REPI's analyzed results 1017. Altering the similarity search parameters (for example, BLAST parameters) alters the method and scoring system typically used in a similarity search. In particular, the illustrated iterative analysis may result in more or less stringent thresholds for suggesting possible matches of test subsequences to known sequences, thus altering or optimizing the output 1019 of the system.

The description of the present invention is further aided by the following detailed example. The following detailed example corresponds to an exemplary embodiment of the invention and is not intended to set forth restrictions on the invention with regard to system operation, parameter settings, sequence data, etc.

An embodiment of the REPI was used to ascertain which base call subsequences from the CustomSeq/GCOS/GDAS process would likely return significant BLAST results through the use of a customized sliding window algorithm. Subsequently, REPI automatically returns BLAST outputs to the end user that allow probabilistic assignments to the likelihood that a given set of base calls correspond to a particular microbial sequence. Moreover, the REPI automatically links sequence fragments to individual pathogens.

Raw sequence data from the resequencing microarray chips is provided by the Genetic Data Analysis Software version 2.0 (GDAS) packaged with the microarray reader. from Affymetrix. GDAS base calling is based on a previously described base-calling algorithm (Cutler et al., 2001). Each of the FASTA output files containing the base calls obtained from the GDAS software was analyzed using specialized software (an embodiment of REPI) that is an exemplary embodiment of the present invention described herein.

In the case of the present examples, the sequence output of GDAS is most often a scattered mixture of contiguous sequence calls (A, T, C or G) that are interspersed with varying amounts of no-calls (Ns) where the GDAS software does not make a base call due to weak hybridization signal on the chip and/or high background hybridization caused by nonspecific binding (Cutler et al., 2001). An example output of the GDAS output (including SEQ ID NO:1) for an Adenovirus 4 (+) clinical sample for the Ad4FIBER tile region is shown below:

```
>Ad4FIBER: 609124A2-8.7.03- 2hour hybridization Start = 12 End = 1245
tcccnacgatgcagncnncnnncgacnangcccttcatcaaccctcccttcgnnctcttcagntggnt tccaagaaaagcccctgggggtgttgnccntaggnnntnnncgaccctgncncnccangaatggggaa ancacncnnantntggngnannnngtggaccttgacgnctcgggaaanctcnttgcaancncagncnn naagnncattgnnnctnntagnttttnccancaacnccattnnnnnttaacatggnnnccccttann cnccaaagntggaaanctnnccttncaagnttctnncnccattaagtatattnngnnnnnnnnntnnn nnntnnntnnnctnnncttttngctcaggtttnggacngnnnngnagngntnngncagtacagttagc ctctncncttncatttgnngnnaaagggaananaaagnttnnnntnnntnnnggnttgcatgttacaa caggaantgcaattgaaagcaacattagntgggctnaaggtnnaaaatttgaagatggtgccanagcn ncaaacattggtaagnnntnnnnnntnnnaaccagnagnncagaacaggagntaanaangcttnncc aanccaagntaaanttgnatctggncncagctttgncagcncaggagnnntaatgnctggcaataaag ncnnngananattanctttgtggacaacgcctgacccatcannaaactgncaaatnctgncngaaaan gangcaaanctancnctttgcttnacnnagnnngnnagncaaatnctggccactgnancagntttggn tgntagaagnggnancntaaacccaattnctggcacagnaagcagngctcaagnttttcnncgntttg atgcaancngtgntcttttancngancactcnannnnnaaaaaatactggggctacnggnaaggagat agcatagatggcactncatacaccaatgctgttggntncntgccaaattcancagcttntnnaaagac ncaaagttctnctnntaaaaataatntannnngncaagnatnnatgaatggngntgtttnaaaaccca ngcttcttnctatanctcttaatggnnctgntgacaccaccagtgcatnntnnntttnattttcntnc acctggactaacggaagctanatcggagcaacatttggagctaactcatacaccttcncntacanngc ccannaannn
```

In the examples provided, REPI was interfaced to a local BLAST (NCBI nt) database (contained on an Apple G5 single processor (1.8 GHz) computer with 4.5 GB of random access memory) via a CGI (Perl) interface. Displayed results included all database sequences within an expect value (E-value) threshold of 1.0e−9. The E-value represents the number of alignments expected at random given the size of the search space, the scoring matrix, and the gap penalties; the lower the E-value the less likely the database sequence similarity matches was in fact a random identification.

The REPI output is comprised of the (Comparable) subsequence and its name, followed by the names, lengths, E-values, and bits scores for each match with that subsequence in descending order of bit scores. The name is reported as the GenBank record's FASTA definition line and includes the sequence length. The score is the normalized score computed from the scoring matrix and gap penalties, the higher the score the greater the similarity.

The REPI output of the example listed above is shown below. (The first subsequence is SEQ ID NO:2 and the second subsequence is SEQ ID NO:3.) For each Comparable subsequence, REPI returns (in descending order of bit score ranking) all GenBank data records having expect values of<the evalue threshold value, currently 1.0 E−9. The highest bit score is achieved for the adenovirus 4 prototype while field strains from Air Force and Navy training sites are suitably distinguished by lower bit scores.

```
>Ad4FIBER: 609124A2-8.7.03- 2hour hybridization Start = 12

End = 1245

Subsequence:

tcccnacgatgcagncnncnnncgacnangcccttcatcaaccctcccttcgnnctcttcagnt ggnttccaagaaaagcccctgggggtgttgnccntaggnnntnnncgaccctgncncnccanga atggggaaancacncnnantntggngnannnngtggaccttgacgnctcgggaaanctcnttgc aancncagncnnnaagnncattgnnnctnntagnttttnccancaacnccattnnnnnttaaca tggnnnccccttanncnccaaagntggaaanctnnccttncaagnttctnncnccattaagta tattnngnnnnnnnnnt Subsequence Percentage of Target: 27%

Subsequence Length: 337
```

-continued

Number of Subsequence Base Calls: 249

Percentage of Subsequence Base Calls: 74% gi|434913|emb|X76547.1|AV4FIB1 Adenovirus type 4 gene for fiber protein; Length = 1375 evalue: 3.35737E-33, score: 149.17 for Ad4FIBER lcl|AY599837 | Human Adenovirus serotype 4, USAF Field Strain | 35,964 bp; Length = 35964 evalue: 4.51313E-20, score: 105.558 for Ad4FIBER lcl|AY599835 | Human Adenovirus serotype 4, US Navy Field Strain | 35,965 bp; Length = 35965 evalue: 4.51313E-20, score: 105.558 for Ad4FIBER lcl|AY594254 | Human Adenovirus serotype 4, vaccine strain#| 35,994 bp; Length = 35994 evalue: 4.34733E-17, score: 95.646 for Ad4FIBER lcl|AY594253 |Human Adenovirus Serotype 4| 35,990 bp; Length = 35990 evalue: 4.34733E-17, score: 95.646 for Ad4FIBER gi|17105037|gb/AF394196.1|AF394196 Simian adenovirus 25, complete genome; Length = 36521 evalue: 2.58354E-12, score: 79.7872 for Ad4FIBER gi|33694802|tpg|BK000413.1| TPA: Simian adenovirus 25, complete genome; Length = 36519 evalue: 2.58354E-12, score: 79.7872 for Ad4FIBER gi|22796371|emb|AJ315930.1|HAD315930 Human adenovirus type 4 DNA; Length = 12718 evalue: 2.58354E-12, score: 79.7872 for Ad4FIBER

Subsequence:

tnnntnnnctnnncttttngctcaggtttnggacngnnnngnagngntnngncagtacagttag cctctncncttncatttgnngnnaaagggaananaaagnttnnnntnnntnnnggnttgcatgt tacaacaggaantgcaattgaaagcaacattagntgggctnaaggtnnaaaatttgaagatggt gccanagcnncaaacattggtaagnnntnnnnnntnnnaaccagnagnncagaacaggagnta anaangcttnnccaanccaagntaaanttgnatctggncncagctttgncagcncaggagnnnt aatgnctggcaataaagncnnnganananattanctttgtggacaacgcctgacccatcannaaac tgncaaatnctngcngaaaangangcaaanctancnctttgcttnacnnagnnngnnagncaaa tnctggccactgnancagntttggntgntagaagnggnancntaaacccaattnctggcacagn aagcagngctcaagnttttcnncgntttgatgcaancngtgntctttttancngancactcnann nnnaaaaaatactggggctacnggnaaggagatagcatagatggcactncatacaccaatgctg ttggntncntgccaaattcancagcttntnnaaagacncaaagttctnctnntaaaaataatnt annnngncaagnatnnatgaatggngntgtttnaaaacccangcttcttnctatanctcttaat ggnnctgntgacaccaccagtgcatnntnnntttnattttcntncacctggactaacggaagct anatcggagcaacatttggagctaactcatacaccttcncntacanngcccannaa

```
Subsequence Percentage of Target: 72%

Subsequence Length: 888

Number of Subsequence Base Calls: 701

Percentage of Subsequence Base Calls: 79% gi|434913|emb|X76547.1|AV4FIB1 Adenovirus type 4 gene for fiber protein; Length = 1375 evalue: 3.29583E-171, score: 609.077 for Ad4FIBER lcl|AY599837 | Human Adenovirus serotype 4, USAF Field Strain | 35,964 bp; Length = 35964 evalue: 7.18119E-160, score: 571.412 for Ad4FIBER lcl|AY599835 | Human Adenovirus serotype 4, US Navy Field Strain | 35,965 bp; Length = 35965 evalue: 1.75062E-157, score: 563.482 for Ad4FIBER lcl/AY594254 | Human Adenovirus serotype 4, vaccine strain#| 35,994 bp; Length = 35994 evalue: 6.18269E-148, score: 531.765 for Ad4FIBER lcl|AY594253 | Human Adenovirus Serotype 4| 35,990 bp;

Length = 35990 evalue: 6.18269E-148, score: 531.765 for Ad4FIBER gi|303967|gb|L19194.1|ADRFIBERX Mastadenovirus h4 fiber protein, complete cds; Length = 1346 evalue: 1.50721E-145, score: 523.835 for Ad4FIBER gi|22796371|emb|AJ315930.1|HAD315930 Human adenovirus type 4 DNA; Length = 12718 evalue: 3.67425E-143, score: 515.906 for Ad4FIBER gi|17105037|gb|AF394196.1|AF394196 Simian adenovirus 25, complete genome; Length = 36521 evalue: 2.91419E-51, score: 210.623 for Ad4FIBER gi|33694802|tpg|BK000413.1| TPA: Simian adenovirus 25, complete genome; Length = 36519 evalue: 2.91419E-51, score: 210.623 for Ad4FIBER
```

In this detailed example, the REPI parameters were set as follows:

TABLE 2

| Parameter/Threshold | | Value |
|---|---|---|
| Expect Value Threshold | | 1.0E-9 |
| Window Size | Z | 20 |
| First Jump Threshold | A | 25% |
| First Window Jump | X | 1 |
| Second Window Jump | Y | 1 |
| Second Jump Threshold | B | 25% |
| First Length Threshold | E | 20 |
| Second Length Threshold | F | 50 |
| Intermediate Percentage Threshold | H | 60% |

In addition to the embodiments described above, the extensible nature of the system allows for ready adaptation to a number of higher bioinformatics tasks that utilize discontinuous segments of nucleotide or amino acid sequences. Several examples of these supplementary applications are described below.

In the previous examples, the present inventors provided data showing that sequence fragments can be linked automatically to individual target sequences. In several more preferred embodiments, this approach discriminates between a mixture and a recombination within a set of orthological biological target sequences. Herein, an ortholog is defined generally as a same gene in a different species, usually an indication of common genetic ancestry.

More specifically, the system attempts to perform automatic alignment of sequence calls from different tile regions of the resequencing microarray to detect the presence of homologous sequence fragments on different tiled regions of the array, allowing inference of a mixture of target sequences. Optionally, the system further determines that the sequence outputs from different tiled regions representing orthologous genes are not mixtures of orthologous genes but correspond to a contiguous sequence that may have arisen by a genetic recombination event between different regions of two or more orthologous genes.

In such additional embodiments, the system allows for automatic detection of highly overlapping or homologous sequence fragments on different tiled regions of the array, allowing inference of a mixture of target sequences. Further, the system optionally determines that the sequence outputs from different tiled regions are not highly overlapping but correspond to contiguous sequence that may be registered to positions within known target sequences to infer a genetic recombination event.

Figure 12:
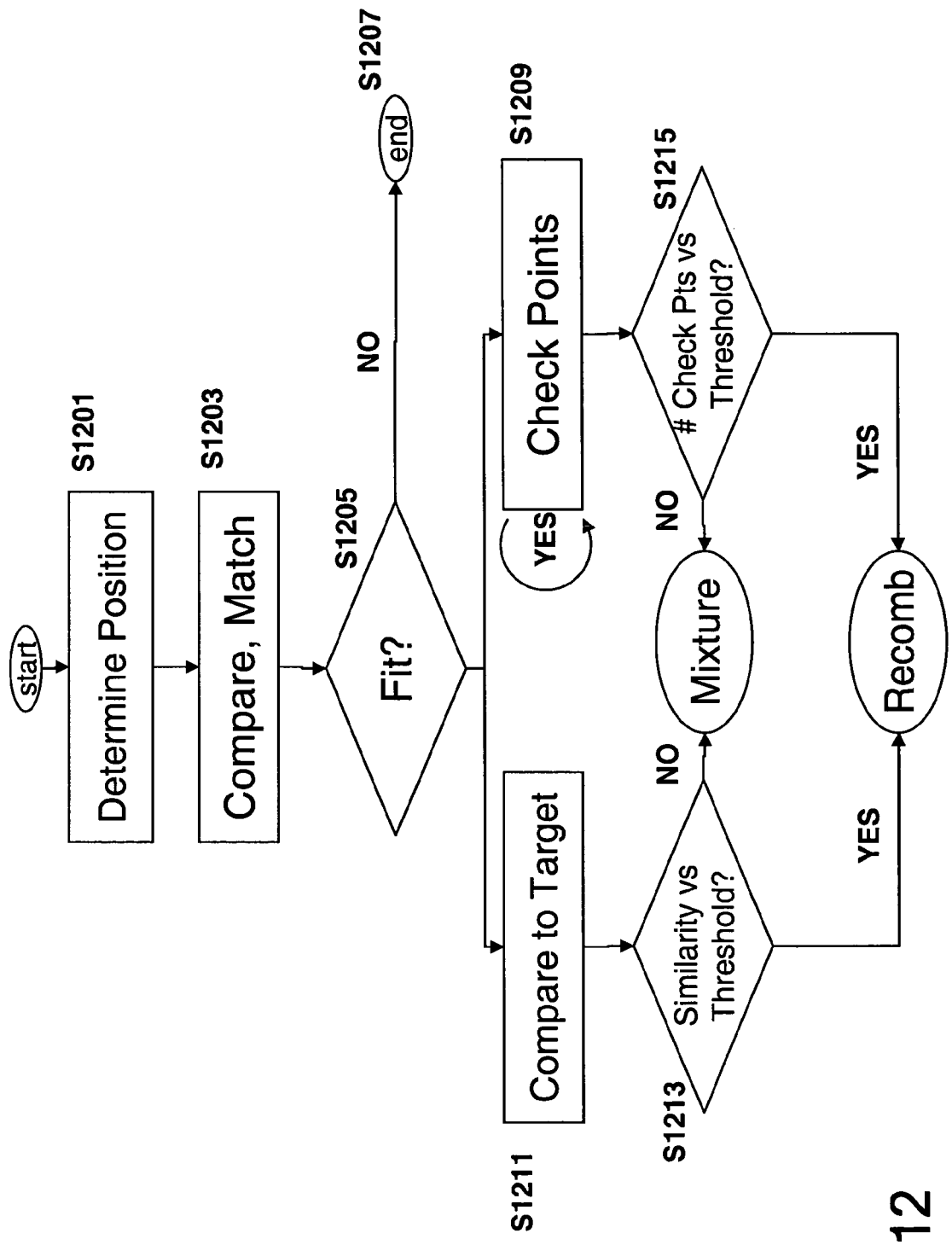
FIG. 12 is an exemplary flowchart of an embodiment for distinguishing between a mixture and a recombination.

FIG. 12 illustrates an exemplary embodiment of methods for distinguishing between mixtures of different targets and recombinants between targets in a test sample according to an embodiment of the present system. These example methods can be integrated into or supplemented with the methods described above with respect to FIG. 3, and are also applicable to distinguishing between protein mixtures and hybrid proteins. In this example, the system determines the relative position of gene subsequences detected by the resequencing microarray (with or without an initial similarity search) with respect to the entire nucleotide sequence that codes for a protein S1201. The relative position corresponds generally to the location of the subsequence within the whole sequence. The whole sequence is available in a database that can be comprised of public and/or private sequence records. For example, a subsequence can be determined to correspond to a front (for example, 5'), middle, or end (for example, 3') of an entire sequence. Moreover, this determination of position can be made of a candidate subsequence or a selected subsequence. Next, the system performs an alignment procedure to compare and match subsequences according to their position S1203. The algorithm used to perform S1203 can be one used for local pairwise alignment (e.g. BLASTN, BLASTP, or BLASTX) between two sequences, one which simultaneously performs alignments. between multiple sequences (e.g. ClustalW or Clustal_X (Thompson et al., 1997; Thompson et al., 1994)), or an alternate one obtained from the public domain or through private development. In one embodiment, the system groups subsequences corresponding to the front, middle, and end portions of like sequences. Subsequently, the system evaluates the fit of the grouped subsequences with each other S1205.

Fit among subsequences can be evaluated, for example, through detection of appropriate amounts of overlap among the sequences. In one embodiment, the fit is a quantitative relationship between the length (or bit score) of the homologous overlap region in relation to the non-overlapping sequence(s), and the relationship of each to the overall sequence of the whole gene for a given protein. In addition to traditional methods of evaluating overlapping biological sequences, the system optionally analyzes sequence overlap using synchronization and detection methods applicable to analog and digital communications. Moreover, the issue of identifying overlapping sequences is not unlike that problem posed by initial synchronization in digital communication systems. Accordingly, one method that may be employed according to the present invention is the use of a sliding correlator. In a sliding correlator, two sequences (a data sequence, and a hypothesis sequence), are compared to one another by correlating the two sequences. The two sequences are shifted in position with respect to one another, and shifting stops only when the correlation result is detected to be above a predetermined level. In practice, a sliding correlator is often preceded by some other method for reducing the area of search such as the transmission of a synchronization preamble. Likewise, according the present invention, an already-detected overlap between subsequences may be used as a preamble in order to limit the amount of time required for the synchronization process. This type of synchronization is described in Bhargva, et al. "Digital Communications By Satellite" John Wiley and Sons, Chapter 9, pages 269-291, the entire contents of which being incorporated herein by reference. Likewise, other synchronization or acquisition algorithms may be applied such as those described in §8.22 of Sklar, B. "Digital Communications Fundamentals and Applications", Prentice Hall, 1988, pages 453, 460, the entire contents of which being incorporated herein by reference. The acquisition criterion used is selected based on a sufficiently low probability of false acquisition. In this case, the acquisition criterion may be the probability of false detection of 10%, although 9%, 8%, 7%, 6% inclusive, down to 0.1% may be employed.

If the subsequences do not exceed a predetermined threshold of fit, the system begins analysis of an alternative subsequence S1207. That is, if two or more potentially homologous or orthologous sub-sequences do not fit a model for either mixture or recombination, the system can proceed to search for other subsequences S1201. The collection of grouped subsequences can be compared to the entire (target) sequence using a similarity search algorithm S1211. In such a case, the level of similarity S1213 between the linked subsequences and a target sequence provides data indicating whether the detected biological sequences are from a mixture of different biological entities or whether the detected sequences indicate a recombination. Alternatively, the system employs a method of check points to evaluate overlapping hybridization between portions of subsequences. The check point method performs such an evaluation at multiple points along the subsequences S1209. In this approach, the number of checkpoints is compared against a threshold S1215 to provide evidence distinguishing between a biological mixture and a recombination.

For example, a co-infection of two viruses of the same type might produce a recombinant within a single gene that is identical to one virus except for the 5' end, which has been substituted with the corresponding section of the second viral gene for the same protein. When this new recombinant virus genome is hybridized on a resequencing microarray, it might produce signals from the corresponding sections of the resequencing tile regions. An embodiment of the present invention includes an assembly algorithm to construct a "model" of the target sequence showing which parts might fit together to form an entire target. If the two have significant overlap (for example, demonstrating homology beyond some threshold value), one might conclude that there is probably a mixture. But if there were little or no overlap, there would remain a possibility that there is a recombinant. The degree of overlap (or lack of) could be affected by low concentrations of target with correspondingly smaller amounts of the tiles being filled in. This same principle can be applied even more readily, and with greater impact, on viruses where the recombination is a steady and recurring event, as in the case of retroviruses, where recombinations between viral genes result in the formation of new viral strains. In fact, such described functionality is essential for the distinction of mixtures of target sequences versus a recombination between target sequences. Moreover, this additional functionality may also be used to more rapidly detect common regions in detected (and possibly) new recombinations and assist in the design PCR primers to assist in broader studies of recombinations detected by the system.

Not only is the present inventive approach able to distinguish between mixtures of biological entities and recombination events within a given entity (described elsewhere herein), an additional embodiment of the system advantageously provides an end user with quantitative estimate of the relative amount of target sequence that was detected in the resequencing microarray assay. Such decision-quality information is of increased utility when, for example, a clinician or clinical laboratory technician attempts to assign cause and effect when multiple pathogen genomic signatures are detected. Further, supplementing data regarding the presence of a biological substance(s) with data regarding the (relative and absolute) abundance of the biological substance(s) provides additional context for decision-making by an end user. Further, an embodiment of the system is configured to automatically analyze and compare such "presence" and "abundance" data to provide an end user with decision-quality information.

Embodiments of the system are configured to utilize two types of data for providing abundance information. The first is the absolute intensity of the hybridization signals on the chip. A non-linear relationship exists between the amount of target in solution and the amount that actually hybridizes and the resulting signal. However, an estimate of the amount of target nucleic acid in the sample could be made by comparison with a standard curve prepared under control conditions. For example, the signal intensity data is readily available from the CEL file in the Affymetrix data hierarchy and is typically used for quantitative assessment of gene expression changes. An embodiment of the system accommodates the inclusion of intensity values within the data it inputs, outputs, and handles. Secondly, the percentage of base calls, both as a percentage of the total tile region size and as a percentage of base calls within a selected subsequence satisfying the sliding window algorithm, can be used as a measure of concentration. Results from tests performed by the inventors show that both of these percentage metrics decrease with decreasing target concentration, although the correct target sequence can still be identified.

Figure 13:
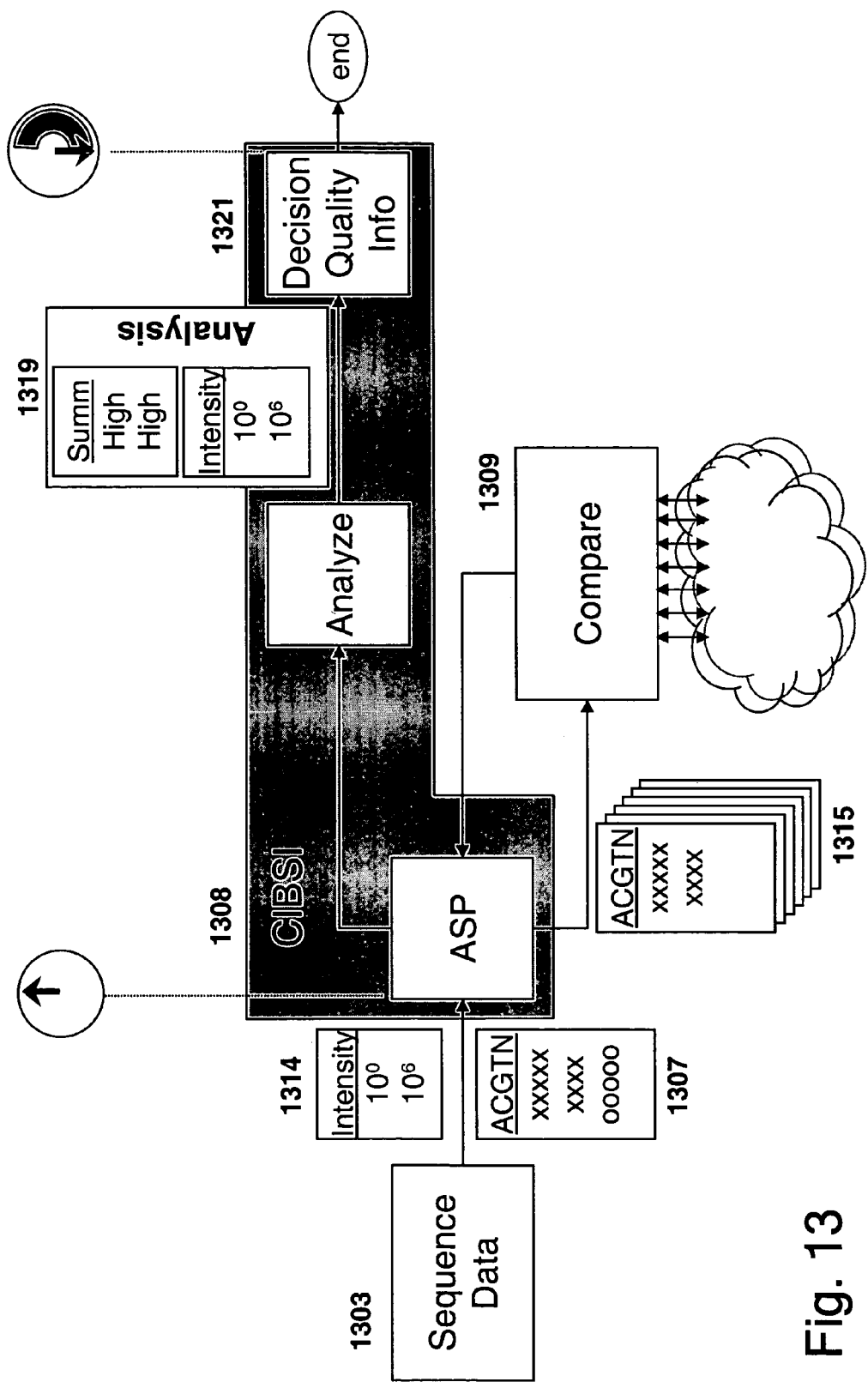
FIG. 13 is a stylized exemplary schematic of an embodiment that incorporates intensity data to provide decision-quality information to a user.

FIG. 13 is an exemplary illustration of an embodiment of the CIBSI that incorporates intensity data with results of a similarity search to provide a user with decision-quality information. Intensity data 1314 is input from, for example, a spectrum analysis tool of a microarray. The intensity data is analyzed in the context of the results of the similarity search to perform more robust analysis 1319 of detected sequences and consequently provide decision-quality information 1321 to the user. Decision-quality information includes, for example, a measure of a relative abundance of detected sequences or subsequences corresponding to distinct or related biological entities. An additional embodiment incorporates intensity data 1314 in distinguishing between mixtures and recombinations as described previously. The intensity data 1314 in such a case would provide an additional dimension of information when applying digital communications methodologies for interpreting sequence data returned from the similarity search.

In another very preferred embodiment, the system allows for the analysis of transcriptional markers (e.g. RNA) that have been resequenced using the presently described type of microarray (via hybridization of RNA or complementary cDNA). In a method analogous to that described above for inference of genomic recombination events, transcriptional sequences may also be assembled to determine biological entity viability and transcriptional editing events that can serve as markers for infection.

Further, the system optionally is adaptable for use with biological sequences other than nucleic acids and their related transcriptional products such as the amino acids sequences of proteins. Generally, proteomic applications of the present invention are consistent with the system's ability to handle biological sequence data and optimize such data for comparison against known sequences. The studies of gene expression and protein evolution have lead to amino acid sequence databases (and associated similarity search algorithms) similar in scale and accessibility as genetic sequence databases described above. Moreover, the analysis of spectrum data returned from mass spectrometry methods for sequencing proteins lends itself conveniently to even more elaborate embodiments of the invention. For example, protein sequence spectrum data includes intensity data similar to those used in the analysis of microarrays. As described above with respect to other types of sequences, an advanced embodiment of the invention provides for the handling and utilization of such intensity data to provide higher quality information to an end user.

In addition to the use of the system in diagnostic applications, alternative embodiments of the system facilitate the design of more effective and efficient resequencing microarrays for use with diagnostic embodiments of the system. A more effective approach to choosing and designing probes for inclusion on microarrays inevitably leads to more efficient use of the real estate on a given microarray. Consequently, microarrays can be made to accurately detect a larger variety of biological sequences for a given size, or microarrays tailored for specific applications can be made cheaper and more accessible by reducing the required number of probes required on a microarray, which increases the opportunity for size reduction and higher manufacturing yields. One key driver of designing a microarray is resolution. Generally, resolution as described herein refers to the discriminatory power to distinguish between closely related strains of a biological entity. For example, some applications may require a high resolution to distinguish between Air Force and Navy Field Strain of adenovirus, while other applications require only identification of the presence of an adenovirus. The embodiments described below illustrate uses of the system in enabling a microarray designer to objectively and systematically balance resolution and microarray size/density.

Figure 14:
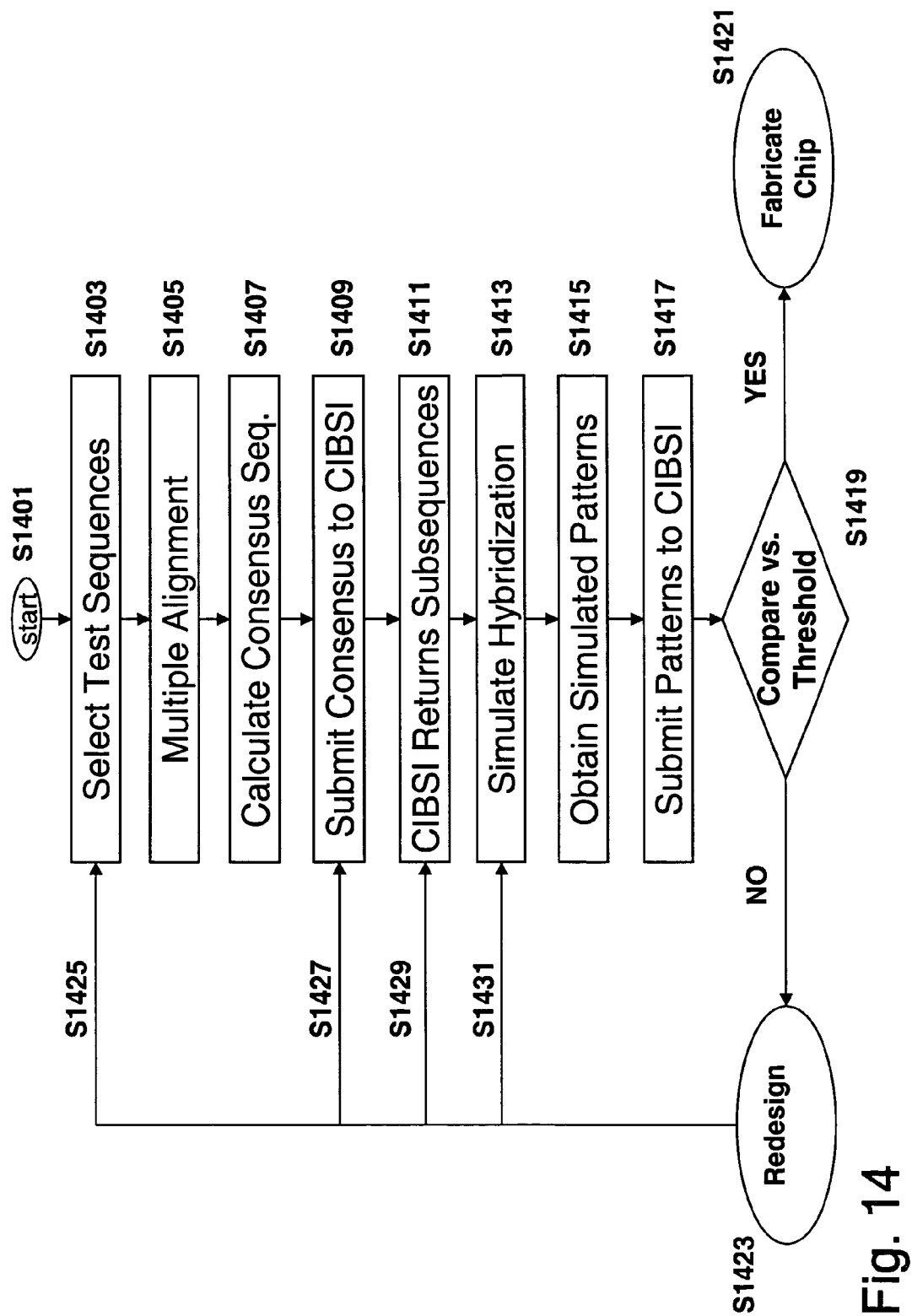
FIG. 14 is an exemplary flowchart illustrating a method for designing or optimizing a resequencing microarray.

FIG. 14 illustrates an exemplary embodiment of methods utilizing the system for accelerated design and refinement of a resequencing microarray or other probe or array-based assay. To begin, test sequences are selected corresponding to types of biological sequences (which, in turn, correspond to biological entities including pathogens) that are intended to be detected by a microarray S1403. Preferably a composition of more than one known or estimable biological sequence that may or may not be closely related, the selected sequences can be chosen through a variety of methods including, but not limited to, phylogenic trees and Hidden Markov Models (Eddy, 1998). These selected test sequences then undergo multiple alignment using a multiple alignment algorithm such as CLUSTALW S1405. Performing multiple alignment leads to a consensus sequence S1407, typically corresponding to common regions of the test sequences where commonalities are determined by comparison to a certain similarity threshold (for example, CLUSTALW weights, CLUSTALW parameter setting percentage to determine consensus). The resultant consensus sequence is then input into an embodiment of the system to yield one or more subsequences of the consensus sequence that are determined as likely able to yield meaningful results from a similarity search S1409. In one approach, the subsequence(s) from the consensus sequence are then "hybridized" with the originally selected test sequences through a simulation that mimics the behavior and limitations of, for example, an Affymetrix resequencing microarray S1413. Hybridization rules include, but are not limited to, rules for tolerance and detection of insertions, deletions, and substitutions of various numbers of base pairs or at various locations within an entire sequence. The output simulated hybridization patterns between the test sequences and the consensus sequence are then obtained S1415 and subsequently submitted to the system for automated comparison using a similarity search S1417. The results of the similarity search are then compared S1419 to the set of originally selected test sequences. Generally, a similarity search returns at least one known biological entity and an associated probability that the submitted sequence or subsequences is from that known entity. Thus, comparison of the similarity search results can confirm or deny that a probe based on a relevant portion of a consensus sequence would be effective in correctly hybridizing to, and consequently identifying, the collection of test sequences of concern to a user. In the case: that the results confirm the effectiveness of the consensus sequence (or some subset thereof), that sequence can be implemented in a region of a resequencing microarray S1421. Alternatively, if the comparison suggests that the test sequences of concern would not be adequately detected, then the system can be used in further redesign of a new probe S1423. One embodiment of such a redesign process includes reevaluation of several of the steps within the original design process, some of which are illustrated in FIG. 14. For example, the results are affected by the diversity of range of selected test sequences and their weighting according to their prevalence in the environment S1425. Additionally, weighting of the consensus algorithm is adjustable S1427 as well as functional parameters related to the system S1429. Furthermore, the various methods implemented in simulating hybridization are adjustable, including a wholesale change of algorithm and Signal-to-Noise Ratio thresholds S1431.

Accordingly, the functionality of the system provides accelerated and more effective design of resequencing microarrays compared to a conventional method of subjectively choosing probes.

Figure 15:
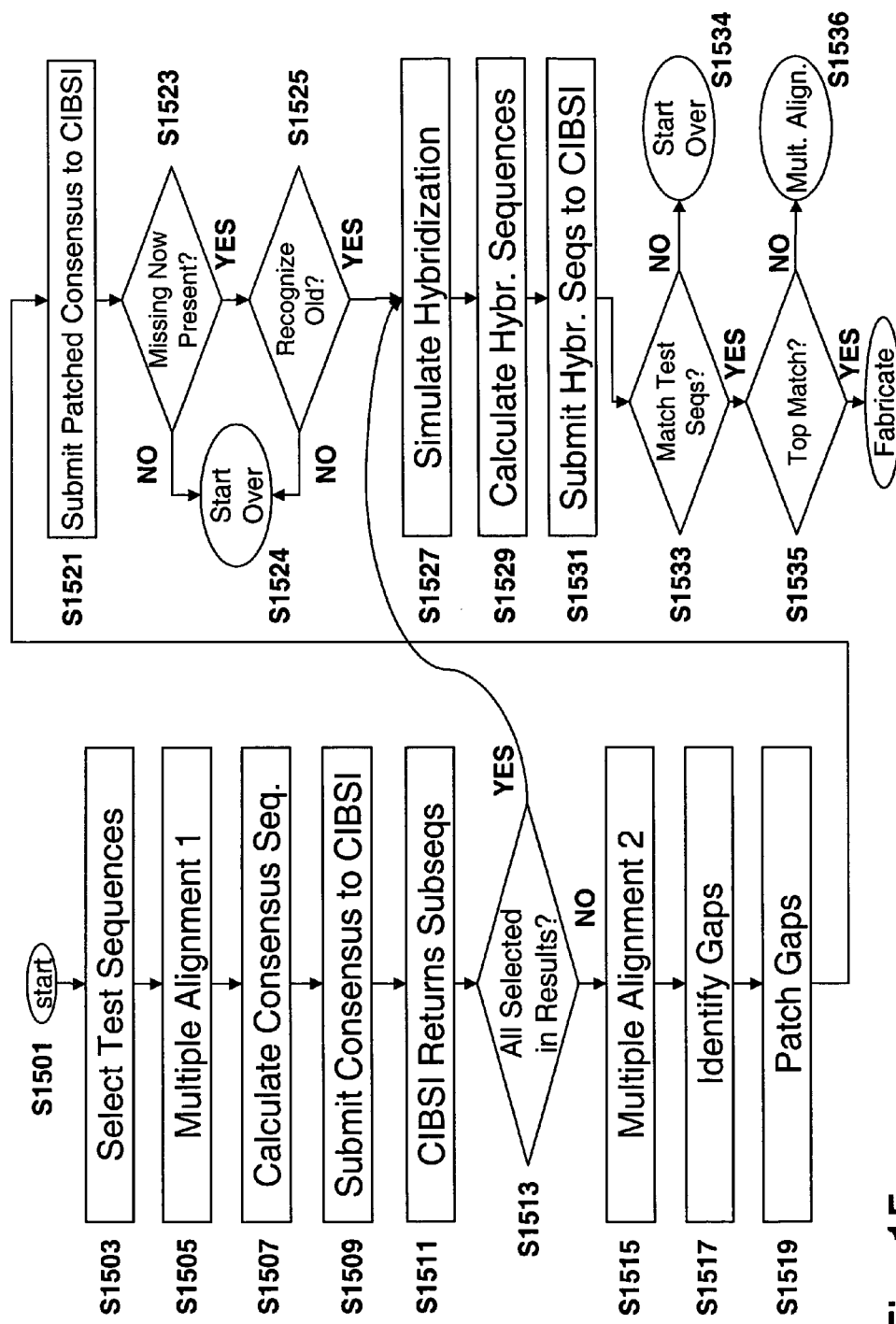
FIG. 15 is an additional exemplary flowchart illustrating a method for designing or optimizing a resequencing microarray.

The above aspects related to design are further illustrated by the following example conducted by the inventors. In this example, a method is described for creating a consensus sequence to be used as a target sequence on a microarray that is capable of identifying those test sequences used to create it. FIG. 15 illustrates an exemplary embodiment of the method described below.

Figure 16:
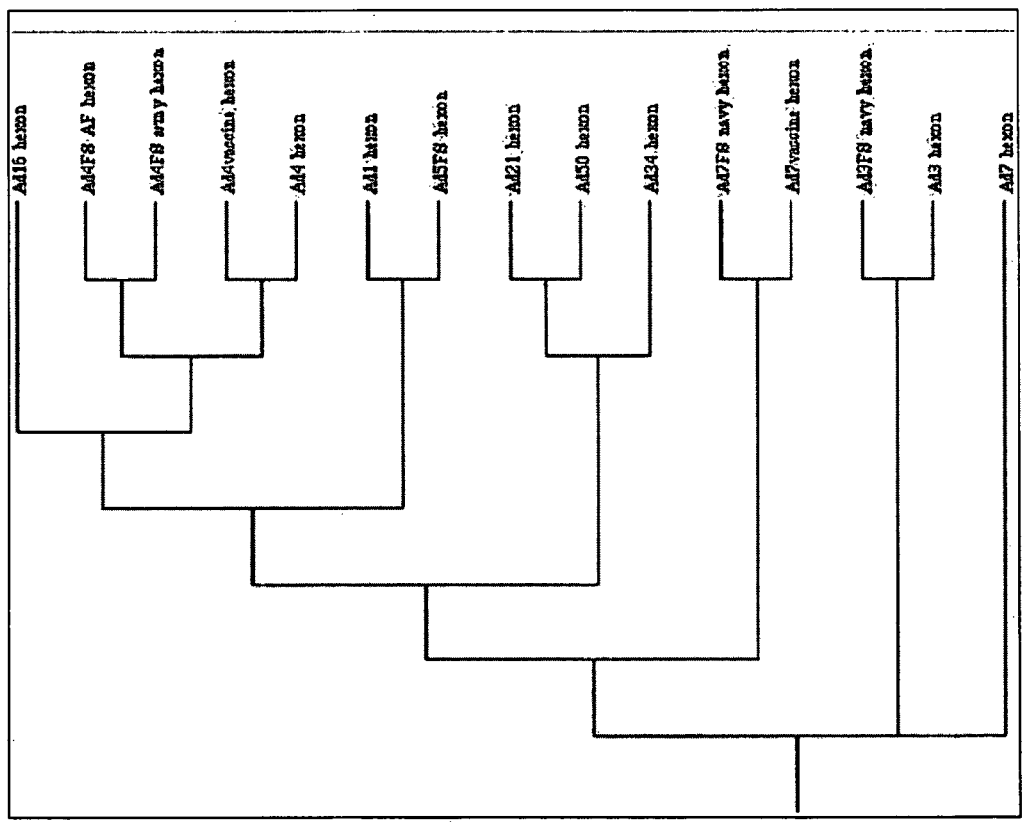
FIG. 16 is an example of a dendrogram.

Beginning with 15 adenovirus hexon gene sequences, these sequences are arranged according to phylogeny using a dendrogram (for example, see FIG. 16). The dendrogram is used to graphically represent and evaluate the genetic relationships among selected test sequences. Although Ad1 and Ad5 are the greatest outliers with respect to the other sequences, all 15 shown adenovirus hexon gene sequences are selected in this example as an initial set of test sequences S1503. Selection of the initial set of test sequences S1503 is optionally provided automatically by the system according to predetermined or user-defined parameters. For example, the distances between the sequences in the dendrogram provide a numerical threshold set for determining the minimum or maximum distance required to combine sequences in a candidate consensus sequence.

Figure 17:
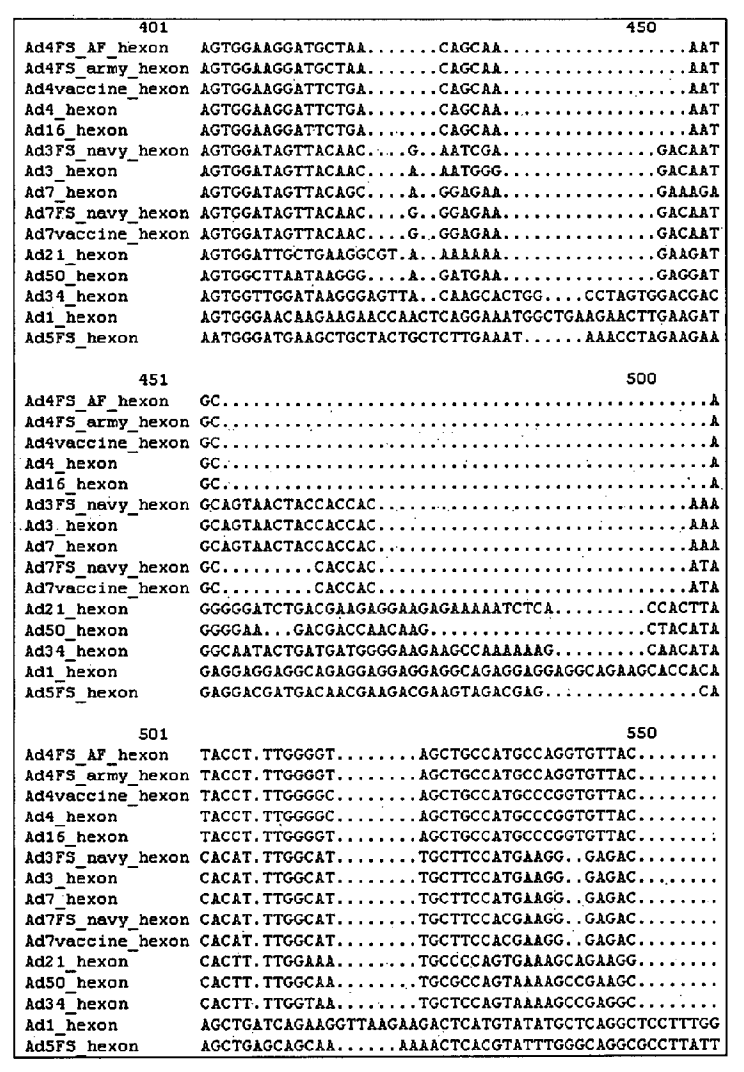

Next, all selected test sequences are subjected to a multiple alignment analysis S1505 such as ClustalW (Thompson et al., 1994), a sample output of which is shown at FIG. 17. A consensus sequence is then calculated from this alignment S1507. The example illustrates this step performed by Cons (EMBOSS interface to ClustalW) at FIG. 18, with Cons run at low "plurality," a parameter allowing a user of Cons to set a cut-off for the number of positive matches below which there is no consensus. Specifically, a lower plurality allows fewer matches to build the consensus, thus creating a consensus with fewer gaps and Ns.

Once a candidate consensus sequence is calculated, it is input into REPI (or, alternatively, another embodiment of the present invention) to initially evaluate its potential effectiveness as a target sequence S1509 using an Expect threshold value of 1e−9 for returning prospective matches S1511. At this point, the REPI results are compared to the initial set of test sequences S1513 as, for example, a percentage of the initial set of test sequences present in the REPI results. If this percentage of initial test sequences. identified by the REPI results is greater than a threshold (predetermined by the system or, alternatively, defined by the user), the candidate consensus sequence is the most probabilistically favorable large-scale target sequence, and the process moves to simulating hybridization S1527. In the illustrated example, the above comparison threshold is 100%, corresponding to a condition that all of the initial test sequences must be returned by REPI as exceeding the Expect threshold. Reducing this comparison threshold results in a system more permissive of a target sequence that may misidentify or fail to identify a certain number or percentage of a desired set of test sequences.

Otherwise, if each of the initial set of test sequences are not all present in the REPI results, the missing test sequences are then be evaluated with the candidate consensus sequence individually. The candidate consensus sequence are also evaluated in combination with the multiple alignments created in a previous step to identify any missing sequence segments that are critical for their identification within this consensus. The objective of the following steps is to incrementally add necessary sequence information to the original candidate consensus sequence without losing the original sequence generality of the original.

Accordingly, a multiple alignment is performed S1515 again. This time, the multiple alignment includes the current consensus sequence. Subsequently, gaps in the candidate consensus sequence are identified S1517. The gaps in the alignment of the candidate consensus sequence with the test sequences are possible positions for missing sequence data where adding incremental sequence information to the candidate consensus sequence from the missing test sequences may be beneficial.

FIG. 19 illustrates an example of gaps in results from the second multiple alignment. In this example, there are two places where the consensus sequence skips sequence data from Ad1 and Ad5, noted previously as the two greatest phylogenic outliers during the initial test sequence selection process (see FIG. 16).

Segments from the missing sequences corresponding to the gaps are then added, or "spliced," to the original consensus sequence in place of the gaps S1519 to form a "patched" consensus sequence. FIG. 20 illustrates spliced sequence data within the patched candidate consensus sequence. According to an embodiment of the present invention, splicing is done manually by a user. Optionally, the system provides automatic splicing according to parameters (predetermined by the system or set by the user) corresponding to the identification of gaps and the selection of sequence data from missing test sequences for splicing into the gaps.

After splicing S1519, the patched candidate consensus sequence is again submitted to REPI for evaluating the impact of the above manipulation S1521. Optionally, the system or user determine additional acceptability thresholds corresponding to a number (or percentage) of missing test sequences now correctly identified S1523 or a number (or percentage) of previously identified test sequences now incorrectly identified by the REPI results S1525. Such thresholds generally correspond to a tolerance for improvement or degradation in the effectiveness of a patched consensus sequence with respect to the initial candidate consensus sequence. In the illustrated example, the addition of two sequence segments is enough to add Ad1 and Ad5 to the list of REPI hits without losing any of the previously identified test sequences.

On the other hand, if the splicing operation failed to add the missing adenovirus types to the list of those identified or other sequence hits were lost in the process the new consensus sequence would be abandoned, Ad1 and Ad5 are separated and the remaining sequences are reevaluated S1524. Alternatively, if the splicing operation failed to meet an acceptability threshold, a reevaluation is performed. Accordingly, in cases where the sequence differences among the initial set of test sequences fails to meet an acceptability threshold (for example, those described immediately above), two or more candidate consensus sequences may be necessary to provide target sequences that are able to identify a desired percentage of the initial set of test sequences. Optionally, the system accommodates consideration and evaluation of such additional candidate consensus sequences in parallel.

If all of the original sequences have been identified in the REPI results (see FIG. 21), a final consensus sequence has been formed and the hybridization potential for each of the original test sequences can be determined. FIG. 22 shows a hybridization/binding simulation program used to perform this step. Each of the original sequences is aligned with the new consensus sequence. The simulation takes the output alignment file, produced, for example, by a b12seq alignment program, and evaluates the number of differences in the top scoring alignment per 25 mer. Optionally, the program evaluates the number of differences at longer or shorter intervals. The system then builds a resulting sequence (as shown in FIG. 22 for Ad4) based only on those positions where the 25 mer's had less than 2 mismatches. Additionally, a separate threshold parameter for tolerance of mismatches is optionally provided by the system.

The sequence shown in FIG. 22 is a simulated representation of a test sequence hybridized with the current consensus sequence. The hybridization potential of each of the sequences with the final consensus sequence is then evaluated S1527. In this example, program HybBind is used to create hybridization simulation sequences for each test sequence S1529. Once the hybridization simulation sequences are all created, they are each run through REPI as if they were acquired off of the actual chip S1531.

If all of the simulated sequences match their respective sequence as the top score and top "hit" (similarity score based on bit score and/or expect value), then this potential consensus sequence has passed the evaluation process and can be used as a target sequence to identify, by type, those sequences used to create it S1535. Alternatively, if all of the simulated sequences do not match their respective sequence as the top score S1535, or the top score and E-value match multiple sequences S1533, the potential consensus fails the evaluation the sequences are broken up into multiple groups and sent back for reevaluation S1534.

The potential sequences that did not correctly identify their respective sequence (Ad1, Ad50, Ad34, Ad3) are sent back to step one to be reevaluated for one or more consensus S1534. The potential sequences Ad4, Ad21, Ad16, Ad7, Ad5, that did correctly identify their respective sequence as the top score and E-value are grouped together and are sent back through the process described above starting with the creation of a multiple alignment to build a new candidate consensus sequence without the use of those sequences that failed and did not correctly identify themselves S1536. The new candidate consensus sequence (for example, see FIG. 23) is run through the same thresholds and evaluations, b12seq, REPI, Hybbind and REPI again. In this case when the final simulated sequences from Hybbind are run through REPI for validation all of the sequences are able to identify their respective sequence by type as the top score and E-value therefore this potential consensus sequence has passed all evaluation and can be used as a target for sequences Ad4, Ad21, Ad16, Ad7, and Ad5.

In yet another embodiment, the system provides for tracking and analysis of time trends in sequence analysis. By performing and recording analysis similar to that described above iteratively or continuously over time, genetic or proteomic evolution and/or mutation can be tracked more easily than using the conventional method.

In a specific embodiment related to pathogen detection, the invention described herein is used for the routine diagnosis and surveillance of common respiratory pathogens in a clinical setting (at or near point-of-care). Readily obtainable samples (e.g. nasal wash, throat swab, sputum, blood, food, soil, water, or air) are processed in a simple manner to produce nucleic acid isolates that are obtained using an adsorptive process, enriched for pathogen-specific targets, amplified using a non-biased (e.g. total) or multiplexed PCR amplification method, and hybridized on the resequencing microarray for a defined of time prior to washing and imaging. The overall process is sufficiently simple such that a skilled technician (medical technologist level) will be able to perform the assay without a significant interruption in their routine work pattern. Base calls are made using the custom algorithms or using the steps specified by the vendor. REPI, or some variant thereof, is used to automatically parse the base calls made by the microarray, and provide the end-user (e.g., physician, health care provider, public health officer, or other decision-makers) with decision-quality information for management (e.g., diagnostic, treatment, prognostic and outbreak control/containment measures) of the infectious pathogen(s) that are causative of the disease symptoms and complications. This analysis occurs locally through the use of an embedded sequence database that would be queried by REPI (e.g. local dedicated BLAST server). In addition to providing a routine diagnostic functionality, the microarray used in conjunction with this embodiment also carries markers for highly improbable (e.g. avian influenza or bioterrorism) pathogens that would be cause for involvement of others, namely public health officials.

In selected embodiments of the present invention, CIBSI outputs are arranged in multiple layers. In a particular embodiment, CIBSI outputs are arranged in three layers for presentation to a user or data interpreter. A first layer of output provides "species level" information, a second layer of output provides "serotype/strain level" information, and a third layer provides "low level" information. Examples of species include, but are not limited to, Influenza A, Influenza B, Adenovirus, *S. pyogenes, B. anthracis*, and *F. tularensis*. Although the species level layer is presented first to a user or data interpreter, the user or data interpreter is able to select and view other layers through, for example, user inputs, predetermined display settings, or prescribed protocol by qualified individuals. Alternative embodiments provide for rules and algorithms to retrieve, organize, and present data corresponding to predetermined levels of detail within each layer.

In one embodiment, a rule for a positive at the first level is that if any one of the multiple tile regions for a species produces a positive (for example, produces a subsequence having a BLAST expect value of $1.0e^{-9}$ or less or produces a high bit score for a single pathogen database record), then the result is POSITIVE at the species level. This enables a fully autonomous first layer of detail to be established. The user can produce more information that this first layer through, for example, a human intervention step to access second or third layers of information. The second layer of output including "serotype/strain level" information enables a user to view sequence database (for example, GenBank) record names and identifiers with scores above a predetermined threshold to determine serotype and/or strain. Optionally, text search algorithms can be applied sequence databases without precise naming conventions to automatically provide serotype/strain level information (for example, through searching and parsing of GenBank data). Alternatively, the system provides for addenda (for example, adenovirus 4, AF field strain or influenza A, H3N2, Fujian 411) to be made to the first layer of information by a user or data interpreter by selecting an option next to a display field. The third layer of output includes raw CIBSI output. Optionally, algorithms may be applied to the raw CIBSI output. Other embodiments of the present invention move additional information to the first layer of output.

FIG. 11 is a block diagram of a computer system (or server) 2001 upon which an embodiment of the present invention may be implemented. It should be noted however, that the present system need not be based on a personal computer (PC) configuration, but rather a custom processor-based system that does not include the features of a general purpose computer may be used as well. Nevertheless, because the actual hardware configuration used to support the present invention, is not so restricted, an example of PC-based system is now provided. The computer system 2001 includes a bus 2002 or other communication mechanism for communicating information, and a processor 2003 coupled with the bus 2002 for processing the information. The computer system 2001 also includes a main memory 2004, such as a random access memory (RAM) or other dynamic storage device (e.g., dynamic RAM (DRAM), static RAM (SRAM), and synchronous DRAM (SDRAM)), coupled to the bus 2002 for storing information and instructions to be executed by processor 2003. In addition, the main memory 2004 may be used for storing temporary variables or other intermediate information during the execution of instructions by the processor 2003. The computer system 2001 further includes a read only memory (ROM) 2005 or other static storage device (e.g., programmable ROM (PROM), erasable PROM (EPROM), and electrically erasable PROM (EEPROM)) coupled to the bus 2002 for storing static information and instructions for the processor 2003.

The computer system 2001 also includes a disk controller 2006 coupled to the bus 2002 to control one or more storage devices for storing information and instructions, such as a magnetic hard disk 2007, and a removable media drive 2008 (e.g., floppy disk drive, read-only compact disc drive, read/write compact disc drive, compact disc jukebox, tape drive, and removable magneto-optical drive). The storage devices may be added to the computer system 2001 using an appropriate device interface (e.g., small computer system interface (SCSI), integrated device electronics (IDE), enhanced-IDE (E-IDE), direct memory access (DMA), or ultra-DMA).

The computer system 2001 may also include special purpose logic devices (e.g., application specific integrated circuits (ASICs)) or configurable logic devices (e.g., simple programmable logic devices (SPLDs), complex programmabl& logic devices (CPLDs), and field programmable gate arrays (FPGAs)).

The computer system 2001 may also include a display controller 2009 coupled to the bus 2002 to control a display 2010, such as a cathode ray tube (CRT), for displaying information to a computer user. The computer system includes input devices, such as a keyboard 2011 and a pointing device 2012, for interacting with a computer user and providing information to the processor 2003. The pointing device 2012, for example, may be a mouse, a trackball, or a pointing stick for communicating direction information and command selections to the processor 2003 and for controlling cursor movement on the display 2010. In addition, a printer may provide printed listings of data stored and/or generated by the computer system 2001.

The computer system 2001 performs a portion or all of the processing steps of the invention in response to the processor 2003 executing one or more sequences of one or more instructions contained in a memory, such as the main memory 2004. Such instructions may be read into the main memory 2004 from another computer readable medium, such as a hard disk 2007 or a removable media drive 2008. One or more processors in a multi-processing arrangement may also be employed to execute the sequences of instructions contained in main memory 2004. In alternative embodiments, hard-wired circuitry may be used in place of or in combination with software instructions. Thus, embodiments are not limited to any specific combination of hardware circuitry and software.

As stated above, the computer system 2001 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 2001, for driving a device or devices for implementing the invention, and for enabling the computer system 2001 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), JAVA classes, and complete executable programs. Moreover, parts of the processing of the present invention may be distributed for better performance, reliability, and/or cost.

The term "computer readable medium" as used herein refers to any medium that participates in providing instructions to the processor 2003 for execution. A computer readable medium may take many forms, including but not limited to, non-volatile media, volatile media, and transmission media. Non-volatile media includes, for example, optical, magnetic disks, and magneto-optical disks, such as the hard disk 2007 or the removable media drive 2008. Volatile media includes dynamic memory, such as the main memory 2004. Transmission media includes coaxial cables, copper wire and fiber optics, including the wires that make up the bus 2002. Transmission media also may also take the form of acoustic or light waves, such as those generated during radio wave and infrared data communications.

Various forms of computer readable media may be involved in carrying out one or more sequences of one or more instructions to processor 2003 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 2001 may receive the data on the telephone line and use an infrared transmitter to convert the data to an infrared signal. An infrared detector coupled to the bus 2002 can receive the data carried in the infrared signal and place the data on the bus 2002. The bus 2002 carries the data to the main memory 2004, from which the processor 2003 retrieves and executes the instructions. The instructions received by the main memory 2004 may optionally be stored on storage device 2007 or 2008 either before or after execution by processor 2003.

The computer system 2001 also includes a communication interface 2013 coupled to the bus 2002. The communication interface 2013 provides a two-way data communication coupling to a network link 2014 that is connected to, for example, a local area network (LAN) 2015, or to another communications network 2016 such as the Internet. For example, the communication interface 2013 may be a network interface card to attach to any packet switched LAN. As another example, the communication interface 2013 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 2013 sends and receives electrical, electromagnetic or optical signals that carry digital data streams representing various types of information.

The network link 2014 typically provides data communication through one or more networks to other data devices. For example, the network link 2014 may provide a connection to another computer through a local network 2015 (e.g., a LAN) or through equipment operated by a service provider, which provides communication services through a communications network 2016. The local network 2014 and communications network 2016 use, for example, electrical, electromagnetic, or optical signals that carry digital data streams, and the associated physical layer (e.g., CAT 5 cable, coaxial cable, optical fiber, etc). The signals through the various networks and the signals on the network link 2014 and through the communication interface 2013, which carry the digital data to and from the computer system 2001 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 2001 can transmit and receive data, including program code, through the network(s) 2015 and 2016, the network link 2014, and the communication interface 2013. Moreover, the network link 2014 may provide a connection through a LAN 2015 to a mobile device 2017 such as a personal digital assistant (PDA) laptop computer, or cellular telephone.

The system of certain embodiments of the present invention can be implemented in hardware, software, firmware, or a combination thereof. In the preferred embodiment, the system is implemented in software that is stored in a memory and that is executed by a suitable instruction execution system. If implemented in hardware, as in an alternative embodiment, the system can be implemented with any technology, which is all well known in the art.

Any process descriptions or blocks in the flow charts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and described by the following claims.

REFERENCES

Cutler, D. J., Zwick, M. E., Carrasquillo, M. M., Yohn, C. T., Tobin, K. P., Kashuk, C., Mathews, D. J., Shah, N. A., Eichler, E. E., Warrington, J. A., Chakravarti, A. 2001. High-throughput variation detection and genotyping using microarrays. *Genome Res* 11:1913-25

Eddy, S. R. 1998. Profile Hidden Markov Models. *Bioinformatics* 14:755-763

Korf, I., Yandell, M., Bedell, J. 2003. BLAST. O'Reilly and Associates, Sebastopol, Calif.

Kozal, M. J., Shah, N., Shen, N., Yang, R., Fucini, R., Merigan, T. C., Richman, D. D., Morris, D., Hubbell, E., Chee, M., Gingeras, T. R. 1996. Extensive polymorphisms observed in HIV-1 clade B protease gene using high-density oligonucleotide arrays. *Nat Med* 2:753-9

Leipzig, J., Pevzner, P., Heber, S. 2004. The Alternative Splicing Gallery (ASG): bridging the gap between genome and transcriptome. *Nucleic Acids Research* 32:3977-3983

Shendure, J., Mitra, R. D., Varma, C., Church, G. M. 2004. Advanced sequencing technologies: methods and goals. *Nat Rev Genet* 5:335-44

Stenger, D. A., Andreadis, J. D., Vora, G. J., Pancrazio, J. J. 2002. Potential applications of DNA microarrays in biodefense-related diagnostics. *Curr Opin Biotechnol* 13:208-12

Thompson, J. D., Gibson, T. J., Plewniak; F., Jeanmougin, F., Higgins, D. G. 1997. The CLUSTAL_X windows interface: flexible strategies for multiple sequence alignment aided by quality analysis tools. *Nucleic Acids Res* 25:4876-82

Thompson, J. D., Higgins, D. G., Gibson, T. J. 1994. CLUSTAL W: improving the sensitivity of progressive multiple sequence alignment through sequence weighting, position-specific gap penalties and weight matrix choice. *Nucleic Acids Res* 22:4673-80

The invention claimed is:

1. A computer-implemented method for generating biological sequence data for input to a query for identification of a predetermined biological sequence, comprising the steps of:
   detecting, with a processor-implemented process, a plurality of partial sequences from the predetermined biological sequence stored in memory;
      wherein the predetermined biological sequence represents one or more nucleotide sequences;
   comparing each respective partial sequence detected in the detecting step with a plurality of reference sequences;
   combining the partial sequences as a composite set of sequence data based on the results of the comparing step; and
   selecting a subsequence of the composite set of sequence data to be submitted in a query to identify a gene corresponding to the predetermined biological sequence within a predetermined confidence level;
      wherein the method is performed using a suitably programmed computer; and
      wherein the detecting step comprises:
         scanning the predetermined biological sequence to detect a series of base calls located between a consecutive series of non-base calls;
            wherein a non-base call is an unknown that represents adenine, thymine, cytosine, or guanine or a gap; and
         extracting the series of base calls as one of the plurality of partial sequences.

2. The computer-implemented method of claim 1, wherein the detecting step comprises:
   initiating a viewing window at a location of a detected valid base call;
   expanding the size of the viewing window to extend to a consecutive series of non-base calls; and
   extracting the windowed series of base calls as one of the plurality of partial sequences.

3. The computer-implemented method of claim 1, wherein the partial sequence comprises a plurality of both valid base calls and non-base calls.

4. The computer-implemented method of claim 1, wherein the comparing step comprises:
   determining for each partial sequence a statistical level of similarity between each of the plurality of partial sequences and at least one of the plurality of reference sequences,
      wherein the statistical level of similarity indicates a level of correspondence between each of the plurality of partial sequences and the at least one of the plurality of reference sequences.

5. The computer-implemented method of claim 4, wherein the combining step comprises:
   extracting each of the plurality of partial sequences determined to have a statistical level of similarity with at least one of the plurality of reference sequences above a predetermined threshold; and
   linearly combining each of the plurality of extracted sequences to create a composite set of sequence data.

6. The computer-implemented method of claim 1, wherein the selecting step further comprises:
   selecting a window size parameter corresponding to a number of base calls in the composite set of sequence data; and
   calculating a percentage of valid base calls contained within a viewing window of the composite set of sequence data, the size of the window corresponding to the window size parameter selected in the selecting step.

7. The computer-implemented method of claim 6, wherein the selecting step further comprises:
   sliding the viewing window to another number of base calls in the composite set of sequence data when the percentage calculated in the calculating step does not satisfy a predetermined threshold; and
   calculating a percentage of valid base calls contained within the composite set of sequence data.

8. The computer-implemented method of claim 6, wherein the selecting step comprises:
   selecting a subsequence of base calls within a viewing window as the subsequence submitted in the query when the calculated percentage satisfied a predetermined threshold.

9. The computer-implemented method of claim 8, further comprising the step of:
   trimming non-base calls from the selected subsequence of base calls before the selected subsequence is submitted in the query.

10. The computer-implemented method of claim 1, further comprising:
    comparing the subsequence with a plurality of predetermined sequences; and
    generating comparison results corresponding to at least one of said predetermined sequences.

11. The computer implemented method of claim 10, wherein comparison results from the comparing step include a statistical value indicating a predetermined level of correspondence between the subsequence and the at least one of said predetermined sequences.

12. A computer readable storage medium configured to store computer readable instructions for execution on a computer, the computer readable instructions, when executed by the computer, configured to perform a method for generating biological sequence data for input to a query for identification of a predetermined biological sequence, comprising the steps of:
    detecting, with a processor-implemented process, a plurality of partial sequences from the predetermined biological sequence stored in memory;
       wherein the predetermined biological sequence represents one or more nucleotide sequences;
    comparing each respective partial sequence detected in the detecting step with a plurality of reference sequences;
    combining the partial sequences as a composite set of sequence data based on the results of the comparing step; and
    selecting a subsequence of the composite set of sequence data to be submitted in a query to identify a gene corresponding to the predetermined biological sequence within a predetermined confidence level;
       wherein the steps are performed using a suitably programmed computer; and
       wherein the detecting step comprises:
          scanning the predetermined biological sequence to detect a series of base calls located between a consecutive series of non-base calls;
             wherein a non-base call is an unknown that represents adenine, thymine, cytosine, or guanine or a gap; and
          extracting the series of base calls as one of the plurality of partial sequences.

13. An apparatus for generating biological sequence data for input to a query for identification of a predetermined biological sequence, comprising:

means for detecting, with a processor-implemented process, a plurality of partial sequences from the predetermined biological sequence stored in memory;
   wherein the predetermined biological sequence represents one or more nucleotide sequences;
means for comparing each respective partial sequence detected by the means for detecting with a plurality of reference sequences;
means for combining the partial sequences as a composite set of sequence data based on the results from the means for comparing; and
means for selecting a subsequence of the composite set of sequence data to be submitted in a query to identify a gene corresponding to the predetermined biological sequence within a predetermined confidence level;
   wherein the means are a suitably programmed computer; and
   wherein the detecting comprises:
      scanning the predetermined biological sequence to detect a series of base calls located between a consecutive series of non-base calls;
         wherein a non-base call is an unknown that represents adenine, thymine, cytosine, or guanine or a gap; and
      extracting the series of base calls as one of the plurality of partial sequences.

14. The computer-implemented method of claim 1, further comprising:
   submitting the subsequence of the composite set of sequence data in a query to a database using a similarity search algorithm.

* * * * *

SEQUENCE LISTING

```
<160> NUMBER OF SEQ ID NOS: 46

<210> SEQ ID NO 1
<211> LENGTH: 1234
<212> TYPE: DNA
<213> ORGANISM: Unknown
<220> FEATURE:
<223> OTHER INFORMATION: Microarray base call pattern
      Ad4FIBER:609124A2-8.7.03- 2hour hybridization; obtained from
      partial hybridization of Human Adenovirus Type 4 (strain unknown)
      fiber gene sequence fragments
<220> FEATURE:
<221> NAME/KEY: Unsure
<222> LOCATION: (1)..(1234)
<220> FEATURE:
<221> NAME/KEY: misc_feature
<222> LOCATION: (1)..(1234)
<223> OTHER INFORMATION: n is a, c, g, or t

<400> SEQUENCE: 1
tcccnacgat gcagncnncn nncgacnang cccttcatca accctccctt cgnnctcttc      60
agntggnttc caagaaaagc ccctgggggt gttgnccnta ggnnntnnnc gaccctgncn     120
cnccangaat ggggaaanca cncnnantnt ggngnannnn gtggaccttg acgnctcggg     180
aaanctcntt gcaancncag ncnnnaagnn cattgnnnct nntagntttt nccancaacn     240
ccattnnnnn ttaacatggn nncccctttta nncnccaaag ntggaaanct nnccttncaa     300
gnttctnncn ccattaagta tattnngnnn nnnnnntnnn nnntnnntnn nctnnncttt     360
tngctcaggt ttnggacngn nnngnagngn tnngncagta cagttagcct ctncncttnc     420
atttgnngnn aaagggaana naaagnttnn nntnnntnnn ggnttgcatg ttacaacagg     480
aantgcaatt gaaagcaaca ttagntgggc tnaaggtnna aaatttgaag atggtgccan     540
agcnncaaac attggtaagn nntnnnnnnt nnnaaccagn agnncagaan caggagntaa     600
naangcttnn ccaanccaag ntaaanttgn atctggncnc agctttgnca gcncaggagn     660
nntaatgnct ggcaataaag ncnnnganan attancttg tggacaacgc ctgacccatc     720
annaaactgn caaatnctng cngaaaanga ngcaaancta ncnctttgct tnacnnagnn     780
ngnnagncaa atnctggcca ctgnancagn tttggntgnt agaagnggna ncntaaaccc     840
aattnctggc acagnaagca gngctcaagn ttttcnncgn tttgatgcaa ncngtgntct     900
tttancngan cactcnannn nnaaaaaata ctggggctac nggnaaggag atagcataga     960
tggcactnca tacaccaatg ctgttggntn cntgccaaat tcancagctt ntnnaaagac    1020
ncaaagttct nctnnntaaaa ataatntann nngncaagna tnnatgaatg gngntgtttn    1080
aaaacccang cttcttncta tanctcttaa tggnnctgnt gacaccacca gtgcatnntn    1140
```

```
nntttnattt tcntncacct ggactaacgg aagctanatc ggagcaacat ttggagctaa    1200
ctcatacacc ttcncntaca nngcccanna annn                                1234

<210> SEQ ID NO 2
<211> LENGTH: 337
<212> TYPE: DNA
<213> ORGANISM: Unknown
<220> FEATURE:
<223> OTHER INFORMATION: Subsequences of "Microarray base call pattern
      Ad4FIBER:609124A2-8.7.03- 2hour hybridization" as parsed by CIBSI
      algorithm with corresponding returns generated by blastn
      algorithm
<220> FEATURE:
<221> NAME/KEY: Unsure
<222> LOCATION: (1)..(337)
<220> FEATURE:
<221> NAME/KEY: misc_feature
<222> LOCATION: (1)..(337)
<223> OTHER INFORMATION: n is a, c, g, or t

<400> SEQUENCE: 2
tcccnacgat gcagncnncn nncgacnang cccttcatca accctcccctt cgnnctcttc     60 agntggnttc caagaaaagc ccctgggggt gttgnccnta ggnnntnnnc gaccctgncn    120
cnccangaat ggggaaanca cncnnantnt ggngnannnn gtggaccttg acgnctcggg    180
aaanctcntt gcaancncag ncnnnaagnn cattgnnnct nntagntttt nccancaacn    240
ccattnnnnn ttaacatggn nnccctttta nncnccaaag ntggaaanct nnccttncaa    300
gnttctnncn ccattaagta tattnngnnn nnnnnnt                             337

<210> SEQ ID NO 3
<211> LENGTH: 888
<212> TYPE: DNA
<213> ORGANISM: Unknown
<220> FEATURE:
<223> OTHER INFORMATION: Subsequences of "Microarray base call pattern
      Ad4FIBER:609124A2-8.7.03- 2hour hybridization" as parsed by CIBSI
      algorithm with corresponding returns generated by blastn
      algorithm
<220> FEATURE:
<221> NAME/KEY: Unsure
<222> LOCATION: (1)..(888)
<220> FEATURE:
<221> NAME/KEY: misc_feature
<222> LOCATION: (1)..(888)
<223> OTHER INFORMATION: n is a, c, g, or t

<400> SEQUENCE: 3
tnnntnnnct nnnctttttng ctcaggtttn ggacngnnnn gnagngntnn gncagtacag     60
ttagcctctn cncttncatt tgnngnnaaa gggaananaa agnttnnnnt nnntnnnggn    120
ttgcatgtta caacaggaan tgcaattgaa agcaacatta gntgggctna aggtnnaaaa    180
tttgaagatg gtgccanagc nncaaacatt ggtaagnnnt nnnnnntnnn aaccagnagn    240
ncagaancag gagntaanaa ngcttnncca anccaagnta aanttgnatc tggncncagc    300
tttgncagcn caggagnnnt aatgnctggc aataaagncn nnganaaatt ancttttgtgg    360 acaacgcctg acccatcann aaactgncaa atnctngcng aaaangangc aaanctancn    420
ctttgcttna cnnagnnngn nagncaaatn ctggccactg nancagntt t ggntgntaga    480 agnggnancn taaacccaat tnctggcaca gnaagcagng ctcaagntt t tcnncgnttt    540 gatgcaancn gtgntctttt ancngancac tcnannnnna aaaatactg gggctacngg    600 naaggagata gcatagatgg cactncatac accaatgctg ttggntncnt gccaaattca    660
ncagcttntn naaagacnca aagttctnct nntaaaaata atntannnng ncaagnatnn    720
```

-continued

```
atgaatgggng ntgtttnaaa acccangctt cttnctatan ctcttaatgg nnctgntgac    780
accaccagtg catnntnnnt ttnattttcn tncacctgga ctaacggaag ctanatcgga    840
gcaacatttg gagctaactc atacaccttc ncntacanng cccannaa               888
```

<210> SEQ ID NO 4
<211> LENGTH: 916
<212> TYPE: DNA
<213> ORGANISM: Unknown
<220> FEATURE:
<223> OTHER INFORMATION: Microarray base call pattern
    Ad4E1A:097881C2-9.16.03; obtained from partial hybridization of
    Human Adenovirus Type 4 (strain unknown) E1A gene sequence
    fragment
<220> FEATURE:
<221> NAME/KEY: Unsure
<222> LOCATION: (1)..(916)
<220> FEATURE:
<221> NAME/KEY: misc_feature
<222> LOCATION: (1)..(916)
<223> OTHER INFORMATION: n is a, c, g, or t

<400> SEQUENCE: 4

```
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnntnnnnnn    240
nnnnnnnnnn nnnnnnnnnn nnnnnnnnnn nnnnnnnnnn nnnnnnnnnn nnnnnnnnnt    300
nnnnnnnnnn nnnnnnnnnn nnnnnnnnnn nnnnnnnnnn nnnnntgcnc gnncngtntn    360
ntcnggaggt ggatgtgncc gnggacgacn nnaacgagaa ggcggtaaan gatttnnttna    420 ncgatgccgc gnngctngnt gccgaggngg nttcangncc tagnncagnc agcgnctnnt    480
cactgcnnan nnntagacac gacngaggtg agaaagngat cnncgggctt aaatgggaan    540
agatggactt gcgtngcnat gaggaatgnn tgnnnnnnng cgatgatgng nacgngcngg    600
cgntnnagan cgcagcgagc catgngtgtc aagccgncag cgaganctttt ncnctngacn    660 gnnngccttt gnnnngacac ggcngnaagn cttgtgaatt tcatcgcanc aatnctggag    720
ataaagctgt gntatgnnng nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnt    840
tttnnnnnnn nnnnnnnnnn nnnnnnnnnn nnnnnnnnnn nnnnnnnnnn nnntnnnnnn    900
nnnnnnnnnn nnannn                                                    916
```

<210> SEQ ID NO 5
<211> LENGTH: 674
<212> TYPE: DNA
<213> ORGANISM: Unknown
<220> FEATURE:
<223> OTHER INFORMATION: Microarray base call pattern
    Ad4FIBER:097881C2-9.16.03; obtained from partial hybridization of
    Human Adenovirus Type 4 (strain unknown) fiber gene sequence
    fragments
<220> FEATURE:
<221> NAME/KEY: Unsure
<222> LOCATION: (1)..(674)
<220> FEATURE:
<221> NAME/KEY: misc_feature
<222> LOCATION: (1)..(674)
<223> OTHER INFORMATION: n is a, c, g, or t

<400> SEQUENCE: 5

```
nnnnnnnnnn ntnnncnnnc nccgancgnn nnnnnnnnnn nnnnnnnnnn nnnnnnnnnn     60
```

```
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnnnnnnnn nnnnnnnnnn nnnnnnnnnn       180
nnnnnnnnnn nnnnnnnnnn nnnnnnnnnn nnnnaannnn naanannnnan nnnnnnnnnn       240 ntgnnncnnn ntngnnngnn nnnanngnan annnannnnn nnnnnnnnnn nnnnnnnncn       300
gnnntcnngt ttttctacgt tnngannnaa anngnnnnnn nnnnnnnnnn nnnnnnnnnn       360
nnnnnnnnnn cngnggctac angcannnng nnngcanagn nggcactcca tacacnnnnn       420
nnntngnnnn nangcnnnnn nnnnnnnnnn nnccnnngac nnannnnnnn nnnnnnnnnn       480
nnnnnnnnnn nnnnnnnnnn nnnnnnnnnn nnnnnnnnnn nannnnnnnn nnnnnnnnnn       540
nnnnnnnnnn nnnnnngnn nnnnnnnnnn nnnnncnnn nnnnnnnnnn nnnnnnncnn       600
ngactnacng nnnctnnnnn ngngcaanan nnnnnnngaa ntnannnnnn nnnnnnnnnn       660
nnnnnnnnnn nnnn                                                         674

<210> SEQ ID NO 6
<211> LENGTH: 255
<212> TYPE: DNA
<213> ORGANISM: Unknown
<220> FEATURE:
<223> OTHER INFORMATION: Microarray base call pattern
      Ad4HEXON:097881C2-9.16.03; obtained from partial hybridization of
      Human Adenovirus Type 4 (strain unknown) hexon gene sequence
      fragments
<220> FEATURE:
<221> NAME/KEY: Unsure
<222> LOCATION: (1)..(255)
<220> FEATURE:
<221> NAME/KEY: misc_feature
<222> LOCATION: (1)..(255)
<223> OTHER INFORMATION: n is a, c, g, or t

<400> SEQUENCE: 6
nnnnnnnnnn nnnnnnnnnn nnnnnnnnnn nnnnnnnnnn nnnnnnnnnn nnnnnnnnnn        60
nnnnnnnnnn nnnnnnnnnn nnnnnnnnna nnnnnnnnnn nnnnnnnnnn nnnnnnnnnn       120
nannnnnnnn nnnngnnnn nnnnnnnnnn nnnnnnnnnn nnnnnnnnnn nnnnnnnnnn       180
nnnnnnnnnn nnnnnnnnnn nnnnnnnnnn nnnnnnnnnn nnnncngacn nnnnnnncnn       240
nnnnnnnnnn nnnnn                                                        255

<210> SEQ ID NO 7
<211> LENGTH: 160
<212> TYPE: DNA
<213> ORGANISM: Unknown
<220> FEATURE:
<223> OTHER INFORMATION: Microarray base call pattern
      Ad5E1A:097881C2-9.16.03; obtained from partial hybridization of
      Human Adenovirus Type 5 (strain unknown) E1A gene sequence
      fragments
<220> FEATURE:
<221> NAME/KEY: Unsure
<222> LOCATION: (1)..(160)
<220> FEATURE:
<221> NAME/KEY: misc_feature
<222> LOCATION: (1)..(160)
<223> OTHER INFORMATION: n is a, c, g, or t

<400> SEQUENCE: 7
nagnctnnnn tccggtttcn ntgccnannc nngtnccgnn ggtgnncgan cttacctgnn        60
acgannnntg ctttncncnc ngtgncnncg agnntgangn nnntgngnag tttgtgntag       120
nttatgngga ncannnnnng canggttgca ggtcntgnca                             160

<210> SEQ ID NO 8
```

```
<211> LENGTH: 47
<212> TYPE: DNA
<213> ORGANISM: Unknown
<220> FEATURE:
<223> OTHER INFORMATION: Hypothetical microarray base call pattern used
      to graphically illustrate sliding window algorithm
<220> FEATURE:
<221> NAME/KEY: Unsure
<222> LOCATION: (1)..(47)
<220> FEATURE:
<221> NAME/KEY: misc_feature
<222> LOCATION: (1)..(47)
<223> OTHER INFORMATION: n is a, c, g, or t

<400> SEQUENCE: 8
nnnnnnntcg atcngatcng atatncgagc gnnnnnnnnn nnnnnnn                    47

<210> SEQ ID NO 9
<211> LENGTH: 556
<212> TYPE: DNA
<213> ORGANISM: Unknown
<220> FEATURE:
<223> OTHER INFORMATION: subsequence selected from "Microarray base call
      pattern Ad4E1A:Ad4 Prototype-serial dilution1 following
      hybridization with human adenovirus type 4 DNA" as parsed by CIBSI
      algorithm with corresponding returns generated by blastn algorithm
<220> FEATURE:
<221> NAME/KEY: Unsure
<222> LOCATION: (1)..(556)
<220> FEATURE:
<221> NAME/KEY: misc_feature
<222> LOCATION: (1)..(556)
<223> OTHER INFORMATION: n is a, c, g, or t

<400> SEQUENCE: 9
cacctncgct gcncgancng tatgatctgg nggtggatgt gnccgaggac gacnncaacg       60
agaaggcggt aaatgattta tttagcgatg ccgcgctgct agctgncgag gnggcttcaa     120
gncctagctc agacagcgac tcttcactgc ataccectag ncacgncaga ggtgagaaag     180
agatccccgg gcttaaatgg gaaaagntgg acttgcgttg ctatgaggaa tgnctgnnnn     240
caagcgatga tgaggacgag cnggcgnttc agancgcagc gagccatgna gtgcaagccg     300
tcagcgagag ctttgcactg gacngcccgc ctttgcncgg acacggctgt aagtcttgtg     360
aatttcatcg cancaatact ggagataaag ctgtgttatg tgcgctttgc tatatgagag     420
cgnacaacca ttgtgtttnc agtaagtgtg attaagtgaa ctttnaangg aggcaaanag     480
tagngtgact nngtgatgac tnnttttnttt ntntntntnt nttttttwtn tnnktnynnt     540
ttytnnnnnn nntknt                                                    556

<210> SEQ ID NO 10
<211> LENGTH: 1116
<212> TYPE: DNA
<213> ORGANISM: Unknown
<220> FEATURE:
<223> OTHER INFORMATION: subsequence selected from "Microarray base call
      pattern Ad4FIBER:Ad4 Prototype-serial dilution1 following
      hybridization with human adenovirus type 4 DNA"
<220> FEATURE:
<221> NAME/KEY: Unsure
<222> LOCATION: (1)..(1116)
<220> FEATURE:
<221> NAME/KEY: misc_feature
<222> LOCATION: (1)..(1116)
<223> OTHER INFORMATION: n is a, c, g, or t

<400> SEQUENCE: 10
annanntnnn ccnccaccga ncgtgncctt catcaacnct cccttcnnnn nnttcagntg       60
gattccaaga aaagcccctg gnggtgttgt ccnnngggnn tgnncgacnc tgtcncncca     120
```

```
agaatgggga aattaccctc aagntnnnnn annnnnnnga ncttgncgnc tcgggnaanc        180
tcattgcaaa cncagnaaac aaggccattg nnnntctcag tttttyccaa caacaccatt        240
tnnnnttaac atggntaccc ctttatncac caaagatgga aaactanccct tacaagtttc       300 tnccaccant aagnannntta aaancaacaa ttttgaatnc annannmnnn ncttttggct       360
caggtttagg nctcagtgnc agcgnccctgn cagtacagtt agcctctcca cttncatttg       420
ntgataaagg gaatataaag attaccctaa acaggngntt gcatgttnca ncaggagntg        480
caattgaaag caacatcagt tgggctaaag gtataaaatt tgaagntggt gccatagcta        540
caaacattgg taagnnsnnn ngnktnggaa ccagnagtnc agaaacagga gttaataatg        600
cttatccaat ccaagttaaa cttggctctg gtctcagctt tgncagcaca ggagccataa        660
tggctggcaa taaagnctat gataaattaa ctttgtggac aacgcctgac ccatcaccaa        720
actgncaaat actngcagaa aatgntgcaa aactancact ttgcnnaann aannnngaca        780
gncaaatnct ggccactgta kcngntttgg ntgttagaag tggaaactta aacccaatta        840
ctggcacagt aagcagtgct caagttttttc tacgttttga tgcaaatggt gttcttttaa       900
cagaacactc nanncnnaaa aaatnctggg gctacaagca aggagatagc atagntggca        960
ctncatacac caatgctgtt ggttttatgc caaattcaac agcttatcca aagacccaaa       1020
gttctactnn taaaaataat atagtgggtc aagtatacat gaatggagnt gtttcaaaac       1080
ccatgcttct tactataact cttaatggta ctgatg                                 1116

<210> SEQ ID NO 11
<211> LENGTH: 150
<212> TYPE: DNA
<213> ORGANISM: Human adenovirus type 4
<220> FEATURE:
<221> NAME/KEY: gene
<222> LOCATION: (1)..(150)
<223> OTHER INFORMATION: Ad4FS_AF_hexon
<220> FEATURE:
<221> NAME/KEY: misc_feature
<222> LOCATION: (1)..(150)
<223> OTHER INFORMATION: n is a, c, g, or t

<400> SEQUENCE: 11
agtggaagga tgctaannnn nnncagcaan nnnnnnnnnn nnnnnnnaat gcnnnnnnnn         60
nnnnnnnnnn nnnnnnnnnn nnnnnnnnnn nnnnnnnnna tacctnttgg ggtnnnnnnn        120
nagctgccat gccaggtgtt acnnnnnnnn                                        150

<210> SEQ ID NO 12
<211> LENGTH: 150
<212> TYPE: DNA
<213> ORGANISM: Human adenovirus type 4
<220> FEATURE:
<221> NAME/KEY: gene
<222> LOCATION: (1)..(150)
<223> OTHER INFORMATION: Ad4FS_army_hexon
<220> FEATURE:
<221> NAME/KEY: misc_feature
<222> LOCATION: (1)..(150)
<223> OTHER INFORMATION: n is a, c, g, or t

<400> SEQUENCE: 12
agtggaagga tgctaannnn nnncagcaan nnnnnnnnnn nnnnnnnaat gcnnnnnnnn         60
nnnnnnnnnn nnnnnnnnnn nnnnnnnnnn nnnnnnnnna tacctnttgg ggtnnnnnnn        120
nagctgccat gccaggtgtt acnnnnnnnn                                        150
```

```
<210> SEQ ID NO 13
<211> LENGTH: 150
<212> TYPE: DNA
<213> ORGANISM: Human adenovirus type 4
<220> FEATURE:
<221> NAME/KEY: gene
<222> LOCATION: (1)..(150)
<223> OTHER INFORMATION: Ad4vaccine_hexon
<220> FEATURE:
<221> NAME/KEY: misc_feature
<222> LOCATION: (1)..(150)
<223> OTHER INFORMATION: n is a, c, g, or t

<400> SEQUENCE: 13
agtggaagga ttctgannnn nnncagcaan nnnnnnnnnn nnnnnnnaat gcnnnnnnnn      60
nnnnnnnnnn nnnnnnnnnn nnnnnnnnnn nnnnnnnnna tacctnttgg ggcnnnnnnn     120
nagctgccat gcccggtgtt acnnnnnnnn                                      150

<210> SEQ ID NO 14
<211> LENGTH: 150
<212> TYPE: DNA
<213> ORGANISM: Human adenovirus type 4
<220> FEATURE:
<221> NAME/KEY: gene
<222> LOCATION: (1)..(150)
<223> OTHER INFORMATION: Ad4_hexon
<220> FEATURE:
<221> NAME/KEY: misc_feature
<222> LOCATION: (1)..(150)
<223> OTHER INFORMATION: n is a, c, g, or t

<400> SEQUENCE: 14
agtggaagga ttctgannnn nnncagcaan nnnnnnnnnn nnnnnnnaat gcnnnnnnnn      60
nnnnnnnnnn nnnnnnnnnn nnnnnnnnnn nnnnnnnnna tacctnttgg ggcnnnnnnn     120
nagctgccat gcccggtgtt acnnnnnnnn                                      150

<210> SEQ ID NO 15
<211> LENGTH: 150
<212> TYPE: DNA
<213> ORGANISM: Human adenovirus type 16
<220> FEATURE:
<221> NAME/KEY: gene
<222> LOCATION: (1)..(150)
<223> OTHER INFORMATION: Ad16_hexon
<220> FEATURE:
<221> NAME/KEY: misc_feature
<222> LOCATION: (1)..(150)
<223> OTHER INFORMATION: n is a, c, g, or t

<400> SEQUENCE: 15
agtggaagga ttctgannnn nnncagcaan nnnnnnnnnn nnnnnnnaat gcnnnnnnnn      60
nnnnnnnnnn nnnnnnnnnn nnnnnnnnnn nnnnnnnnna tacctnttgg ggtnnnnnnn     120
nagctgccat gcccggtgtt acnnnnnnnn                                      150

<210> SEQ ID NO 16
<211> LENGTH: 150
<212> TYPE: DNA
<213> ORGANISM: Human adenovirus type 3
<220> FEATURE:
<221> NAME/KEY: gene
<222> LOCATION: (1)..(150)
<223> OTHER INFORMATION: Ad3FS_navy_hexon
<220> FEATURE:
<221> NAME/KEY: misc_feature
<222> LOCATION: (1)..(150)
<223> OTHER INFORMATION: n is a, c, g, or t

<400> SEQUENCE: 16
```

```
agtggatagt tacaacnnnn gnnaatcgan nnnnnnnnnn nnnngacaat gcagtaacta    60
ccaccacnnn nnnnnnnnnn nnnnnnnnnn nnnnnnnaaa cacatnttgg catnnnnnnn   120
ntgcttccat gaaggnngag acnnnnnnnn                                   150
```

```
<210> SEQ ID NO 17
<211> LENGTH: 150
<212> TYPE: DNA
<213> ORGANISM: Human adenovirus type 3
<220> FEATURE:
<221> NAME/KEY: gene
<222> LOCATION: (1)..(150)
<223> OTHER INFORMATION: Ad3_hexon
<220> FEATURE:
<221> NAME/KEY: misc_feature
<222> LOCATION: (1)..(150)
<223> OTHER INFORMATION: n is a, c, g, or t

<400> SEQUENCE: 17
agtggatagt tacaacnnnn annaatgggn nnnnnnnnnn nnnngacaat gcagtaacta    60
ccaccacnnn nnnnnnnnnn nnnnnnnnnn nnnnnnnaaa cacatnttgg catnnnnnnn   120
ntgcttccat gaaggnngag acnnnnnnnn                                   150
```

```
<210> SEQ ID NO 18
<211> LENGTH: 150
<212> TYPE: DNA
<213> ORGANISM: Human astrovirus type 7
<220> FEATURE:
<221> NAME/KEY: gene
<222> LOCATION: (1)..(150)
<223> OTHER INFORMATION: Ad7_hexon
<220> FEATURE:
<221> NAME/KEY: misc_feature
<222> LOCATION: (1)..(150)
<223> OTHER INFORMATION: n is a, c, g, or t

<400> SEQUENCE: 18
agtggatagt tacagcnnnn annggagaan nnnnnnnnnn nnnngaaaga gcagtaacta    60
ccaccacnnn nnnnnnnnnn nnnnnnnnnn nnnnnnnaaa cacatnttgg catnnnnnnn   120
ntgcttccat gaaggnngag acnnnnnnnn                                   150
```

```
<210> SEQ ID NO 19
<211> LENGTH: 150
<212> TYPE: DNA
<213> ORGANISM: Human astrovirus type 7
<220> FEATURE:
<221> NAME/KEY: gene
<222> LOCATION: (1)..(150)
<223> OTHER INFORMATION: Ad7FS_navy_hexon
<220> FEATURE:
<221> NAME/KEY: misc_feature
<222> LOCATION: (1)..(150)
<223> OTHER INFORMATION: n is a, c, g, or t

<400> SEQUENCE: 19
agtggatagt tacaacnnnn gnnggagaan nnnnnnnnnn nnnngacaat gcnnnnnnnn    60
ncaccacnnn nnnnnnnnnn nnnnnnnnnn nnnnnnnata cacatnttgg catnnnnnnn   120
ntgcttccac gaaggnngag acnnnnnnnn                                   150
```

```
<210> SEQ ID NO 20
<211> LENGTH: 150
<212> TYPE: DNA
<213> ORGANISM: Human astrovirus type 7
<220> FEATURE:
<221> NAME/KEY: gene
```

```
<222> LOCATION: (1)..(150)
<223> OTHER INFORMATION: Ad7vaccine_hexon
<220> FEATURE:
<221> NAME/KEY: misc_feature
<222> LOCATION: (1)..(150)
<223> OTHER INFORMATION: n is a, c, g, or t

<400> SEQUENCE: 20
agtggatagt tacaacnnnn gnnggagaan nnnnnnnnnn nnnngacaat gcnnnnnnnn      60
ncaccacnnn nnnnnnnnnn nnnnnnnnnn nnnnnnnata cacatnttgg catnnnnnnn     120
ntgcttccac gaaggnngag acnnnnnnnn                                      150

<210> SEQ ID NO 21
<211> LENGTH: 150
<212> TYPE: DNA
<213> ORGANISM: Human adenovirus type 21
<220> FEATURE:
<221> NAME/KEY: gene
<222> LOCATION: (1)..(150)
<223> OTHER INFORMATION: Ad21_hexon
<220> FEATURE:
<221> NAME/KEY: misc_feature
<222> LOCATION: (1)..(150)
<223> OTHER INFORMATION: n is a, c, g, or t

<400> SEQUENCE: 21
agtggattgc tgaaggcgtn annaaaaaan nnnnnnnnnn nnnngaagat gggggatctg      60
acgaagagga agagaaaaat ctcannnnnn nnnccactta cacttnttgg aaannnnnnn     120
ntgccccagt gaaagcagaa ggnnnnnnnn                                      150

<210> SEQ ID NO 22
<211> LENGTH: 150
<212> TYPE: DNA
<213> ORGANISM: Human adenovirus type 50
<220> FEATURE:
<221> NAME/KEY: gene
<222> LOCATION: (1)..(150)
<223> OTHER INFORMATION: Ad50_hexon
<220> FEATURE:
<221> NAME/KEY: misc_feature
<222> LOCATION: (1)..(150)
<223> OTHER INFORMATION: n is a, c, g, or t

<400> SEQUENCE: 22
agtggcttaa taagggnnnn anngatgaan nnnnnnnnnn nnnngaggat ggggaannng      60
acgaccaaca agnnnnnnnn nnnnnnnnnn nnnctacata cacttnttgg caannnnnnn     120
ntgcgccagt aaaagccgaa gcnnnnnnnn                                      150

<210> SEQ ID NO 23
<211> LENGTH: 150
<212> TYPE: DNA
<213> ORGANISM: Human adenovirus type 34
<220> FEATURE:
<221> NAME/KEY: gene
<222> LOCATION: (1)..(150)
<223> OTHER INFORMATION: Ad34_hexon
<220> FEATURE:
<221> NAME/KEY: misc_feature
<222> LOCATION: (1)..(150)
<223> OTHER INFORMATION: n is a, c, g, or t

<400> SEQUENCE: 23
agtggttgga taagggagtt anncaagcac tggnnnncct agtggacgac ggcaatactg      60
atgatgggga agaagccaaa aaagnnnnnn nnncaacata cacttnttgg taannnnnnn     120
ntgctccagt aaaagccgag gcnnnnnnnn                                      150
```

<210> SEQ ID NO 24
<211> LENGTH: 150
<212> TYPE: DNA
<213> ORGANISM: Human adenovirus type 1
<220> FEATURE:
<221> NAME/KEY: gene
<222> LOCATION: (1)..(150)
<223> OTHER INFORMATION: Ad1_hexon
<220> FEATURE:
<221> NAME/KEY: misc_feature
<222> LOCATION: (1)..(150)
<223> OTHER INFORMATION: n is a, c, g, or t

<400> SEQUENCE: 24

```
agtgggaaca agaagaacca actcaggaaa tggctgaaga acttgaagat gaggaggagg      60
cagaggagga ggaggcagag gaggaggcag aagcaccaca agctgatcag aaggttaaga     120
agactcatgt atatgctcag gctcctttgg                                      150
```

<210> SEQ ID NO 25
<211> LENGTH: 150
<212> TYPE: DNA
<213> ORGANISM: Human adenovirus type 5
<220> FEATURE:
<221> NAME/KEY: gene
<222> LOCATION: (1)..(150)
<223> OTHER INFORMATION: Ad5FS_hexon
<220> FEATURE:
<221> NAME/KEY: misc_feature
<222> LOCATION: (1)..(150)
<223> OTHER INFORMATION: n is a, c, g, or t

<400> SEQUENCE: 25

```
aatgggatga agctgctact gctcttgaaa tnnnnnnaaa cctagaagaa gaggacgatg      60
acaacgaaga cgaagtagac gagnnnnnnn nnnnnnnnca agctgagcag caannnnnna     120
aaactcacgt atttgggcag gcgccttatt                                      150
```

<210> SEQ ID NO 26
<211> LENGTH: 2940
<212> TYPE: DNA
<213> ORGANISM: Human adenovirus type 4
<220> FEATURE:
<221> NAME/KEY: misc_feature
<222> LOCATION: (1)..(2940)
<223> OTHER INFORMATION: hypothetical consensus sequence constructed
      from the 15 previously described sequences n is a, c, g, or t

<400> SEQUENCE: 26

```
atggccaccc catcgatgat gccccagtgg gcatacatgc acatcgccgg acaggatgct      60
tcggagtacc tgagtccggg tctggtgcag ttcgcccgcg ccacagacac ctacttcagt     120
ctggggaaca gtttagaaa ccccacggtg gcgcccaccc acgatgtgac caccgaccgt     180
agccagcggc tgatgctgcg cttcgtgccc gttgaccggg aggacaatac ctactcttac     240
aaagtgcgct acacgctggc tgtgggcgac aacagagtgc tggacatggc cagcacattc     300
tttgacattc ggggcgtgct ggatagaggc cctagcttca agccctactc cggcactgct     360
tacaactcac tggctcctaa gggcgcgccc aatacatctc agtggatgga tacagannnt     420
actcaggaaa tggnnnnana actngacaat gcngnaactg ncaccacgga agangnanan     480
nangnnnnnn nncnacata cacctattgg catnnnnnna atgctgccat gaaaggtgag     540
acnccttnnn ctgggaaaat tactaaagat gaaggtctgc caattggaat agatattact     600
nctactgaag gagangacaa accaattat gctgataaaa cttatcaacc agaacctcaa     660
```

```
gttggagaag aaacttggac tgacactgat ggaacaaatg aaaaatatgg anggcagagc    720
tctaaaacca gctactaaaa tgaaaccctg ctacgggtct tttgccaaac ctacaaacat    780 aaaaggggt caggctaaaa taaaagnaat caaaaacaac aaccgaagga gccatngatc     840
ctgagtatcc agatattgat atgngaattt tttgacggta aaaatactgt tgnagctgac    900
ttcgatcctg aaattgtaat gtacacagaa aatgttgatt tggaaactcc agacactcat    960
gttgtataca aacctggaac ttcggatgcn agctctcatg caaatttggg tcaacaagcc    1020
atgcctaaca gacccaacta cattggcttc agggacaact ttatcgggct catgtactac    1080
aacagtactg gcaatatggg agttctggcc ggccaagcat ctcagctgaa tgcagtggtt    1140
gacttgcagg acagaaacac tgaactgtca tatcagctct tgcttgattc tctgggtgac    1200
agaaccagat acttcagtat gtggaatcag gctgtggaca gctatgatcc tgatgtgcgc    1260
attattgaaa atcatggtgt ggaggatgaa ctgccaaact actgctttcc gttggatggt    1320
gtaggtcnac caacagacac ttaccaaggt attaaagtta aaacagatga aantnctgaa    1380
tnnnnnnnnn nnnagtggga caaagatgnt aacgcagtta gaactgctaa tgaaatagct    1440
gtaggcaatc cttttgccat ggaaattaac atccaagcca acctgtggag aagtttcctg    1500
tattccaatg tggctctgta tctgccagat aattacaaat acacgccagc caacatcact    1560
ctgcccacta acaccaacac ctacgagtac atgaacgggc gggtggtggc cccatcgctg    1620
gtggattcct acattaacat tggcgccagg tggtctctgg accccatgga caatgtcaat    1680
ccattcaacc accaccgcaa tgctggcctg cgctaccggt ccatgcttct gggcaatggt    1740
cgttatgtgc ctttccacat acaagtgcct cagaaattct ttgctgtcaa gaacctactg    1800
cttctacccg gctcctacac ctacgagtgg aacttcagaa aggatgtgaa catggtcctg    1860
cagagttccc ttggaaatga cctccgaaca gatggtgcca ccataagttt caccagcatc    1920
aacctctatg ccaccttctt ccccatggct cacaacaccg cctccaccct tgaagccatg    1980
ctgcgcaacg acaccaatga tcagtcattc aacgactacc tctctgcagc caacatgctc    2040
taccccatcc ctgccaatgc aaccaacgtt cccatctcca tccctctcg caactgggcc    2100 gccttcagcg gctggtcctt caccagactc aaaaccaagg agactccctc tctgggatca    2160
gggttcgacc cctacttcgt ctactctggc tctattccct acctggatgg cacctttttac   2220 cttaaccaca ctttcaagaa ggtctccatc atgtttgact cttcagtcag ctggcctggc    2280
aatgacaggc tgctgactcc aaacgagttt gaaatcaagc gcactgtgga cggggaagga    2340
tacaacgtgg cccaatgcaa catgaccaaa gactggttcc tggtccagat gcttgccaac    2400
tacaacattg gctaccaggg cttctacatc cctgagggat acaaggatcg catgtactcc    2460
ttcttcagaa acttccagcc catgagcagg caggtggttg atgaggttaa ttacaaggac    2520
tacaaagccg tcaccttacc ctaccaacac aacaactctg gctttgtagg ttaccttgcg    2580
cctactatgc gacaagggca acccctacccc gccaactacc cataccccgct catcggaact   2640 actgccgtta acagtgtcac ccagaaaaag ttcctgtgcg acaggaccat gtggcgcatt    2700
cccttctcca gcaacttcat gtccatgggc gcccttaccg acctgggaca gaacatgctc    2760
tatgccaact ccgcccatgc gctggacatg acttttgagg tggatcccat ggatgagccc    2820
accctgcttt atcttctttt cgaagtcttc gacgtggtca gagtgcacca gccacaccgc    2880
ggcgtcatcg aggccgtcta cctgcgcaca ccgttctcgg ccggcaacgc caccacataa    2940
```

<210> SEQ ID NO 27
<211> LENGTH: 100
<212> TYPE: DNA

```
<213> ORGANISM: Human adenovirus type 4
<220> FEATURE:
<221> NAME/KEY: misc_feature
<222> LOCATION: (1)..(100)
<223> OTHER INFORMATION: Ad4FS_AF_hexon
      previously described sequences for human adenovirus hexon gene
      regions
      n is a, c, g, or t

<400> SEQUENCE: 27
agtggnnnnn nnnnnnnnnn nnnnnnnnnn nnnnnnnnnn nnnnaaggat gcnnnnnnta     60
acagcaaann nnnnnnnnnn nnnnnnatnn nnngcatacc                          100

<210> SEQ ID NO 28
<211> LENGTH: 100
<212> TYPE: DNA
<213> ORGANISM: Human adenovirus type 4
<220> FEATURE:
<221> NAME/KEY: misc_feature
<222> LOCATION: (1)..(100)
<223> OTHER INFORMATION: Ad4FS_army_hexon
      previously described sequences for human adenovirus hexon gene
      regions
      n is a, c, g, or t

<400> SEQUENCE: 28
agtggnnnnn nnnnnnnnnn nnnnnnnnnn nnnnnnnnnn nnnnaaggat gcnnnnnnta     60
acagcaaann nnnnnnnnnn nnnnnnatnn nnngcatacc                          100

<210> SEQ ID NO 29
<211> LENGTH: 100
<212> TYPE: DNA
<213> ORGANISM: Human adenovirus type 4
<220> FEATURE:
<221> NAME/KEY: misc_feature
<222> LOCATION: (1)..(100)
<223> OTHER INFORMATION: Ad4vaccine_hexon
      previously described sequences for human adenovirus hexon gene
      regions
      n is a, c, g, or t

<400> SEQUENCE: 29
agtggnnnnn nnnnnnnnnn nnnnnnnnnn nnnnnnnnnn nnnnaaggat tcnnnnnntg     60
acagcaaann nnnnnnnnnn nnnnnnatnn nnngcatacc                          100

<210> SEQ ID NO 30
<211> LENGTH: 100
<212> TYPE: DNA
<213> ORGANISM: Human adenovirus type 4
<220> FEATURE:
<221> NAME/KEY: misc_feature
<222> LOCATION: (1)..(100)
<223> OTHER INFORMATION: Ad4_hexon
      previously described sequences for human adenovirus hexon gene
      regions
      n is a, c, g, or t

<400> SEQUENCE: 30
agtggnnnnn nnnnnnnnnn nnnnnnnnnn nnnnnnnnnn nnnnaaggat tcnnnnnntg     60
acagcaaann nnnnnnnnnn nnnnnnatnn nnngcatacc                          100

<210> SEQ ID NO 31
<211> LENGTH: 100
<212> TYPE: DNA
<213> ORGANISM: Human adenovirus type 16
<220> FEATURE:
<221> NAME/KEY: misc_feature
<222> LOCATION: (1)..(100)
```

<223> OTHER INFORMATION: Ad16_hexon
    previously described sequences for human adenovirus hexon gene
    regions
    n is a, c, g, or t

<400> SEQUENCE: 31
agtggnnnnn nnnnnnnnnn nnnnnnnnnn nnnnaaggat tcnnnnnntg     60
acagcaaann nnnnnnnnnn nnnnnnatnn nnngcatacc                100

<210> SEQ ID NO 32
<211> LENGTH: 100
<212> TYPE: DNA
<213> ORGANISM: Human adenovirus type 3
<220> FEATURE:
<221> NAME/KEY: misc_feature
<222> LOCATION: (1)..(100)
<223> OTHER INFORMATION: Ad3FS_navy_hexon
    previously described sequences for human adenovirus hexon gene
    regions
    n is a, c, g, or t

<400> SEQUENCE: 32
agtggatnnn nnnnnnagtt acnnnnnnnn nnnnnnnnnn nnnaacgaat cgnnnnnnag     60
acaatgcagt aactaccann nnnnccacnn nnnaaacaca                100

<210> SEQ ID NO 33
<211> LENGTH: 100
<212> TYPE: DNA
<213> ORGANISM: Human adenovirus type 3
<220> FEATURE:
<221> NAME/KEY: misc_feature
<222> LOCATION: (1)..(100)
<223> OTHER INFORMATION: Ad3_hexon
    previously described sequences for human adenovirus hexon gene
    regions
    n is a, c, g, or t

<400> SEQUENCE: 33
agtggatnnn nnnnnnagtt acnnnnnnnn nnnnnnnnnn nnnaacaaat ggnnnnnngg     60
acaatgcagt aactaccann nnnnccacnn nnnaaacaca                100

<210> SEQ ID NO 34
<211> LENGTH: 100
<212> TYPE: DNA
<213> ORGANISM: Human adenovirus type 7
<220> FEATURE:
<221> NAME/KEY: misc_feature
<222> LOCATION: (1)..(100)
<223> OTHER INFORMATION: Ad7_hexon
    previously described sequences for human adenovirus hexon gene
    regions
    n is a, c, g, or t

<400> SEQUENCE: 34
agtggatnnn nnnnnnagtt acnnnnnnnn nnnnnnnnnn nnnagcagga gannnnnnag     60
aaagagcagt aactaccann nnnnccacnn nnnaaacaca                100

<210> SEQ ID NO 35
<211> LENGTH: 100
<212> TYPE: DNA
<213> ORGANISM: Human adenovirus type 7
<220> FEATURE:
<221> NAME/KEY: misc_feature
<222> LOCATION: (1)..(100)
<223> OTHER INFORMATION: Ad7FS_navy_hexon
    previously described sequences for human adenovirus hexon gene
    regions
    n is a, c, g, or t

<400> SEQUENCE: 35
agtggatnnn nnnnnnagtt acnnnnnnnn nnnnnnnnnn nnnaacggga gannnnnnag    60
acaatgcnnn nnnnnncann nnnnccacnn nnnatacaca                         100

<210> SEQ ID NO 36
<211> LENGTH: 100
<212> TYPE: DNA
<213> ORGANISM: Human adenovirus type 7
<220> FEATURE:
<221> NAME/KEY: misc_feature
<222> LOCATION: (1)..(100)
<223> OTHER INFORMATION: Ad7vaccine_hexon
      previously described sequences for human adenovirus hexon gene
      regions
      n is a, c, g, or t

<400> SEQUENCE: 36
agtggatnnn nnnnnnagtt acnnnnnnnn nnnnnnnnnn nnnaacggga gannnnnnag    60
acaatgcnnn nnnnnncann nnnnccacnn nnnatacaca                         100

<210> SEQ ID NO 37
<211> LENGTH: 100
<212> TYPE: DNA
<213> ORGANISM: Human adenovirus
<220> FEATURE:
<221> NAME/KEY: misc_feature
<222> LOCATION: (1)..(100)
<223> OTHER INFORMATION: EMBOSS_001
      previously described sequences for human adenovirus hexon gene
      regions
      n is a, c, g, or t

<400> SEQUENCE: 37
agtggatgga tacagannnt actcaggann nnnnnnnnnn nnnaatggnn nnanaactng    60
acaatgcngn aactgncann nnnnccacgg aagangnana                         100

<210> SEQ ID NO 38
<211> LENGTH: 100
<212> TYPE: DNA
<213> ORGANISM: Human adenovirus type 21
<220> FEATURE:
<221> NAME/KEY: misc_feature
<222> LOCATION: (1)..(100)
<223> OTHER INFORMATION: Ad21_hexon
      previously described sequences for human adenovirus hexon gene
      regions
      n is a, c, g, or t

<400> SEQUENCE: 38
agtggattgc tgaaggcgtn aaaaaaannn nnnnnnnnnn nnnngaagat gggggatctg    60
acgaagagga agagaaaaat ctcaccacnn nnnttacact                         100

<210> SEQ ID NO 39
<211> LENGTH: 100
<212> TYPE: DNA
<213> ORGANISM: Human adenovirus type 50
<220> FEATURE:
<221> NAME/KEY: misc_feature
<222> LOCATION: (1)..(100)
<223> OTHER INFORMATION: Ad50_hexon
      previously described sequences for human adenovirus hexon gene
      regions
      n is a, c, g, or t

<400> SEQUENCE: 39
agtggcttaa taagggnnnn agatgaannn nnnnnnnnnn nnnngaggat ggggaannng    60

-continued

```
acgaccaaca agnnnnnnnn nnnnctacnn nnnatacact                          100
```

<210> SEQ ID NO 40
<211> LENGTH: 100
<212> TYPE: DNA
<213> ORGANISM: Human adenovirus type 34
<220> FEATURE:
<221> NAME/KEY: misc_feature
<222> LOCATION: (1)..(100)
<223> OTHER INFORMATION: Ad34_hexon
    previously described sequences for human adenovirus hexon gene
    regions
    n is a, c, g, or t

<400> SEQUENCE: 40

```
agtggttgga taagggagtt acaagcactg gnnnnnncct agtggaggat ggcaatactg    60
atgatgggga agaagccaaa aaagcaacnn nnnatacact                         100
```

<210> SEQ ID NO 41
<211> LENGTH: 100
<212> TYPE: DNA
<213> ORGANISM: Human adenovirus type 1
<220> FEATURE:
<221> NAME/KEY: misc_feature
<222> LOCATION: (1)..(100)
<223> OTHER INFORMATION: Ad1_hexon
    previously described sequences for human adenovirus hexon gene
    regions
    n is a, c, g, or t

<400> SEQUENCE: 41

```
agtgggaaca agaagaacca actcaggaaa tggctgaaga acttgaagat gaggaggagg    60
cagaggagga ggaggcagag gaggaggcnn nagaagcacc                         100
```

<210> SEQ ID NO 42
<211> LENGTH: 100
<212> TYPE: DNA
<213> ORGANISM: Human adenovirus type 5
<220> FEATURE:
<221> NAME/KEY: misc_feature
<222> LOCATION: (1)..(100)
<223> OTHER INFORMATION: Ad5FS_hexon
    previously described sequences for human adenovirus hexon gene
    regions
    n is a, c, g, or t

<400> SEQUENCE: 42

```
aatgggatga agctgctact gctcttgaaa tnnnnnnaaa cctagaagaa gaggacgatg    60
acaacgaaga cgaagtagac gagnnnnnnn nnnnnnnnn                          100
```

<210> SEQ ID NO 43
<211> LENGTH: 3011
<212> TYPE: DNA
<213> ORGANISM: Human adenovirus
<220> FEATURE:
<221> NAME/KEY: misc_feature
<222> LOCATION: (1)..(3011)
<223> OTHER INFORMATION: consensus sequence from the previous sequences
    where the sequence gaps have been filled n is a, c, g, or t

<400> SEQUENCE: 43

```
aacaggatgc ttcggagtac ctgagtccgg gtctggtgca gttcgcccgc gtggccaccc    60
catcgatgat gccccagtgg gcatacatgc acatcgccgg ccacagacac ctacttcagt   120
ctggggaaca agtttagaaa ccccacggtg gcgcccaccc acgatgtgac caccgaccgt   180
agccagcggc tgatgctgcg cttcgtgccc gttgaccggg aggacaatac ctactcttac   240
```

```
aaagtgcgct acacgctggc tgtgggcgac aacagagtgc tggacatggc cagcacattc    300
tttgacattc ggggcgtgct ggatagaggc cctagcttca agccctactc cggcactgct    360
tacaactcac tggctcctaa gggcgcgccc aatacatctc agtggatgga tacagannnt    420
actcaggaaa tggctgaaga actaatggnn nnanaactng caatgcngn aactgncaag    480 gaggccacgg aagangnana nnangnnnnn nnnncnacat acacctattg gcatnnnnnn    540
aatgctgcca tgccaattgg aatagatatt actnctactg aaggaganga caaaccaatt    600
taaaaggtga gacnccttnn nctgggaaaa ttactaaaga tgaaggtctg ccaattggaa    660
tagatattac tnctactgaa ggagangaca aaccaattta tgctgataaa acttatcaac    720
cagaacctca agttggagaa gaaacttgga ctgacactga tggaacaaat gaaaatatg    780 ganggcagag ctctaaaacc agctactaaa atgaaaccct gctacgggtc ttttgccaaa    840
cctacaaaca taaaggggg tcaggctaaa ataaaagnaa tcaaaaacaa caaccgaagg    900
agccatngat cctgagtatc cagatattga tatgngaatt ttttgacggt aaaaatactg    960
ttgnagctga cttcgatcct gaaattgtaa tgtacacaga aaatgttgat ttggaaactc    1020
cagacactca tgttgtatac aaacctggaa cttcggatgc nagctctcat gcaaatttgg    1080
gtcaacaagc catgcctaac agacccaact acattggctt cagggacaac tttatcgggc    1140
tcatgtacta caacagtact ggcaatatgg gagttctggc cggccaagca tctcagctga    1200
atgcagtggt tgacttgcag gacagaaaca ctgaactgtc atatcagctc ttgcttgatt    1260
ctctgggtga cagaaccaga tacttcagta tgtggaatca ggctgtggac agctatgatc    1320
ctgatgtgcg cattattgaa aatcatggtg tggaggatga actgccaaac tactgctttc    1380
cgttggatgg tgtaggtcna ccaacagaca cttaccaagg tattaaagtt aaaacagatg    1440
aaantnctga atnnnnnnnn nnnnagtggg acaaagatgn taacgcagtt agaactgcta    1500
atgaaatagc tgtaggcaat cctttttgcca tggaaattaa catccaagcc aacctgtgga    1560
gaagtttcct gtattccaat gtggctctgt atctgccaga taattacaaa tacacgccag    1620
ccaacatcac tctgcccact aacaccaaca cctacgagta catgaacggg cgggtggtgg    1680
ccccatcgct ggtggattcc tacattaaca ttggcgccag gtggtctctg gaccccatgg    1740
acaatgtcaa tccattcaac caccaccgca atgctggcct cgctaccgg tccatgcttc    1800 tgggcaatgg tcgttatgtg cctttccaca tacaagtgcc tcagaaattc tttgctgtca    1860
agaacctact gcttctaccc ggctcctaca cctacgagtg gaacttcaga aaggatgtga    1920
acatggtcct gcagagttcc cttggaaatg acctccgaac agatggtgcc accataagtt    1980
tcaccagcat caacctctat gccaccttct tccccatggc tcacaacacc gcctccaccc    2040
ttgaagccat gctgcgcaac gacaccaatg atcagtcatt caacgactac ctctctgcag    2100
ccaacatgct ctaccccatc cctgccaatg caaccaacgt tcccatctcc atccctctc    2160 gcaactgggc cgccttcagc ggctggtcct tcaccagact caaaaccaag gagactccct    2220
ctctgggatc agggtcgac ccctacttcg tctactctgg ctctattccc tacctggatg    2280 gcaccttta ccttaaccac actttcaaga aggtctccat catgtttgac tcttcagtca    2340
gctggcctgg caatgacagg ctgctgactc caaacgagtt tgaaatcaag cgcactgtgg    2400
acggggaagg atacaacgtg gcccaatgca acatgaccaa agactggttc ctggtccaga    2460
tgcttgccaa ctacaacatt ggctaccagg gcttctacat ccctgaggga tacaaggatc    2520
gcatgtactc cttcttcaga aacttccagc ccatgagcag gcaggtggtt gatgaggtta    2580
attacaagga ctacaaagcc gtcaccttac cctaccaaca caacaactct ggctttgtag    2640
```

```
gttaccttgc gcctactatg cgacaagggc aaccctaccc cgccaactac ccatacccgc    2700
tcatcggaac tactgccgtt aacagtgtca cccagaaaaa gttcctgtgc gacaggacca    2760
tgtggcgcat tcccttctcc agcaacttca tgtccatggg cgcccttacc gacctgggac    2820
agaacatgct ctatgccaac tccgcccatg cgctggacat gacttttgag gtggatccca    2880
tggatgagcc caccctgctt tatcttcttt tcgaagtctt cgacgtggtc agagtgcacc    2940
agccacaccg cggcgtcatc gaggccgtct acctgcgcac accgttctcg gccggcaacg    3000
ccaccacata a                                                          3011

<210> SEQ ID NO 44
<211> LENGTH: 2961
<212> TYPE: DNA
<213> ORGANISM: Unknown
<220> FEATURE:
<223> OTHER INFORMATION: subsequence selected from "Hypothetical
      consensus sequence EMBOSS_001_modified_hexon_cons" as parsed by
      CIBSI algorithm with corresponding returns generated by blastn
      algorithm
<220> FEATURE:
<221> NAME/KEY: Unsure
<222> LOCATION: (1)..(2961)
<220> FEATURE:
<221> NAME/KEY: misc_feature
<222> LOCATION: (1)..(2961)
<223> OTHER INFORMATION: n is a, c, g, or t

<400> SEQUENCE: 44
atggccaccc catcgatgat gccccagtgg gcatacatgc acatcgccgg acaggatgct     60
tcggagtacc tgagtccggg tctggtgcag ttcgcccgcg ccacagacac ctacttcagt    120
ctggggaaca gtttagaaa ccccacggtg gcgcccaccc acgatgtgac caccgaccgt     180
agccagcggc tgatgctgcg cttcgtgccc gttgaccggg aggacaatac ctactcttac    240
aaagtgcgct acacgctggc tgtgggcgac aacagagtgc tggacatggc cagcacattc    300
tttgacattc ggggcgtgct ggatagaggc cctagcttca gcccctactc cggcactgct    360
tacaactcac tggctcctaa gggcgcgccc aatacatctc agtggatgga tacagannnt    420
actcaggaaa tggctgaaga actaatggnn nnanaactng acaatgcngn aactgncaag    480
gaggccacgg aagangnana nnangnnnnn nnnncnacat acacctattg gcatnnnnnn    540
aatgctgcca tgaaaggtga gacnccttnn nctgggaaaa ttactaaaga tgaaggtctg    600
ccaattggaa tagatattac tnctactgaa ggagangaca aaccaattta tgctgataaa    660
acttatcaac cagaacctca gttggagaa gaaacttgga ctgacactga tggaacaaat    720
gaaaaatatg ganggcagag ctctaaaacc agctactaaa atgaaaccct gctacgggtc    780
ttttgccaaa cctacaaaca taaaaggggg tcaggctaaa ataaaagnaa tcaaaaacaa    840
caaccgaagg agccatngat cctgagtatc cagatattga tatgngaatt ttttgacggt    900
aaaaatactg ttgnagctga cttcgatcct gaaattgtaa tgtacacaga aaatgttgat    960
ttggaaactc cagacactca tgttgtatac aaacctggaa cttcggatgc nagctctcat   1020
gcaaatttgg gtcaacaagc catgcctaac agacccaact acattggctt cagggacaac   1080
tttatcgggc tcatgtacta caacagtact ggcaatatgg gagttctggc cggccaagca   1140
tctcagctga atgcagtggt tgacttgcag gacagaaaca ctgaactgtc atatcagctc   1200
ttgcttgatt ctctgggtga cagaaccaga tacttcagta tgtggaatca ggctgtggac   1260
agctatgatc ctgatgtgcg cattattgaa aatcatggtg tggaggatga actgccaaac   1320
tactgctttc cgttggatgg tgtaggtcna ccaacagaca cttaccaagg tattaaagtt   1380
```

```
aaaacagatg aaantnctga atnnnnnnnn nnnnagtggg acaaagatgn taacgcagtt    1440
agaactgcta atgaaatagc tgtaggcaat ccttttgcca tggaaattaa catccaagcc    1500
aacctgtgga aagtttcct gtattccaat gtggctctgt atctgccaga taattacaaa     1560
tacacgccag ccaacatcac tctgcccact aacaccaaca cctacgagta catgaacggg    1620
cgggtggtgg ccccatcgct ggtggattcc tacattaaca ttggcgccag gtggtctctg    1680
gaccccatgg acaatgtcaa tccattcaac caccaccgca atgctggcct cgctaccgga    1740
tccatgcttc tgggcaatgg tcgttatgtg cctttccaca tacaagtgcc tcagaaattc    1800
tttgctgtca agaacctact gcttctaccc ggctcctaca cctacgagtg aacttcaga    1860 aaggatgtga acatggtcct gcagagttcc cttggaaatg acctccgaac agatggtgcc    1920
accataagtt tcaccagcat caacctctat gccaccttct tccccatggc tcacaacacc    1980
gcctccaccc ttgaagccat gctgcgcaac gacaccaatg atcagtcatt caacgactac    2040
ctctctgcag ccaacatgct ctaccccatc cctgccaatg caaccaacgt tcccatctcc    2100 atccctctc gcaactgggc cgccttcagc ggctggtcct tcaccagact caaaaccaag    2160
gagactccct ctctgggatc agggttcgac ccctacttcg tctactctgg ctctattccc    2220
tacctggatg gcaccttta ccttaaccac actttcaaga aggtctccat catgtttgac    2280
tcttcagtca gctggcctgg caatgacagg ctgctgactc caaacgagtt tgaaatcaag    2340
cgcactgtgg acggggaagg atacaacgtg gcccaatgca acatgaccaa agactggttc    2400
ctggtccaga tgcttgccaa ctacaacatt ggctaccagg gcttctacat ccctgaggga    2460
tacaaggatc gcatgtactc cttcttcaga aacttccagc ccatgagcag gcaggtggtt    2520
gatgaggtta attacaagga ctacaaagcc gtcaccttac cctaccaaca caacaactct    2580
ggctttgtag gttaccttgc gcctactatg cgacaagggc aaccctaccc cgccaactac    2640 ccataccccgc tcatcggaac tactgccgtt aacagtgtca cccagaaaaa gttcctgtgc    2700
gacaggacca tgtggcgcat tcccttctcc agcaacttca tgtccatggg cgcccttacc    2760
gacctgggac agaacatgct ctatgccaac tccgcccatg cgctggacat gacttttgag    2820
gtggatccca tggatgagcc caccctgctt tatcttcttt tcgaagtctt cgacgtggtc    2880
agagtgcacc agccacaccg cggcgtcatc gaggccgtct acctgcgcac accgttctcg    2940
gccggcaacg ccaccacata a                                             2961
```

<210> SEQ ID NO 45
<211> LENGTH: 1534
<212> TYPE: DNA
<213> ORGANISM: Unknown
<220> FEATURE:
<223> OTHER INFORMATION: Hypothetical base call pattern arising from
      simulated hybridization of human adenovirus type 4 to a
      resequencing microarray reference sequence ad4_bl2seq.out1
<220> FEATURE:
<221> NAME/KEY: Unsure
<222> LOCATION: (1)..(1534)
<220> FEATURE:
<221> NAME/KEY: misc_feature
<222> LOCATION: (1)..(1534)
<223> OTHER INFORMATION: n is a, c, g, or t

<400> SEQUENCE: 45

```
nnnnnnnnnn nnnnnnnnnn nnnnnnnnnn nnnnnnnnnn nnnnntgtag gcaatccttt      60
tgccatggaa atnaacatcc aagccaacct gtggagnann nnnnnnnnnn nnnnnnnnnn     120
nnnnnnnnnn nnnnnnnnnn nnnnnnnnnn nnnnnnnnnn nnnnnntgc ccacnaacac      180
```

-continued

```
caacacctac gagtacatga acggncgggt ggtggcnnnn nnnnnnnnnn nnnnnnnnnn    240
nnnnnnnnnn nnnnnnnnnn nnnnnnnnnn nnnnnnnnnn nnnnatccnt tcaaccacca    300
ccgcaatgcn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnccggntc    420
ctacacctac gagtggaact tcngnnnnnn nnnnacatg ntcctgcaga gttcccttgg     480
nnnnnnnnnn nnnnnnnnnn nnnnnnnnnn nnnnnnnnnn nnnnnnnacc tctangccac    540
cttcttcccc atggcncaca acaccgcctc cacnnttgan gccatgctgc gcaacgacac    600
caatgancan nnnnnnnnnn nnnnnnnnnn nnnnnnnnnn nnnnnnnnnn nnnnnnnnnn    660
nnnnnnnncc aacgtnccca tctccatccc ctcncgcaac tgggccgcct tnnnnnnnnn    720
nnnnnnnnnn nnnnnnnnnn nnnnnnnnnn nnnnnnnnnn nnnncngggt tcgacccccta   780 cttcgtctac tcnggctcnn nnnnnnnnnn nnnnnnnnnn nnnnnnnaca agaaggtctc    840
catcannnnn nnnnnnnnnn nnnnnnnnnn nnnnnnnnnn nnnnnnnnnn nnnnnnnnnn    900
nnnnnnnnnn nnnnnnnnnn nnnnnnnnnn nngatacaac gtggcccant gcaacatgac    960
caangactgg ttcctggtcc agatgctngc cnnctacaac atnggctacc agggcttcta   1020
cnnnnnnnnn nnnnacaagg ancgcatgta ctccttcttc nnnnnnnnnn nnnnnnnnnn   1080
nnnnnnnnnn nnnnnnnnnn nnnnnnnnnn nnnnnnnnnn nnnnnnnnnn nnnnctacca   1140
acacaacaac tcnggcttnn nnnnnnnnnn nnnnnnnnnn nnnnnnnnnn nnnnnnccta   1200
ccccgccaac taccntacc cgctcatcgg nnnnnnnnnn nnnnnnnnnn nnnnnnnnnn    1260
nnnnnnnnnn nnnnnnnnnn nnatgtggcg catnccctc tccagcaact tcatgtccat   1320
gggcgcnctn nnnnnnnnnn nnnagaacat gctctatgcn aactccgccc annnnnnnnn   1380
nnnnnnnnnn nnnnnnnnnn nnnnnnnnnn nnnnnnnnnn nnnnnnnnnn nnnnnnnnnn   1440
nnnnnnnnnn nnnnagtgc accagccnca ccgcggcgtc atngaggccg tctacctgcg   1500
cacnnnnnnn nnnnnnnnnn nnnnnnnnnn nnnn                              1534
```

<210> SEQ ID NO 46
<211> LENGTH: 2891
<212> TYPE: DNA
<213> ORGANISM: Human adenovirus
<220> FEATURE:
<221> NAME/KEY: misc_feature
<222> LOCATION: (1)..(2891)
<223> OTHER INFORMATION: hypothetical consensus sequence that has been
      redefined to identify a larger number of human adenoviruses
      n is a, c, g, or t

<400> SEQUENCE: 46

```
atggccaccc catcgatgat gccccagtgg gcatacatgc acatcgccgg acaggatgct     60
tcggagtacc tgagtccggg tctggtgcag ttcgcccgcg ccacagacac ctacttcagt    120
ctggggaaca gtttagaaa ccccacggtg gcgcccaccc acgatgtgac caccgaccgc    180
agccagcggc tgatgctgcg cttcgtgccc gttgaccggg aggacaatac ctactcgtac    240
aaagtgcgct acacgctggc cgtgggcgac aacagagtgc tggacatggc cagcaccttc    300
tttgacatcc gcgcgtgct ggataggggc cctagcttca gccctactc cggcactgcc     360 tacaacaccc tggctcccaa gggagcgccc aacacctgcc agtggaannn ggatgctgnn    420
nnnnnnnnnn nnnacnnagc agannnnnnn nagaaaaann nnnanntncc accacgcaca    480
cctttgggat agctgccatg acgggtgtta ctgggaaaat gattgaagct gaagggctgc    540
caattggaat agnnatataa ctgctggaac tgacacacca atttatgctg ataaaacatt    600
```

```
ccaaccagaa cctcaagttg gaaatgaaac ttgggttgac accaatggta caaatgaaaa    660
atatggnagg cagagctcta aaggacacta caaaaatgaa accctgctat ggttcttttg    720
ccaaacctac caacaaaaaa ggtggccagg ctaaacttaa aaaattaaga acccgccgcc    780
ggaccagtcg aggctgacta gcctgatatt gatctggatt tctttgacgg cagnagatat    840
tgctgactaa cttcgatcca aaaattgtaa tgtacacaga aaatgttgac ttggaaactc    900
cagacactca tattgtatac aaacctggaa ctgaggacgc cagctctcaa gccaatttgg    960
gtcaacaagc catgcctaac agacccaact acattggctt cagagacaat tttattgggc   1020
tcatgtacta caacagcact ggcaatatgg gggttctggc cggtcaagca tctcagctga   1080
atgctgtggt tgacttgcaa gacagaaaca ctgaactgtc ataccagctc ttgcttgact   1140
ctctgggtga cagaaccagg tacttcagta tgtggaatca ggcggtggac agctatgatc   1200
ctgatgtgcg cattattgaa aatcatggtg tggaggatga actgccaaac tactgctttc   1260
cgttggatgg tgtgggnnna ttaacagaca cttaccaagg tattaaagct aaaacagatg   1320
caggttctga aannnnnnnn nnnnagtggg acaaagatga caccaaagtt agtactgcta   1380
atgaaatcca tgtaggcaat ccttttgcca tggaaatcaa catccaagcc aacctgtgga   1440
gaagtttcct gtattccaat gtggctctgt atctgccaga taaatacaaa tacacaccgg   1500
ccaacatcac tctgcccgcc aacaccaaca cctacgagta catgaacggg cgggtggtgg   1560
cgccatcgct ggtggactcc tacattaaca ttggcgccag ctggtctctg accccatgg    1620
acaatgtaaa tccattcaac caccaccgca atgctggcct gcgctaccgc tccatgcttc   1680
tgggcaatgg gcgttatgtg cctttccaca tccaagtgcc tcagaaattc tttgctgtca   1740
agaacctact gcttctgccc ggctcctaca cctacgagtg gaacttcaga aaggatgtga   1800
acatggtcct gcagagttcc cttggaaatg acctccgcac agatggtgcc accatcagtt   1860
tcaccagcat caacctctat gccaccttct tccccatggc tcacaacacc gcctccacgc   1920
ttgaagccat gctgcgcaac gacaccaatg atcagtcatt caacgactac ctctctgcag   1980
ccaacatgct ctaccccatc ccggccaatg caaccaacgt tcccatctcc atccctctc    2040
gcaactgggc cgccttcagc ggctggtcct tcacgagact caaaaccaag gagactccct   2100
ctctgggctc agggttcgac ccctacttcg tctactctgg ctctattccc tacctggatg   2160
gcaccttta cctcaaccac actttcaaga aggtctccat catgtttgac tcttcagtca   2220
gctggcctgg caatgacagg ctgctgactc ccaacgagtt tgaaatcaag cgcactgtgg   2280
acggggaagg atacaacgtg gcccaatgca acatgaccaa agactggttc ctggtccaga   2340
tgcttgccaa ctacaacatt ggctaccagg gcttctacat ccctgagggc tacaaggatc   2400
gcatgtactc cttcttcaga aacttccagc ccatgagcag gcaggtggtt gatgaggtta   2460
actacaagga ctacaaagcc gtcaccttac catatcaaca caacaactct ggctttgtag   2520
gataccttgc gcctactatg cgccaagggc aaccctaccc agccaactac ccataccgc    2580
tcatcggaac tactgccgtt aacagtgtca cccagaaaaa gttcctgtgc gacaggacca   2640
tgtggcgcat cccccttctcc agcaacttca tgtccatggg cgcccttacc gacctgggac   2700
agaacatgct ctatgccaac tccgcccatg cgctggacat gacttttgag gtggatccca   2760
tggatgagcc cacctgctt tatcttcttt tcgaagtctt cgacgtggtc agagtgcacc    2820
agccacaccg cggcgtcatc gaggccgtct acctgcgcac accgttctcg gccggcaacg   2880
ccaccacata a                                                        2891
```